United States Patent
Zhang et al.

(10) Patent No.: US 9,688,694 B2
(45) Date of Patent: Jun. 27, 2017

(54) MACROCYCLIC BENZODIAZEPINE DIMERS, CONJUGATES THEREOF, PREPARATION AND USES

(71) Applicant: BRISTOL-MYERS SQUIBB COMPANY, Princeton, NJ (US)

(72) Inventors: Yong Zhang, West Windsor, NJ (US); Robert M. Borzilleri, Carversville, PA (US); Andrew J. Tebben, New Hope, PA (US); Erik M. Stang, Sterling, VA (US); Andrew F. Donnell, West Windsor, NJ (US); Gretchen M. Schroeder, Ewing, NJ (US); Heidi L. Perez, Ewing, NJ (US); Donna D. Wei, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/189,388

(22) Filed: Jun. 22, 2016

(65) Prior Publication Data
US 2016/0376288 A1 Dec. 29, 2016

Related U.S. Application Data

(60) Provisional application No. 62/183,350, filed on Jun. 23, 2015.

(51) Int. Cl.
| | | |
|---|---|---|
| C07D 487/04 | (2006.01) | |
| C07D 519/00 | (2006.01) | |
| C07D 498/22 | (2006.01) | |
| A61K 31/5513 | (2006.01) | |
| A61K 31/5517 | (2006.01) | |
| A61K 47/48 | (2006.01) | |
| C07K 16/30 | (2006.01) | |

(52) U.S. Cl.
CPC ........ *C07D 498/22* (2013.01); *A61K 31/5513* (2013.01); *A61K 31/5517* (2013.01); *A61K 47/48384* (2013.01); *A61K 47/48569* (2013.01); *A61K 47/48592* (2013.01); *A61K 47/48615* (2013.01); *A61K 47/48638* (2013.01); *A61K 47/48715* (2013.01); *C07D 519/00* (2013.01); *C07K 16/30* (2013.01); *C07K 16/3023* (2013.01); *C07K 16/3046* (2013.01); *C07K 16/3069* (2013.01)

(58) Field of Classification Search
CPC ............................ C07D 519/00; C07D 487/04
See application file for complete search history.

(56) References Cited

U.S. PATENT DOCUMENTS

| | | |
|---|---|---|
| 7,049,311 B1 | 5/2006 | Thurston et al. |
| 7,244,724 B2 | 7/2007 | Liu et al. |
| 7,407,951 B2 | 8/2008 | Thurston et al. |
| 7,528,126 B2 | 5/2009 | Howard et al. |
| 7,557,099 B2 | 7/2009 | Howard et al. |
| 7,612,062 B2 | 11/2009 | Gregson et al. |

(Continued)

FOREIGN PATENT DOCUMENTS

| | | |
|---|---|---|
| WO | WO 2015/085259 | 9/2005 |
| WO | WO 2013/041606 A1 | 3/2013 |

(Continued)

OTHER PUBLICATIONS

Scott Jeffrey et al., *Bio Conjugate Chemistry*, "A Potent Anti-CD70 Antibody—Drug Conjugate Combining a Dimeric Pyrrolobenzodiazepine Drug with Site-Specific Conjugation", vol. 24: pp. 1256-1263, 2013.

(Continued)

*Primary Examiner* — Bruck Kifle
(74) *Attorney, Agent, or Firm* — Yuan Chao

(57) ABSTRACT

Macrocyclic benzodiazepine dimers having a structure represented by formula I

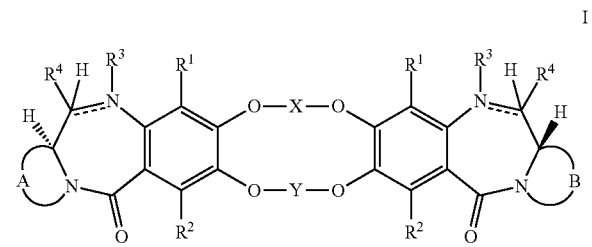

where A and B are independently according to formulae Ia or Ib

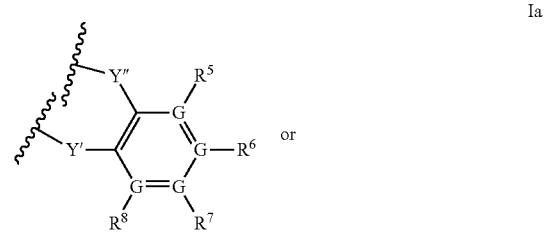

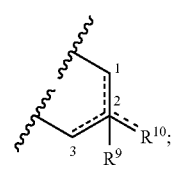

and the other variables in formulae I, Ia, and Ib are as defined in the application. Such dimers are useful as anti-cancer agents, especially when used as the drug component in an antibody-drug conjugate (ADC).

17 Claims, 20 Drawing Sheets

(56) References Cited

U.S. PATENT DOCUMENTS

| | | |
|---|---|---|
| 7,659,241 B2 | 2/2010 | Senter et al. |
| 7,741,319 B2 | 6/2010 | Howard et al. |
| 8,163,736 B2 | 4/2012 | Gauzy et al. |
| 8,404,678 B2 | 3/2013 | Bouchard et al. |
| 8,426,402 B2 | 4/2013 | Li et al. |
| 8,481,042 B2 | 7/2013 | Commercon et al. |
| 8,501,934 B2 | 8/2013 | Howard et al. |
| 8,592,576 B2 | 11/2013 | Howard et al. |
| 8,697,688 B2 | 4/2014 | Howard et al. |
| 8,765,740 B2 | 7/2014 | Li et al. |
| 2007/0191349 A1 | 8/2007 | Howard et al. |
| 2011/0256157 A1 | 10/2011 | Howard et al. |
| 2013/0028919 A1 | 1/2013 | Howard et al. |
| 2013/0137659 A1 | 5/2013 | Commercon et al. |
| 2013/0266595 A1 | 10/2013 | Elygare et al. |
| 2014/0120118 A1 | 5/2014 | Howard |
| 2014/0127239 A1 | 5/2014 | Howard |
| 2014/0234346 A1 | 8/2014 | Howard |
| 2014/0274907 A1 | 9/2014 | Howard et al. |
| 2014/0286970 A1 | 9/2014 | Jeffrey et al. |
| 2014/0294868 A1 | 10/2014 | Howard et al. |
| 2014/0302066 A1 | 10/2014 | Jeffrey et al. |

FOREIGN PATENT DOCUMENTS

| | | |
|---|---|---|
| WO | WO 2013/177481 A1 | 11/2013 |
| WO | WO 2014/031566 A1 | 2/2014 |
| WO | WO 2014/080251 A1 | 3/2014 |
| WO | WO 2014/096365 A1 | 6/2014 |
| WO | WO 2014/096368 A1 | 6/2014 |
| WO | WO 2014/140174 A1 | 9/2014 |
| WO | WO 2014/140862 A2 | 9/2014 |
| WO | WO 2014/174111 A1 | 10/2014 |

OTHER PUBLICATIONS

Stephen J. Gregson, et al., *Bioorganic & Medicinal Chemistry Letters* "Synthesis of the First Example of a C2-C3/C20-C30-endo Unsaturated Pyrrolo[2,1-c][1,4]benzodiazepine Dimer",\ 11: pp. 2859-2862, 2011.

Kiran Kumar Kothakonda, et al., *Bioorganic & Medicinal Chemistry Letters*, "Synthesis of a novel tetrahydroisoquinolino[2,1-c][1,4]benzodiazepine ring system with DNA recognition potential", 14: pp. 4371-4373, 2014.

Stephen J. Gregson et al., *ChemComm*, "Synthesis of a novel C2/C2A-*exo* unsaturated pyrrolobenzodiazepine cross-linking agent with remarkable DNA binding affinity and cytotoxicity", pp. 797-798, 1999.

John A Hartley, *Expert Opinion Investig. Drugs*, "The development of pyrrolobenzodiazepines as antitumour agents", vol. 20: pp. 733-744. 2011.

John A. Hartley, et al., *Invest New Drugs*, "DNA Interstrand cross-linking and in vivo antitumor activity of the extended pyrrolo[2,1-c][1,4]benzodiazepine dimer SG2057", vol. 30: pp. 950-958, 2012.

D. Subhas Bose, et al. *J. Am. Chem. SOC*, "Rational Design of a Highly Efficient Irreversible DNA Interstrand Cross-Linking Agent Based on the Pyrrolobenzodiazepine Wing System", vol. 114: pp. 4939-4941, 1992.

David E. Thurston, et al., *J. Med. Chem*, "Effect of A-Ring Modifications on the DNA-Binding Behavior and Cytotoxicity of Pyrrolo[2,1-c][1,4]benzodiazepines", vol. 42: pp. 1951-1964, 1999.

Stephen J. Gregson et al. *J. Med. Chem* , "Design, Synthesis, and Evaluation of a Novel Pyrrolobenzodiazepine DNA-Interactive Agent with Highly Efficient Cross-Linking Ability and Potent Cytotoxicity", vol. 44: pp. 737-748, 2001.

Stephen J. Gregson et al., *J. Med. Chem* , "Linker Length Modulates DNA Cross-Linking Reactivity and Cytotoxic Potency of C8/C8¢ Ether-Linked C2-*exo*-Unsaturated Pyrrolo[2,1-c][1,4]benzodiazepine (PBD) Dimers", vol. 47: pp. 1161-1174, 2004.

Dyeison Antonow, et al., *J. Med. Chem* , "Structure-Activity Relationships of Monomeric C2-Aryl Pyrrolo[2,1-c][1,4]benzodiazepine (PBD) Antitumor Agents", vol. 53: pp. 2927-2941, 2010.

David E. Thurston, et al., *J. Org. Chem.*, "Synthesis of Sequence-Selective C8-Linked Pyrrolo[2,1-*c*][1,4]benzodiazepine DNA Interstrand Cross-Linking", vol. 61: pp. 8141-8147, 1996.

David Schrama et al., *Nature Reviews Drug Discovery*, "Antibody targeted drugs as cancer Therapeutics", vol. 5: pp. 147-159, 2006.

International Search Report and Written Opinion, for PCT Application No. PCT/US2016/038750, mailed Sep. 19, 2016.

FIG. 7

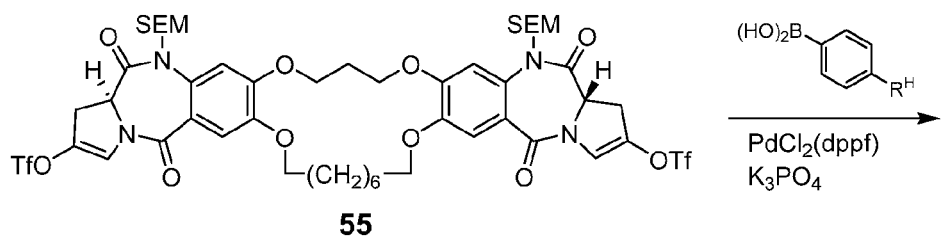

55

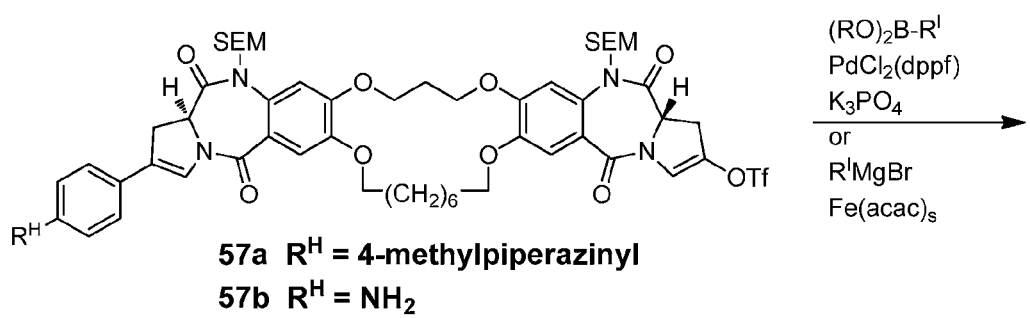

57a $R^H$ = 4-methylpiperazinyl
57b $R^H$ = NH$_2$

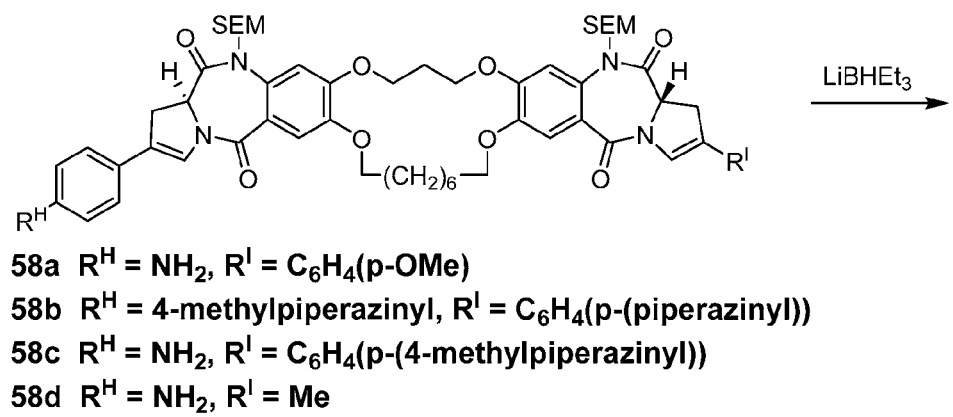

58a $R^H$ = NH$_2$, $R^I$ = C$_6$H$_4$(p-OMe)
58b $R^H$ = 4-methylpiperazinyl, $R^I$ = C$_6$H$_4$(p-(piperazinyl))
58c $R^H$ = NH$_2$, $R^I$ = C$_6$H$_4$(p-(4-methylpiperazinyl))
58d $R^H$ = NH$_2$, $R^I$ = Me

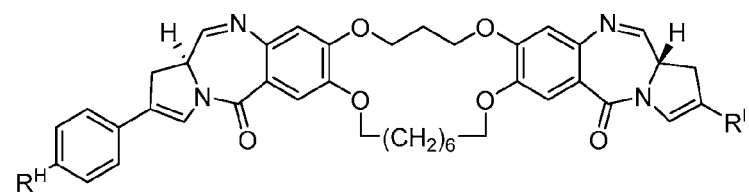

IIc-11 $R^H$ = NH$_2$, $R^I$ = C$_6$H$_4$(p-OMe)
IIc-9 $R^H$ = 4-methylpiperazinyl, $R^I$ = C$_6$H$_4$(p-(piperazinyl))
IIc-10 $R^H$ = NH$_2$, $R^I$ = C$_6$H$_4$(p-(4-methylpiperazinyl))
IId-1 $R^H$ = NH$_2$, $R^I$ = Me

MACROCYCLIC BENZODIAZEPINE DIMERS, CONJUGATES THEREOF, PREPARATION AND USES

CROSS-REFERENCE TO RELATED APPLICATIONS

This application claims the benefit under 35 U.S.C. §119(e) of U.S. Provisional Application Ser. No. 62/183,350; filed Jun. 23, 2015; the disclosure of which is incorporated herein by reference.

BACKGROUND OF THE INVENTION

This invention relates to macrocyclic benzodiazepine dimers, dimer-linker compounds derived therefrom, and conjugates thereof, and methods for their preparation and use.

Some naturally occurring cytotoxins, such as tomaymycin and anthramycin, contain a benzodiazepine ring system. Reflecting the additional presence of a pyrrolidine ring fused to the diazepine ring, these compounds are often referred to as pyrrolobenzodiazepines, or PBDs.

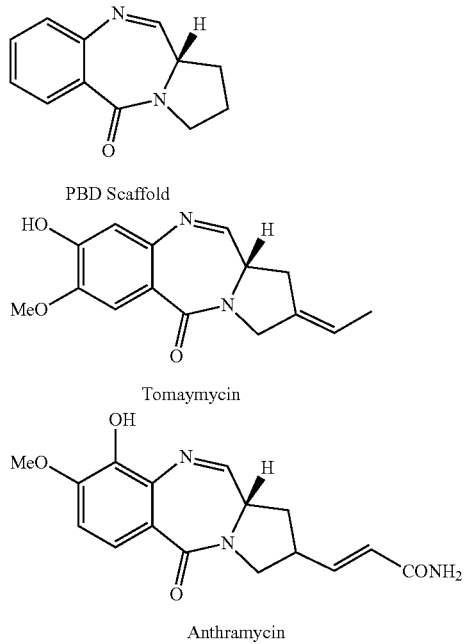

PBDs possess antibiotic and antitumor activity, the latter trait leading to interest in them as anticancer drugs. Mechanistically, PBDs bind to the minor groove of DNA in a sequence selective manner and alkylate the DNA. The structure-activity relationship (SAR) of different substituents has been studied (Antonow et al. 2010; Thurston et al. 1999).

Additional studies have shown that PBD dimers also show special promise as anticancer agents. The core structure of a typical PBD dimer can be represented by formula A-1, where X is a bridging group connecting the two dimer halves.

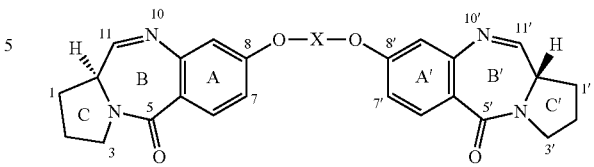

As with monomeric PBDs, the dimers are DNA minor groove binder-alkylators. Being bifunctional, alkylation results in cross-linked DNA, making DNA repair more difficult. (DNA alkylation occurs via the imine group. PDBs having one of the imine groups reduced can still alkylate DNA, but cannot crosslink it. They are still biologically active, albeit generally less so.) For a review on the evolution of PBDs as antitumor agents, from naturally occurring monomers to synthetic monomers to synthetic dimers, see Hartley 2011.

The SAR of PBD dimers has been explored via substituents on the A/A' and C/C' rings, unsaturation in the C/C' rings, the structure and length of the bridging group X, and the oxidation or reduction of the imine double bonds in rings B/B', and combinations of such features. See Bose et al. 1992, Gregson et al. 1999, Gregson et al. 2001a and 2001b, Gregson et al. 2004, Gregson et al. 2009, Hartley et al. 2012, Howard et al. 2007, Howard et al. 2009a. Howard et al. 2010, Howard et al. 2013a and 2013b, Liu et al. 2007, Thurston et al. 1996, Thurston et al. 2006, and Thurston et al. 2008. Most PBD dimers are joined via an 8/8' bridge as shown above, but a 7/7' bridge also has been disclosed (Howard et al. 2009b).

A type of anticancer agent that is generating strong interest is an antibody-drug conjugate (ADC, also referred to as an immunoconjugate). In an ADC, a therapeutic agent (also referred to as the drug, payload, or warhead) is covalently linked to an antibody whose antigen is expressed by a cancer cell (tumor associated antigen). The antibody, by binding to the antigen, delivers the ADC to the cancer site. There, cleavage of the covalent link (referred to as the linker) or degradation of the antibody leads to the release of the therapeutic agent. Conversely, while the ADC is circulating in the blood system, the therapeutic agent is held inactive because of its covalent linkage to the antibody. Thus, the therapeutic agent used in an ADC can be much more potent (i.e., cytotoxic) than ordinary chemotherapy agents because of its localized release. For a review on ADCs, see Schrama et al. 2006.

PBD dimers have been proposed as the drug in an ADC. Attachment of the linker connecting to the antibody can be via a functional group located in a C/C' ring, the bridging group X, or by addition across the imine group in a B/B' ring. See Bouchard et al. 2013, Commercon et al. 2013a and 2013b, Flygare et al. 2013, Gauzy et al. 2012, Howard 2104a-2014e, Howard et al. 2011, Howard et al. 2013c and 2013d, Howard et al. 2014a-2014d, Jeffrey et al. 2013, Jeffrey et al. 2014a and 2014b, and Zhao et al. 2014.

Another type of benzodiazepine dimer also has been proposed as a drug in ADCs. Structurally, this type may be viewed as a PBD dimer further having a phenyl ring fused to each of C/C' rings, as shown in formulae A-2 and A-3. See Chari et al. 2013, Li et al. 2013, Fishkin et al. 2014, Li et al. 2014.

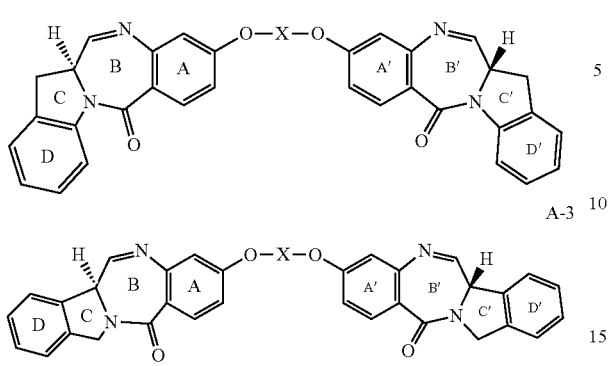

Benzodiazepine compounds having other ring systems, such as a tetrahydro-isoquinolino[2,1-c][1,4]benzodiazepine, also have been disclosed. Kothakonda et al. 2004.

Full citations for the documents cited herein by first author or inventor and year are listed at the end of this specification.

BRIEF SUMMARY OF THE INVENTION

This invention provides novel benzodiazepine dimers, having both an 8/8' bridge and a 7/7' bridge, to form a macrocyclic ring structure, as represented by formula I:

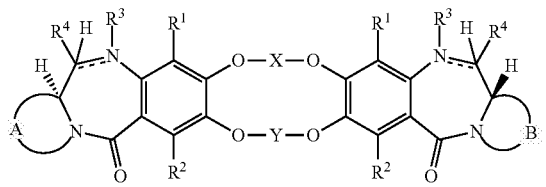

wherein
X is

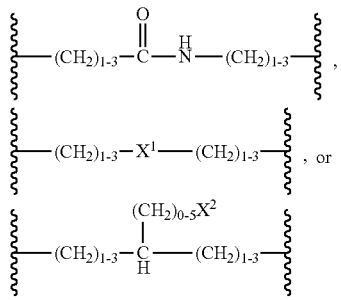

$X^1$ is $CH_2$, O, NH, $S(O)_{0-2}$, 3- to 7-membered cycloalkylene or heterocycloalkylene unsubstituted or substituted with $(CH_2)_{0-5}X^2$ or $O(CH_2)_{2-5}X^2$, or 5- to 6-membered arylene or heteroarylene unsubstituted or substituted with $(CH_2)_{0-5}X^2$ or $O(CH_2)_{2-5}X^2$;

each $X^2$ is independently Me, $CO_2H$, $NH_2$, $NH(C_1\text{-}C_5\text{ alkyl})$, $N(C_1\text{-}C_5\text{ alkyl})_2$, SH, CHO, $N(CH_2CH_2)_2N(C_1\text{-}C_3\text{ alkyl})$, $N(CH_2CH_2)_2NH$, $NHNH_2$, or $C(=O)NHNH_2$;

Y is $(CH_2)_{4-6}CH=CH(CH_2)_{4-6}$, $(CH_2)_{4-6}X^1(CH_2)_{4-6}$, or $(CH_2)_2(OCH_2CH_2)_{2-3}$;

each $R^1$ and $R^2$ is independently H, F, Cl, Br, OH, $C_1\text{-}C_3$ alkyl, $O(C_1\text{-}C_3\text{ alkyl})$, cyano, $(CH_2)_{0-5}NH_2$, or $NO_2$ (with both $R^1$ and $R^2$ preferably being H);

each double line ==== in a diazepine ring system independently represents a single bond or a double bond;

each $R^3$ is H if the double line ==== to the N to which it is attached—i.e., with which it is associated—is a single bond and is absent if the double line is a double bond;

each $R^4$ is H, OH, $SO_3Na$, or $SO_3K$ if the double line ==== to the C to which it is attached—i.e., with which it is associated—is a single bond and is absent if the double line is a double bond;

A and B are independently according to formula Ia or Ib

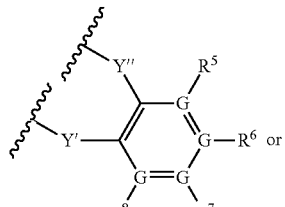

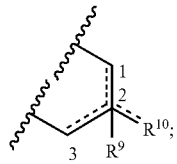

wherein, in formula Ia
Y' and Y" are independently absent, $CH_2$, C=O, or $CHR^{12}$; wherein each $R^{12}$ is independently F, Cl, Br, or $C_1\text{-}C_3$ alkyl, with the proviso that Y' and Y" are not both absent;

each G is independently C or N, with the proviso that no more than two Gs are N; and each $R^5$, $R^6$, $R^7$, and $R^8$ is independently H, $C_1\text{-}C_5$ alkyl, $C\equiv C(CH_2)_{1-5}X^2$, OH, $O(C_1\text{-}C_5\text{ alkyl})$, cyano, $NO_2$, F, Cl, Br, $O(CH_2CH_2O)_{1-8}(C_{1-3}\text{ alkyl})$, $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$,

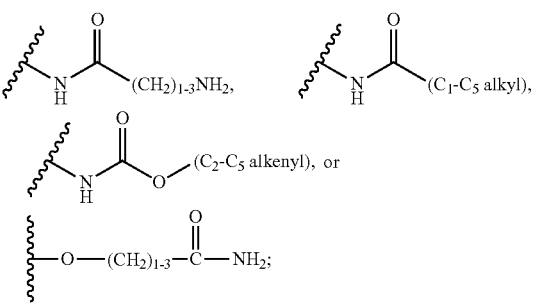

or where a $R^5$, $R^6$, $R^7$, or $R^8$ is attached to—i.e., is associated with—a G that is N, such $R^5$, $R^6$, $R^7$, or $R^8$ is absent;

and
wherein, in formula Ib,
the dotted lines indicate the optional presence of a C1-C2, C2-C3, or C2-$R^{10}$ double bond;
$R^9$ is absent if a C1-C2, C2-C3, or C2-$R^{10}$ double bond is present and otherwise is H; and
$R^{10}$ is H, =O, =$CH_2$, =CH($C_1$-$C_5$ alkyl), CH=CH$(CH_2)_{1-5}X^2$, C≡C$(CH_2)_{1-5}X^2$, $C_1$-$C_5$ alkyl, OH, O($C_1$-$C_5$ alkyl), cyano, $NO_2$, F, Cl, Br, O($CH_2CH_2O)_{1-8}$($C_{1-3}$ alkyl), $(CH_2)_{0-5}X^2$, 4- to 7-membered aryl, heteroaryl, cycloalkyl, or heterocycloalkyl unsubstituted or substituted with $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$;
or a pharmaceutically acceptable salt thereof.

In another embodiment, this invention provides a conjugate comprising a dimer of formula (I) covalently bonded to a targeting moiety that specifically or preferentially binds to a chemical entity on a target cell, which target cell preferably is a cancer cell. Preferably, the targeting moiety is an antibody—more preferably a monoclonal antibody; even more preferably a human monoclonal antibody—and the chemical entity is a tumor associated antigen. The tumor associated antigen can be one that is displayed on the surface of a cancer cell or one that is secreted by a cancer cell into the surrounding extracellular space. Preferably, the tumor associated antigen is one that is over-expressed by the cancer cell compared to normal cells or one that is expressed by cancer cells but not normal cells.

In another embodiment, there is provided a dimer according to formula (I) covalently bonded to a linker moiety having a reactive functional group, suitable for conjugation to a targeting moiety.

In another embodiment, there is provided a method for treating a cancer in a subject suffering from such cancer, comprising administering to the subject a therapeutically effective amount of a dimer of this invention or a conjugate thereof with a targeting moiety. In another embodiment, there is provided the use of a dimer of this invention or a conjugate thereof with a targeting moiety for the preparation of a medicament for the treatment of cancer in a subject suffering from such cancer. A dimer of this invention or a conjugate thereof with a targeting moiety can also be used to inhibit the proliferation, in vitro, ex vivo, or in vivo, of cancer cells. Especially, the cancer is lung, gastric, or ovarian cancer.

BRIEF DESCRIPTION OF THE DRAWING(S)

FIGS. 1A-1B, 2, 3, 4A-4B, 5, 6, 7, 8, 9, and 10 show reaction schemes for the synthesis of dimers of this invention.

FIGS. 11, 12, 13A-13B, 14, and 15 show reaction schemes for the preparation of dimer-linker compounds usable for the preparation of ADCs.

DETAILED DESCRIPTION OF THE INVENTION

Definitions

Figure 1A:
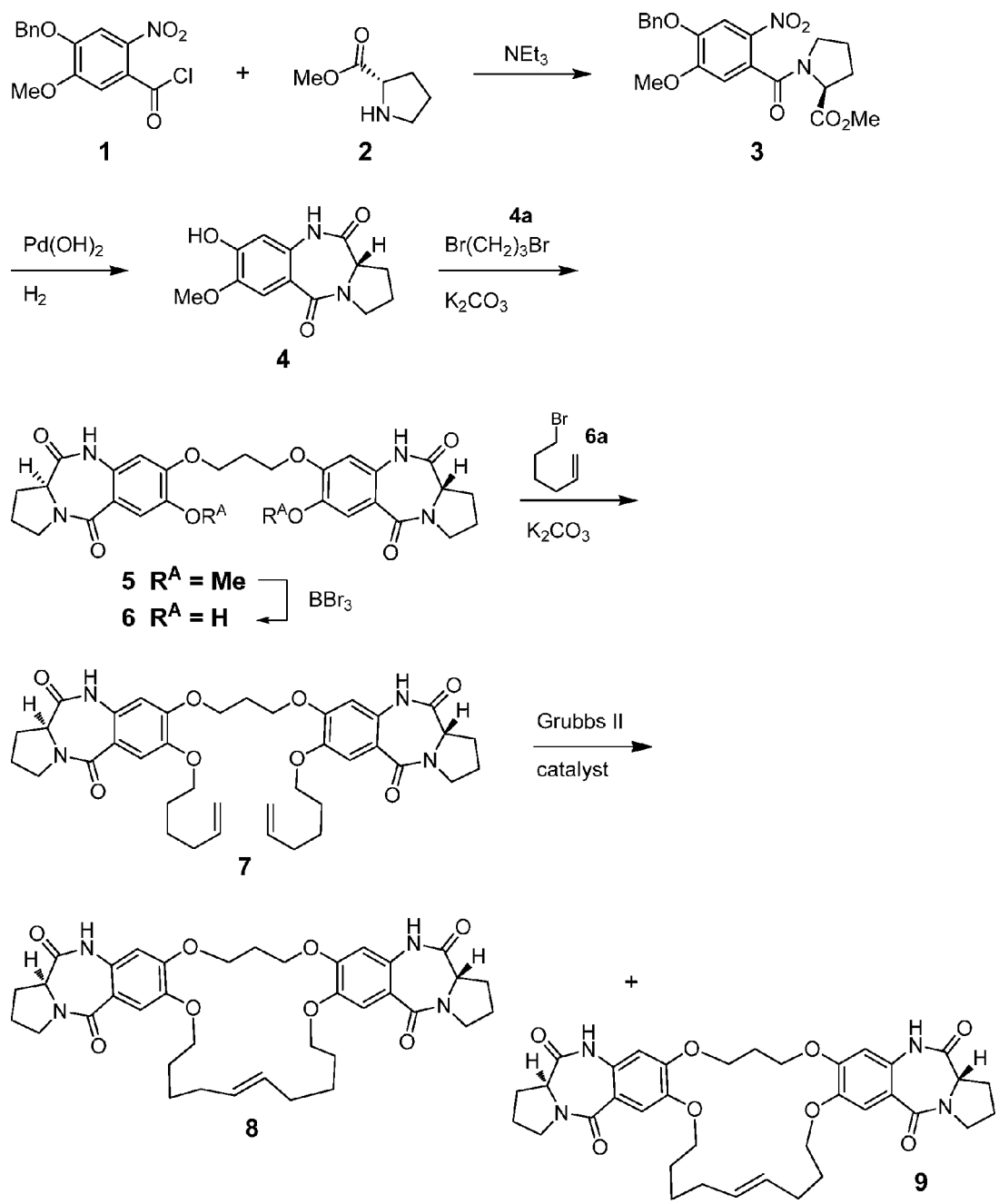

"Antibody" means whole antibodies and any antigen binding fragment (i.e., "antigen-binding portion") or single chain variants thereof. A whole antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and $C_{H1}$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')$_2$, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_{2-4}$ alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl (or, synonymously, $C_{1-4}$ alkyl) moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine.

"Aryl" means a hydrocarbon moiety having a mono-, bi-, or tricyclic ring system wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexyl-phenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system wherein each ring has from 3 to 7 carbon atoms and at least one ring is an aromatic ring containing from 1 to 4 heteroatoms independently selected from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpyridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, $C_1$-$C_4$alkyoxy, O($C_2$-$C_4$ alkylene)OH, and O($C_2$-$C_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are $C_1$-$C_4$ alkyl, cyano, nitro, halo, and $C_1$-$C_4$alkoxy.

Where a range is stated, as in "$C_1$-$C_5$ alkyl" or "5 to 10%," such range includes the end points of the range, as in $C_1$ and $C_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include $C_1$-$C_5$ alkyl, $C_2$-$C_5$ alkenyl or $C_2$-$C_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

In the formulae of this specification, a wavy line (~~~) transverse to a bond or an asterisk (*) at the end of the bond denotes a covalent attachment site. For instance, a statement that R is

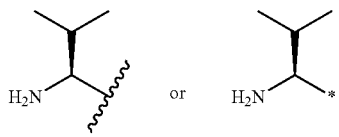

in the formula

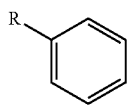

refers to

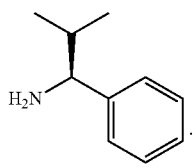

In the formulae of this specification, a bond traversing an aromatic ring between two carbons thereof means that the group attached to the bond may be located at any of the available positions of the aromatic ring. By way of illustration, the formula

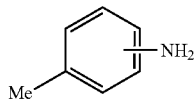

represents

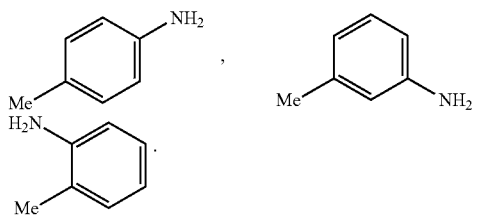

Dimers

Preferably, in formula I, X is a C7/C7' bridge that is 3 or 5 atoms long and Y is a C8/C8' bridge that is 7, 8, 9, 10, 11, or 12 atoms long, where the atoms in each bridge are selected from C, O, N, and S, especially where all the bridge atoms are C or all are C except for one O, N, or S. More preferably, where X is 3 atoms long, Y is 7, 8, 9, or 10 atoms long (even more preferably 8 to 10 atoms long) and where X is 5 atoms long, Y is 11 or 12 atoms long.

In a preferred embodiment, in formula I, X is $(CH_2)_3$ or $(CH_2)_5$.

In another preferred embodiment, in formulae I, IIa, IIb, or IIc (the latter three formulae shown hereinbelow), Y is $(CH_2)_{7-12}$, more preferably $(CH_2)_8$.

In formula I, preferred combinations of X and Y are X equals $(CH_2)_3$ while Y equals $(CH_2)_{8-10}$ and X equals $(CH_2)_5$ while Y equals $(CH_2)_{11-12}$. A more preferred combination is X equals $(CH_2)_3$ and Y equals $(CH_2)_8$.

In another preferred embodiment, in formulae I, IIa, IIb, or IIc, Y is $(CH_2)_2(OCH_2CH_2)_{2-3}$, especially $(CH_2)_2(OCH_2CH_2)_2$.

In another preferred embodiment, in formulae I, IIa, IIb, or IIc, Y is $(CH_2)_4NH(CH_2)_4$ or $(CH_2)_4N(CH_2(p-C_6H_4NH_2))(CH_2)_4$.

In the formulae where it appears, $X^2$ preferably is $NH_2$, SH, or $CO_2H$.

Preferably, where X in formula I is

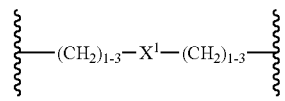

and $X^1$ is O or NH, then X is

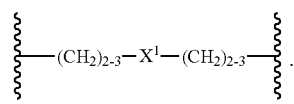

In a preferred embodiment, dimers of this invention have a structure represented by formula IIa, wherein x is 3 or 5 (preferably 3); Y is $(CH_2)_{7-12}$, $(CH_2)_2(OCH_2CH_2)_{1-3}$, $(CH_2)_{2-4}NH(CH_2)_{2-4}$ or $(CH_2)_{2-4}NH((CH_2)_{0-1}phenyl)(CH_2)_{2-4}$ where the phenyl group is optionally substituted with $NH_2$; A is A1, A2, or A3 as depicted below, and B is B1, B2, or B3 as depicted below. Representative species are listed in Table 1.

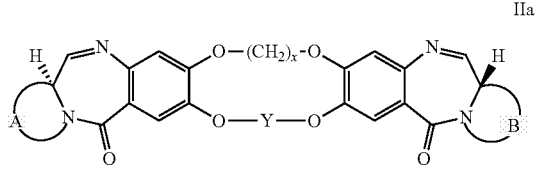

IIa

A1

A2

-continued

A3

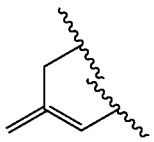

B1

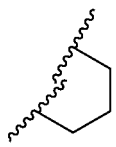

B2

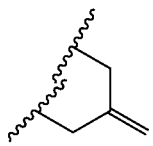

TABLE 1-continued

Examples of Dimers According to Formula IIa

| Dimer | x | Y | A | B |
|---|---|---|---|---|
| IIa-11 | 3 | $(CH_2)_{10}$ | A3 | B3 |
| IIa-12 | 3 | $(CH_2)_8$ | A2 | B2 |
| IIa-13 | 3 | $(CH_2)_2(OCH_2CH_2)_2$ | A2 | B2 |
| IIa-14 | 3 | $(CH_2)_4NH(CH_2)_4$ | A2 | B2 |

In another preferred embodiment, dimers of this invention have a structure represented by formula IIb, where x is 3 or 5 (preferably 3), each Y' is independently absent or $CH_2$, Y is $(CH_2)_{7-12}$, $(CH_2)_2(OCH_2CH_2)_{1-3}$, $(CH_2)_{2-4}NH(CH_2)_{2-4}$ or $(CH_2)_{2-4}NH((CH_2)_{0-1}phenyl)(CH_2)_{2-4}$ where the phenyl group is optionally substituted with $NH_2$; and $R^{40}$ and $R^{41}$ are independently H, Cl, Br, OH, $O(C_{1-3}$ alkyl), $NH_2$, or $C_{1-3}$ alkyl. Representative species are listed in Table 2.

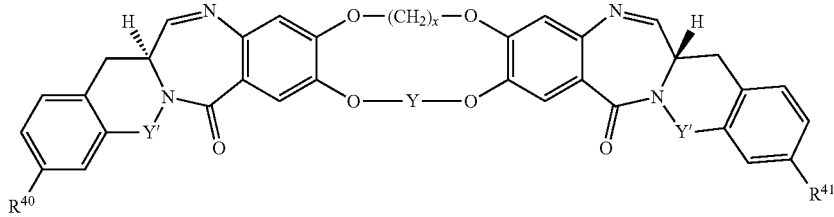

IIb

-continued

TABLE 2

Examples of Dimers According to Formula IIb

| Dimer | x | Y' | Y | $R^{40}$ | $R^{41}$ |
|---|---|---|---|---|---|
| IIb-1 | 3 | $CH_2$ | $(CH_2)_8$ | H | H |
| IIb-2 | 3 | $CH_2$ | $(CH_2)_{10}$ | H | H |
| IIb-3 | 3 | absent | $(CH_2)_{10}$ | H | H |
| IIb-4 | 3 | $CH_2$ | $(CH_2)_2(OCH_2CH_2)_2$ | H | H |
| IIb-5 | 3 | $CH_2$ | $(CH_2)_4NH(CH_2)_4$ | H | H |
| IIb-6 | 3 | $CH_2$ | $(CH_2)_8$ | H | $NH_2$ |
| IIb-7 | 3 | $CH_2$ | $(CH_2)_2(OCH_2CH_2)_2$ | H | $NH_2$ |
| IIb-8 | 3 | $CH_2$ | $(CH_2)_4-N(-CH_2C_6H_4-NH_2)-(CH_2)_4$ | H | H |

TABLE 1

Examples of Dimers According to Formula IIa

| Dimer | x | Y | A | B |
|---|---|---|---|---|
| IIa-1 | 3 | $(CH_2)_7$ | A1 | B1 |
| IIa-2 | 3 | $(CH_2)_8$ | A1 | A1 |
| IIa-3 | 3 | $(CH_2)_9$ | A1 | A1 |
| IIa-4 | 3 | $(CH_2)_{10}$ | A1 | B1 |
| IIa-5 | 3 | $(CH_2)_{11}$ | A1 | A1 |
| IIa-6 | 3 | $(CH_2)_{12}$ | A1 | A1 |
| IIa-7 | 5 | $(CH_2)_{11}$ | A1 | B1 |
| IIa-8 | 5 | $(CH_2)_{12}$ | A1 | A1 |
| IIa-9 | 3 | $(CH_2)_4$-CH=CH-$(CH_2)_4$ | A1 | A1 |
| IIa-10 | 3 | $(CH_2)_4$-CH=CH-$(CH_2)_4$ | A2 | B2 |

In another preferred embodiment, dimers of this invention have a structure represented by formula IIc, where x is 3 or 5 (preferably 3), Y is $(CH_2)_{7-12}$, $(CH_2)_2(OCH_2CH_2)_{1-3}$, $(CH_2)_{2-4}NH(CH_2)_{2-4}$ or $(CH_2)_{2-4}NH((CH_2)_{0-1}phenyl)(CH_2)_{2-4}$ where the phenyl group is optionally substituted with $NH_2$; and $R^{42}$ and $R^{43}$ are independently H, OMe, $NH_2$, $OCH_2CH_2OMe$, $N(CH_2CH_2)O$, $N(CH_2CH_2)NMe$, or $N(CH_2CH_2)NH$. Representative species are listed in Table 3.

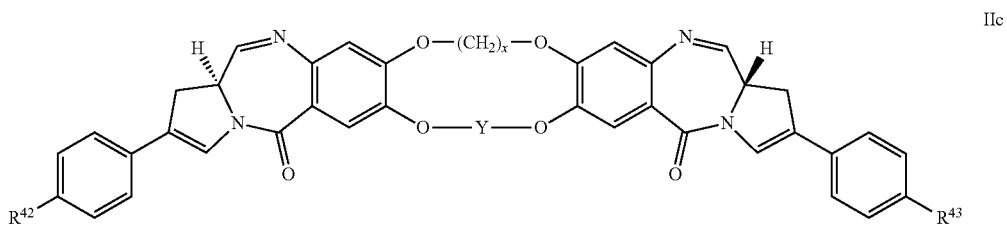

IIc

TABLE 3

Examples of Dimers According to Formula IIc

| Dimer | x | Y | R42 | R43 |
|---|---|---|---|---|
| IIc-1 | 3 | (CH2)10 | H | H |
| IIc-2 | 3 | (CH2)12 | OMe | OMe |
| IIc-3 | 3 | (CH2)12 | OCH2CH2OMe | OCH2CH2OMe |
| IIc-4 | 3 | (CH2)12 | ⸻N(morpholine) | ⸻N(morpholine) |
| IIc-5 | 3 | (CH2)12 | ⸻N(piperazine-NMe) | ⸻N(piperazine-NMe) |
| IIc-6 | 3 | (CH2)2(OCH2CH2)2 | H | H |
| IIc-7 | 3 | (CH2)8 | OMe | OMe |
| IIc-8 | 3 | (CH2)8 | ⸻N(piperazine-NMe) | ⸻N(piperazine-NMe) |
| IIc-9 | 3 | (CH2)8 | ⸻N(piperazine-NMe) | ⸻N(piperazine-NH) |
| IIc-10 | 3 | (CH2)8 | ⸻N(piperazine-NMe) | NH2 |
| IIc-11 | 3 | (CH2)8 | NH2 | OMe |

Preferably, dimers of this invention are selected from the group consisting of dimer IIb-6, IIc-8, IIc-9, IIc-10, IIc-11, IId-1, IId-2, and IId-3:

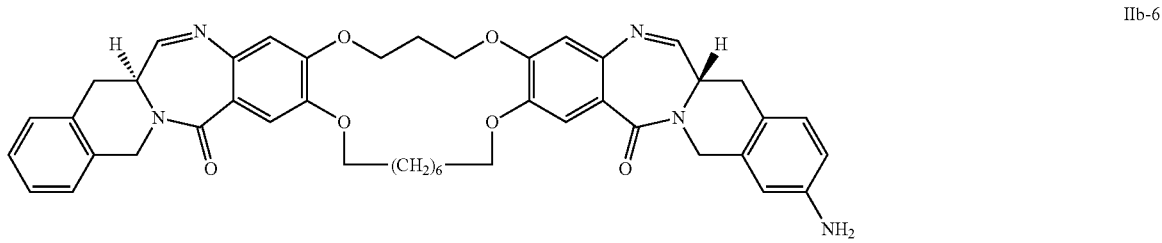

IIb-6

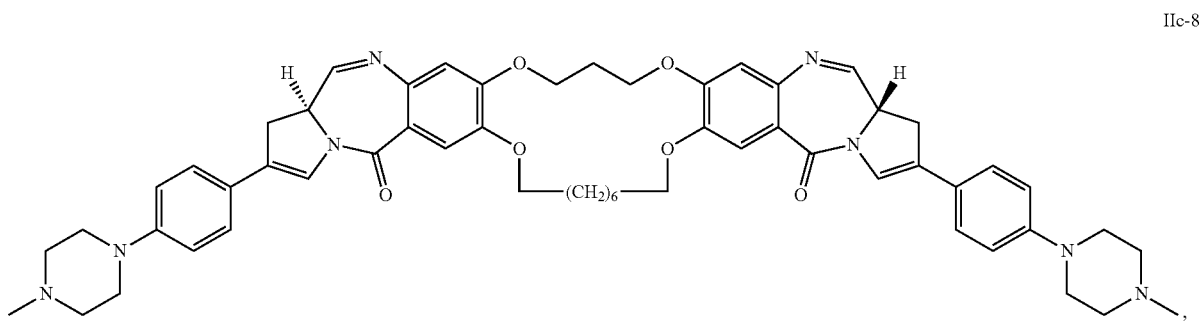

IIc-8

-continued
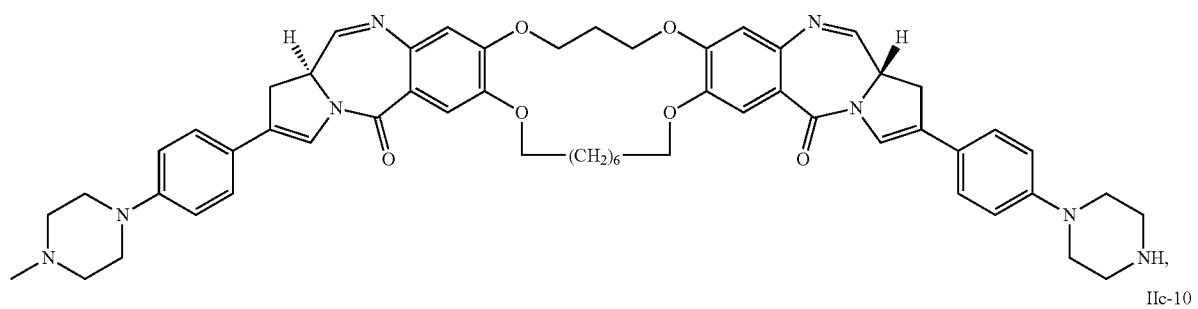
IIc-9
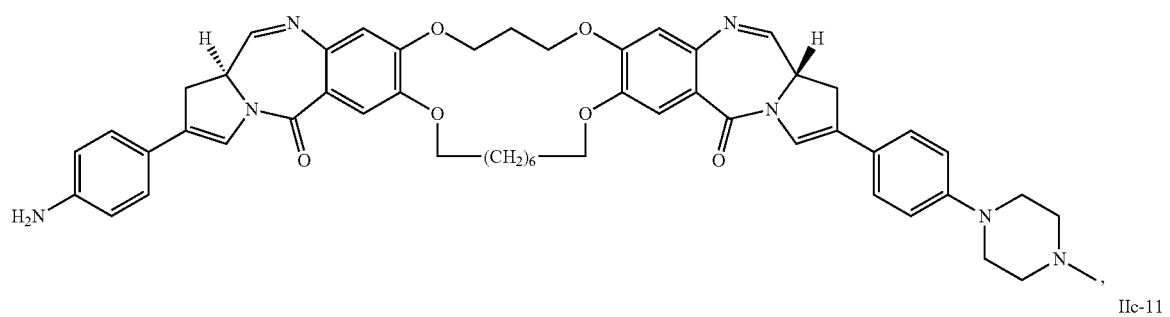
IIc-10
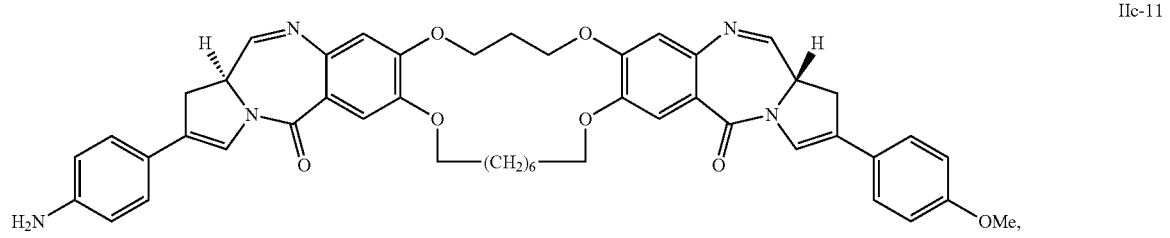
IIc-11
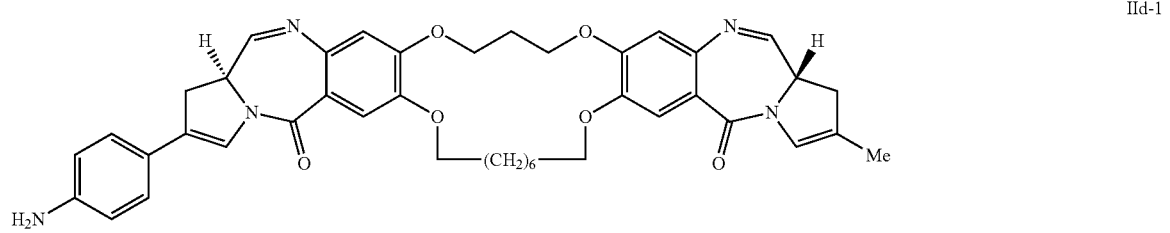
IId-1
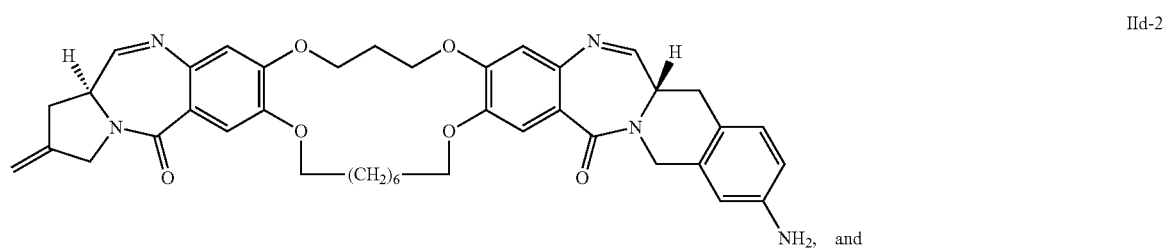
IId-2
and
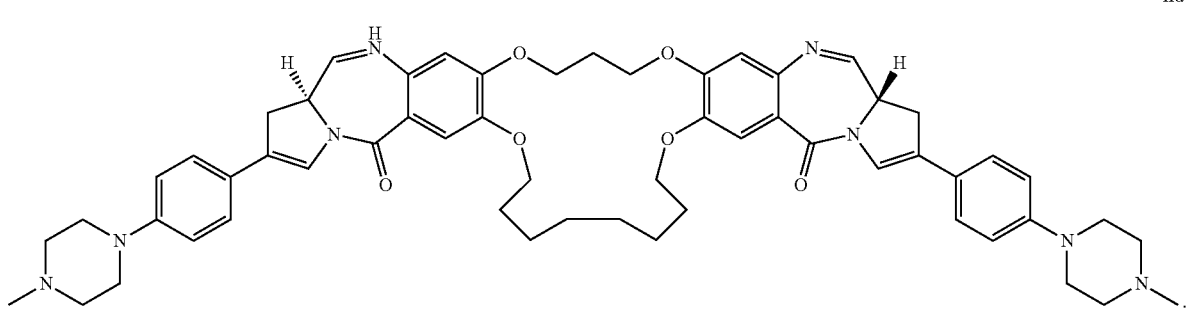
IId-3

Conjugates
General

Dimers of this invention can be used as therapeutic agents per se, but preferably are used as conjugates with a targeting moiety that specifically or preferentially binds to a chemical entity on a cancer cell. Preferably, the targeting moiety is an antibody or antigen binding portion thereof and the chemical entity is a tumor associated antigen.

Thus, another embodiment of this invention is a conjugate comprising dimer of this invention and a ligand, represented by formula (II)

$$[D(X^D)_a(C)_c(X^Z)_b]_m Z \qquad (II)$$

where Z is a ligand, D is a dimer of this invention, and $-(X^D)_a C(X^Z)_b-$ are collectively referred to as a "linker moiety" or "linker" because they link Z and D. Within the linker, C is a cleavable group designed to be cleaved at or near the site of intended biological action of dimer D; $X^D$ and $X^Z$ are referred to as spacer moieties (or "spacers") because they space apart D and C and C and Z, respectively; subscripts a, b, and c are independently 0 or 1 (that is, the presence of $X^D$, $X^Z$ and C are optional). Subscript m is 1, 2, 3, 4, 5, 6, 7, 8, 9, or 10 (preferably 1, 2, 3, or 4). D, $X^D$, C, $X^Z$ and Z are more fully described hereinbelow.

Ligand Z—for example an antibody—performs a targeting function. By binding to a target tissue or cell where its antigen or receptor is located, ligand Z directs the conjugate there. (When ligand Z is an antibody, the conjugate is sometimes referred to as antibody-drug conjugate (ADC) or an immunoconjugate. Preferably, the target tissue or cell is a cancer tissue or cell and the antigen or receptor is a tumor-associated antigen, that is, an antigen that is uniquely expressed by cancerous cells or is overexpressed by cancer cells, compared to non-cancerous cells. Cleavage of group C at the target tissue or cell releases dimer D to exert its cytotoxic effect locally. In some instances, the conjugate is internalized into a target cell by endocytosis and cleavage takes place within the target cell. In this manner, precise delivery of dimer D is achieved at the site of intended action, reducing the dosage needed. Also, dimer D is normally biologically inactive (or significantly less active) in its conjugated state, thereby reducing undesired toxicity against non-target tissue or cells. As anticancer drugs are often highly toxic to cells in general, this is an important consideration.

As reflected by the subscript m, each molecule of ligand Z can conjugate with more than one dimer D, depending on the number of sites ligand Z has available for conjugation and the experimental conditions employed. Those skilled in the art will appreciate that, while each individual molecule of ligand Z is conjugated to an integer number of dimers D, a preparation of the conjugate may analyze for a non-integer ratio of dimers D to ligand Z, reflecting a statistical average. This ratio is referred to as the substitution ratio (SR) or, synonymously, the drug-antibody ratio (DAR).

Ligand Z

Preferably, ligand Z is an antibody. For convenience and brevity and not by way of limitation, the detailed subsequent discussion herein about the conjugation of ligand Z is written in the context of its being an antibody, but those skilled in the art will understand that other types of ligand Z can be conjugated, mutatis mutandis. For example, conjugates with folic acid as the ligand can target cells having the folate receptor on their surfaces (Leamon et al., Cancer Res. 2008, 68 (23), 9839). For the same reason, the detailed discussion below is primarily written in terms of a 1:1 ratio of antibody Z to analog D (m=1).

Preferably, ligand Z is an antibody against a tumor associated antigen, allowing the selective targeting of cancer cells. Examples of such antigens include: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., U.S. Pat. No. 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Vistica et al., U.S. Pat. No. 8,383,118 B2 (2013, fucosyl-GM1, in particular antibodies 5B1, 5B1a, 7D4, 7E4, 13B8, and 18D5) Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA; in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Terrett et al., U.S. Pat. No. 8,680,247 B2 (2014; glypican-3; in particular antibodies 4A6, 11E7, and 16D10); Harkins et al., U.S. Pat. No. 7,335,748 B2(2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Each of the aforementioned antibodies can be used in an ADC with d dimer of this invention.

Ligand Z can also be an antibody fragment or antibody mimetic, such as an affibody, a domain antibody (dAb), a nanobody, a unibody, a DARPin, an anticalin, a versabody, a duocalin, a lipocalin, or an avimer.

Any one of several different reactive groups on ligand Z can be a conjugation site, including $\epsilon$-amino groups in lysine residues, pendant carbohydrate moieties, carboxylic acid groups, disulfide groups, and thiol groups. Each type of reactive group represents a trade-off, having some advantages and some disadvantages. For reviews on antibody reactive groups suitable for conjugation, see, e.g., Garnett, *Adv. Drug Delivery Rev.* 53 (2001), 171-216 and Dubowchik and Walker, *Pharmacology & Therapeutics* 83 (1999), 67-123, the disclosures of which are incorporated herein by reference.

In one embodiment, ligand Z is conjugated via a lysine ε-amino group. Most antibodies have multiple lysine ε-amino groups, which can be conjugated via amide, urea, thiourea, or carbamate bonds using techniques known in the art. However, it is difficult to control which and how many ε-amino groups react, leading to potential batch-to-batch variability in conjugate preparations. Also, conjugation may cause neutralization of a protonated ε-amino group important for maintaining the antibody's native conformation or may take place at a lysine near or at the antigen binding site, neither being a desirable occurrence.

In another embodiment, ligand Z can be conjugated via a carbohydrate side chain, as many antibodies are glycosylated. The carbohydrate side chain can be oxidized with periodate to generate aldehyde groups, which in turn can be reacted with amines to form an imine group, such as in a semicarbazone, oxime, or hydrazone. If desired, the imine group can be converted to a more stable amine group by reduction with sodium cyanoborohydride. For additional disclosures on conjugation via carbohydrate side chains, see, e.g., Rodwell et al., *Proc. Nat'l Acad. Sci. USA* 83, 2632-2636 (1986); the disclosure of which is incorporated herein by reference. As with lysine ε-amino groups, there are concerns regarding reproducibility of the location of the conjugation site(s) and stoichiometry.

In yet another embodiment, ligand Z can be conjugated via a carboxylic acid group. In one embodiment, a terminal carboxylic acid group is functionalized to generate a carbohydrazide, which is then reacted with an aldehyde-bearing conjugation moiety. See Fisch et al., *Bioconjugate Chemistry* 1992, 3, 147-153.

In yet another embodiment, antibody Z can be conjugated via a disulfide group bridging a cysteine residue on antibody Z and a sulfur on the other portion of the conjugate. Some antibodies lack free thiol (sulfhydryl) groups but have disulfide groups, for example in the hinge region. In such case, free thiol groups can be generated by reduction of native disulfide groups. The thiol groups so generated can then be used for conjugation. See, e.g., Packard et al., *Biochemistry* 1986, 25, 3548-3552; King et al., *Cancer Res.* 54, 6176-6185 (1994); and Doronina et al., *Nature Biotechnol.* 21(7), 778-784 (2003); the disclosures of which are incorporated herein by reference. Again, there are concerns regarding conjugation site location and stoichiometry and the possible disruption of antibody native conformation.

A number of methods are known for introducing free thiol groups into antibodies without breaking native disulfide bonds, which methods can be practiced with a ligand Z of this invention. Depending on the method employed, it may be possible to introduce a predictable number of free sulfhydryls at predetermined locations. In one approach, mutated antibodies are prepared in which a cysteine is substituted for another amino acid. See, for example, Eigenbrot et al., U.S. Pat. No. 7,521,541 B2 (2009); Chilkoti et al., *Bioconjugate Chem.* 1994, 5, 504-507; Urnovitz et al., U.S. Pat. No. 4,698,420 (1987); Stimmel et al., *J. Biol. Chem.*, 275 (39), 30445-30450 (2000); Bam et al., U.S. Pat. No. 7,311,902 B2 (2007); Kuan et al., *J. Biol. Chem.*, 269 (10), 7610-7618 (1994); Poon et al., *J. Biol. Chem.*, 270 (15), 8571-8577 (1995). In another approach, an extra cysteine is added to the C-terminus. See, e.g. Cumber et al., *J. Immunol.*, 149, 120-126 (1992); King et al, *Cancer Res.*, 54, 6176-6185 (1994); Li et al., *Bioconjugate Chem.*, 13, 985-995 (2002); Yang et al., *Protein Engineering*, 16, 761-770 (2003); and Olafson et al., *Protein Engineering Design & Selection*, 17, 21-27 (2004). A preferred method for introducing free cysteines is that taught by Liu et al., WO 2009/026274 A1, in which a cysteine bearing amino acid sequence is added to the C-terminus of the heavy chain of an antibody. This method introduces a known number of cysteine residues (one per heavy chain) at a known location away from the antigen binding site. The disclosures of the documents cited in this paragraph are all incorporated herein by reference.

In yet another embodiment, lysine ε-amino groups can be modified with reagents such as 2-iminothiolane or N-succinimidyl-3-(2-pyridyldithio)propionate (SPDP), converting an ε-amino group into a thiol or disulfide group—creating a cysteine surrogate, as it were. However, this method suffers from the same conjugation location and stoichiometry limitations associated with ε-amino groups proper.

Linker Components

As noted above, the linker portion of a conjugate of this invention comprises up to three elements: a cleavable group C and optional spacers $X^Z$ and $X^D$.

Cleavable group C is a group cleavable under physiological conditions, preferably selected such that it is relatively stable while the conjugate is in general circulation in the blood plasma, but is readily cleaved once the conjugate reaches its site of intended action, that is, near, at, or within the target cell. Preferably, the conjugate is internalized by a target cell upon binding of antibody Z to an antigen displayed on the surface of the target cell. Subsequently, cleavage of group C occurs in a vesicular body of the target cell (an early endosome, a late endosome, or, especially, a lysosome).

In one embodiment, group C is a pH sensitive group. The pH in blood plasma is slightly above neutral, while the pH inside a lysosome is acidic, circa 5. Thus, a group C whose cleavage is acid catalyzed will cleave at a rate several orders of magnitude faster inside a lysosome than in the blood plasma rate. Examples of suitable acid-sensitive groups include cis-aconityl amides and hydrazones, as described in Shen et al., U.S. Pat. No. 4,631,190 (1986); Shen et al., U.S. Pat. No. 5,144,011 (1992); Shen et al., *Biochem. Biophys. Res. Commun.* 102, 1048-1054 (1981) and Yang et al., *Proc. Natl Acad. Sci* (USA), 85, 1189-1193 (1988); the disclosures of which are incorporated herein by reference.

In another embodiment, group C is a disulfide. Disulfides can be cleaved by a thiol-disulfide exchange mechanism, at a rate dependent on the ambient thiol concentration. As the intracellular concentration of glutathione and other thiols is higher than their serum concentrations, the cleavage rate of a disulfide will be higher intracellularly. Further, the rate of thiol-disulfide exchange can be modulated by adjustment of the steric and electronic characteristics of the disulfide (e.g., an alkyl-aryl disulfide versus an alkyl-alkyl disulfide; substitution on the aryl ring, etc.), enabling the design of disulfide linkages that have enhanced serum stability or a particular cleavage rate. For additional disclosures relating to disulfide cleavable groups in conjugates, see, e.g., Thorpe et al., *Cancer Res.* 48, 6396-6403 (1988); Santi et al., U.S. Pat. No. 7,541,530 B2 (2009); Ng et al., U.S. Pat. No. 6,989,452 B2 (2006); Ng et al., WO 2002/096910 A1; Boyd et al., U.S. Pat. No. 7,691,962 B2; and Sufi et al., US 2010/0145036 A1; the disclosures of which are incorporated herein by reference.

A preferred cleavable group is a peptide that is cleaved selectively by a protease inside the target cell, as opposed to by a protease in the serum. Typically, a cleavable peptide group comprises from 1 to 20 amino acids, preferably from 1 to 6 amino acids, more preferably from 1 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this context, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, group C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); and Bouvier et al. *Meth. Enzymol.* 248: 614 (1995); the disclosures of which are incorporated herein by reference.

For conjugates that are not intended to be internalized by a cell, a group C can be chosen such that it is cleaved by a protease present in the extracellular matrix in the vicinity of the target tissue, e.g., a protease released by nearby dying cells or a tumor-associated protease. Exemplary extracellular tumor-associated proteases are matrix metalloproteases (MMP), thimet oligopeptidase (TOP) and CD10.

For conjugates that are designed to be internalized by a cell, group C preferably comprises an amino acid sequence selected for cleavage by an endosomal or lysosomal protease, especially the latter. Non-limiting examples of such proteases include cathepsins B, C, D, H, L and S, especially cathepsin B. Cathepsin B preferentially cleaves peptides at a sequence -$AA^2$-$AA^1$- where $AA^1$ is a basic or strongly hydrogen bonding amino acid (such as lysine, arginine, or citrulline) and $AA^2$ is a hydrophobic amino acid (such as phenylalanine, valine, alanine, leucine, or isoleucine), for example Val-Cit (where Cit denotes citrulline) or Val-Lys. (Herein, amino acid sequences are written in the N-to-C direction, as in $H_2N$-$AA^2$-$AA^1$-$CO_2H$, unless the context clearly indicates otherwise.) Lys-Val-Ala, Asp-Val-Ala, Val-Ala, Lys-Val-Cit, and Asp-Val-Cit are also substrate peptide motifs for cathpsin B, although in some instances the cleavage rate may be slower. For additional information regarding cathepsin-cleavable groups, see Dubowchik et al., *Biorg. Med. Chem. Lett.* 8, 3341-3346 (1998); Dubowchik et al., *Bioorg. Med. Chem. Lett.,* 8 3347-3352 (1998); and Dubowchik et al., *Bioconjugate Chem.* 13, 855-869 (2002); the disclosures of which are incorporated by reference. Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-$AA^1$- wherein $AA^1$ is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu.

The preparation and design of cleavable groups C consisting of a single amino acid is disclosed in Chen et al., U.S. Pat. No. 8,664,407 B2 (2014), the disclosure of which is incorporated herein by reference.

Group C can also be a photocleavable one, for example a nitrobenzyl ether that is cleaved upon exposure to light.

Group C can be bonded directly to antibody Z or analog D; i.e. spacers $X^Z$ and $X^D$, as the case may be, can be absent. For example, if group C is a disulfide, one of the two sulfurs can be a cysteine residue or its surrogate on antibody Z. Or, group C can be a hydrazone bonded to an aldehyde on a carbohydrate side chain of the antibody. Or, group C can be a peptide bond formed with a lysine ε-amino group of antibody Z. In a preferred embodiment, dimer D is directly bonded to group C via a peptidyl bond to a carboxyl or amine group in dimer D.

When present, spacer $X^Z$ provides spatial separation between group C and antibody Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

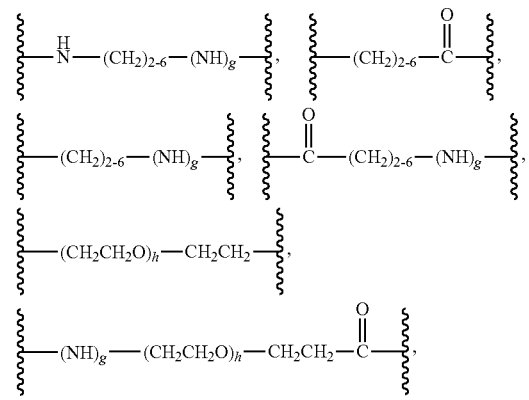

and combinations thereof,
where the subscript g is 0 or 1 and the subscript h is 1 to 24, preferably 2 to 4. These segments can be combined, such as illustrated below:

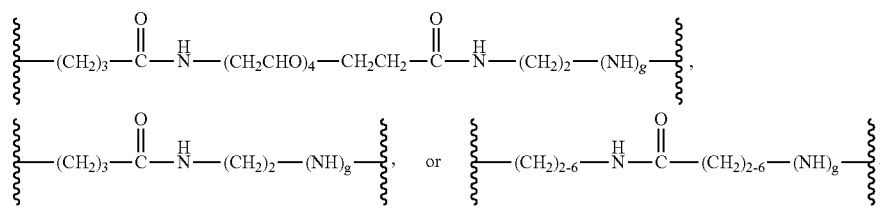

Spacer $X^D$, if present, provides spatial separation between group C and dimer D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, as described above in the context of spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain poly(ethylene glycol) (PEG) groups, which enhance solubility either during the performance the conjugation chemistry or in the final ADC product. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to group C and either antibody Z or dimer D and (2) has a structure such that cleavage from group C initiates a reaction sequence resulting in the self-immolating moiety disbonding itself from antibody Z or dimer D, as the case may be. In other words, reaction at a site distal from antibody Z or dimer D (cleavage from group C) causes the $X^Z$—Z or the $X^D$-D bond to rupture as well. The presence of a self-immolating moiety is desirable in the case of spacer $X^D$ because, if, after cleavage of the conjugate, spacer $X^D$ or a portion thereof were to remain attached to dimer D, the biological activity of the latter may be impaired. The use of a self-immolating moiety is especially desirable where cleavable group C is a polypeptide, in which instance the self-immolating moiety typically is located adjacent thereto.

Exemplary self-immolating moieties (i)-(v) bonded to a hydroxyl or amino group on a partner molecule D are shown below:

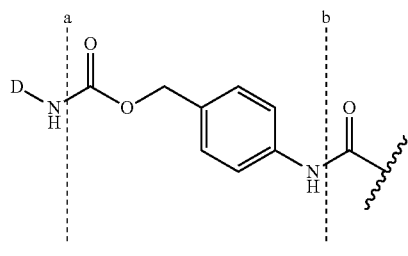

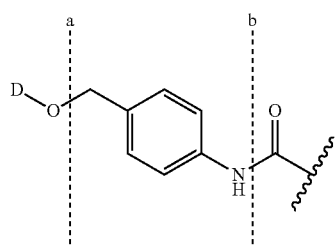

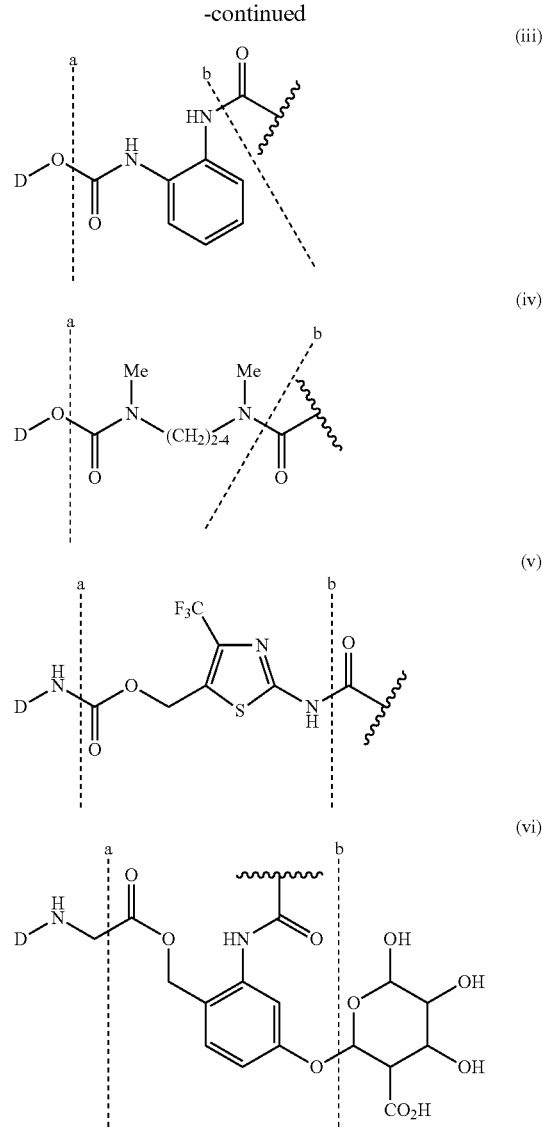

The self-immolating moiety is the structure between dotted lines a and b, with adjacent structural features shown to provide context. Self-immolating moieties (i) and (v) are bonded to a dimer $D-NH_2$ (i.e., dimer D is conjugated via an amino group), while self-immolating moieties (ii), (iii), and (iv) are bonded to a dimer D-OH (i.e., dimer D is conjugated via a hydroxyl or carboxyl group). Cleavage of the amide bond at dotted line b (e.g., by a peptidase) releases the amide nitrogen as an amine nitrogen, initiating a reaction sequence that results in the cleavage of the bond at dotted line a and the consequent release of D-OH or $D-NH_2$, as the case may be. Alternatively, the cleavage that triggers the self-immolating reaction can be by a different type of enzyme, for example by a β-glucuronidase, as in the instance of structure (vi). For additional disclosures regarding self-immolating moieties, see Carl et al., *J. Med. Chem.*, 24 (3), 479-480 (1981); Carl et al., WO 81/01145 (1981); Dubowchik et al., *Pharmacology & Therapeutics*, 83, 67-123 (1999); Firestone et al., U.S. Pat. No. 6,214,345 B1 (2001); Toki et al., *J. Org. Chem.* 67, 1866-1872 (2002); Doronina et al., *Nature Biotechnology* 21 (7), 778-784 (2003) (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference. A preferred self-immolating group is p-aminobenzyl oxycarbonyl (PABC) group, as shown in structure (i).

In another embodiment, an antibody targeting moiety and the dimer D are linked by a non-cleavable linker, i.e., element C is absent. Degradation of the antibody eventually reduces the linker to a small appended moiety that does not interfere with the biological activity of dimer D.

Conjugation Techniques

Conjugates of this invention preferably are made by first preparing a compound comprising an analog of this invention (represented by D in the formulae below) and linker $(X^D)_a(C)_c(X^Z)_b$ (where $X^D$, C, $X^Z$, a, b, and c are as defined for formula (II)) to form an analog-linker composition represented by formula (III):

  (III)

where $R^{31}$ is a functional group suitable for reacting with a complementary functional group on antibody Z to form the conjugate. Examples of suitable groups $R^{31}$ include amino, azide, cyclooctyne,

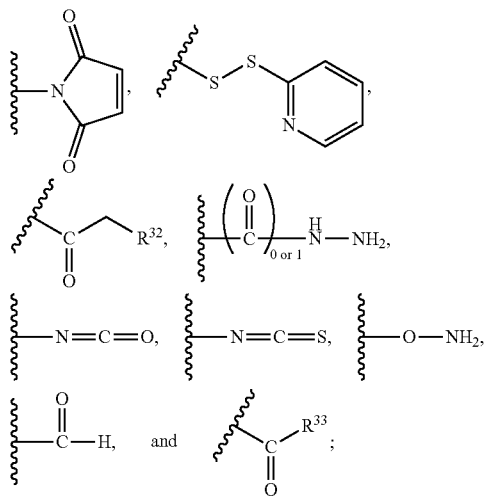

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D-(X^D)_aC(X^Z)_bR^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847,105 B2 (2010); Gangwar et al., U.S. Pat. No. 7,968,586 B2 (2011); Sufi et al., US 2010/0145036 A1; and Chen et al., US 2010/0113476 A1; the disclosures of which are incorporated herein by reference.

Preferably reactive functional group —$R^{31}$ is —NH$_2$, —OH, —CO$_2$H, —SH, maleimido, cyclooctyne, azido (—N$_3$), hydroxylamino (—ONH$_2$) or N-hydroxysuccinimido. Especially preferred functional groups —$R^{31}$ are:

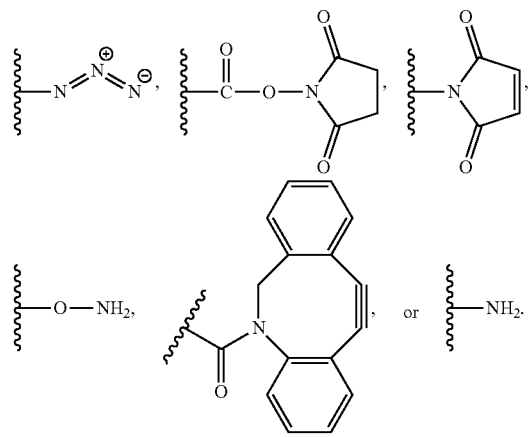

An —OH group can be esterified with a carboxy group on the antibody, for example, on an aspartic or glutamic acid side chain.

A —CO$_2$H group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Various techniques can be introducing an —SH group into an antibody. In a preferred one, an ε-amino group in the side chain of a lysine residue in the antibody is reacted with 2-iminothiolane to introduce a free thiol (—SH) group. The thiol group can react with a maleimide or other nucleophile acceptor group to effect conjugation:

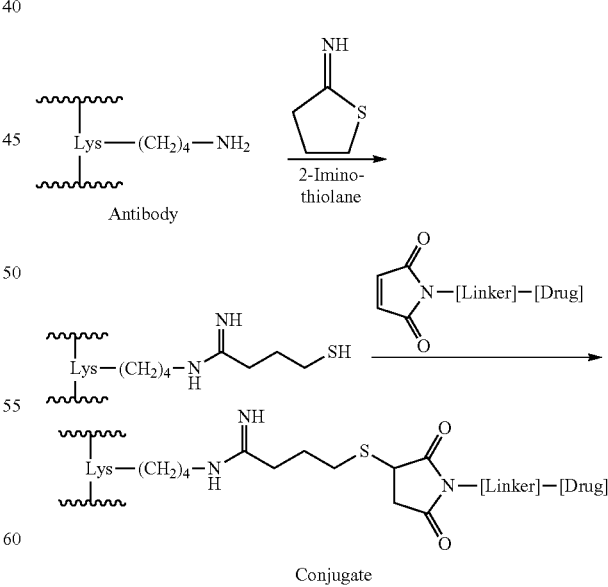

Typically, a thiolation level of two to three thiols per antibody is achieved. For a representative procedure, see Cong et al. 2014, the disclosure of which is incorporated herein by reference. Thus, in one embodiment, an antibody for conjugation to a dimer of this invention has one or more lysine residues (preferably two or three) modified by reaction with iminothiolane.

An —SH group can also be used for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

An alternative conjugation technique employs copper-free "click chemistry," in which an azide group adds across the strained alkyne bond of a cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

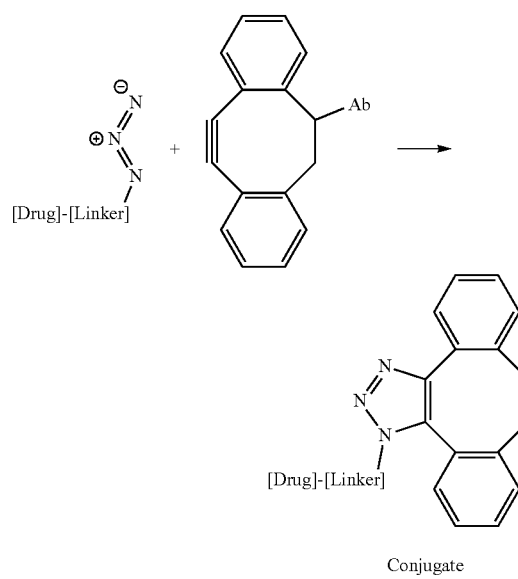

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate with a dimer of this invention has one or more amino acids replaced by a non-natural amino acid, which preferably is p-acetylphenylalanine or p-azidophenylalanine, more preferably p-acetylphenylalanine.

Still another conjugation technique uses the enzyme transglutaminase (preferably bacterial transglutaminase or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the C-amino group of a lysine or a 5-amino-n-pentyl group. In a typical conjugation reaction, the glutamine residue is located on the antibody, while the alkyleneamino group is located on the linker-drug moiety, as shown below:

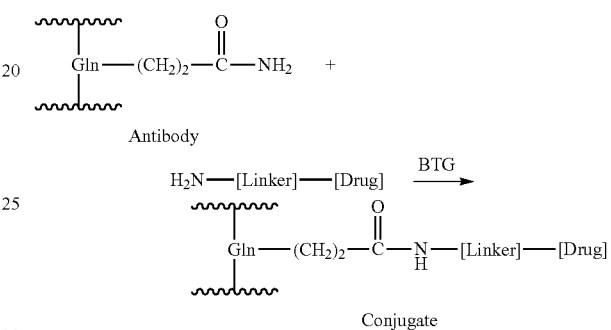

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297)—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution in an antibody not only eliminates glycosylation, but also introduces a second glutamine residue (at position 297) that too is an amine acceptor. Thus, in one embodiment, an antibody that is conjugated to a dimer of this invention is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

An antibody also can be adapted for conjugation by modifying its glycosyl group to introduce a keto group that serves as a conjugation site by oxime formation, as taught by Zhu et al., *mAbs* 2014, 6, 1. In another glycoengineering variation, an antibody's glycosyl group can be modified to introduce an azide group for conjugation by "click chemistry." See Huang et al., *J. Am. Chem. Soc.* 2012, 134, 12308 and Wang, U.S. Pat. No. 8,900,826 B2 (2014) and U.S. Pat. No. 7,807,405 B2 (2010).

Yet another conjugation technique can be generally referred to as disulfide bridging: the disulfide bonds in an antibody are cleaved, creating a pair of thiol (—SH) groups. The antibody is then treated with a drug-linker compound that contains two thiol-reactive sites. Reaction of the thiol groups with the two sites effects a re-bridging that re-creates, in a fashion, the original disulfide bridge, thus preserving the antibody tertiary structure and attaching a drug-linker moiety. See, e.g., Burt et al., WO 2013/190292 A2 (2013) and Jackson et al., US 2013/0224228 A1 (2013).

Dimer-Linker Compounds

Generally, an ADC of a dimer of this invention comprises a linker attached to a functional group on the dimer, which linker is attached to the antibody. Reflecting the diversity of conjugation techniques available, the dimers of this invention can be elaborated into many different dimer-linker compounds suitable for conjugation to an antibody.

Generally, there are three different modes for attachment of the linker to a dimer of this invention, as illustrated in the figure below (which is a simplified version of formula I with some variables not shown for simplicity):

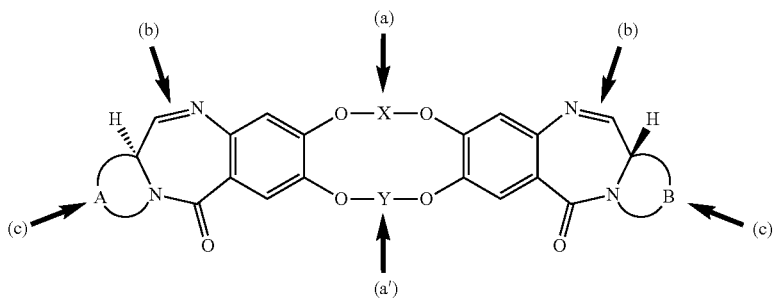

In type (a) and (a') dimer-linker compounds, a functional group for attachment of the linker is located in the bridge X or Y between the two dimer halves. In type (b) dimer-linker compounds, the linker is attached as an addition product across an imine double bond. In type (c) dimer-linker compounds, a functional group for attachment of the linker is located at either A or B.

A preferred dimer-linker compound has a structure according to formula III:

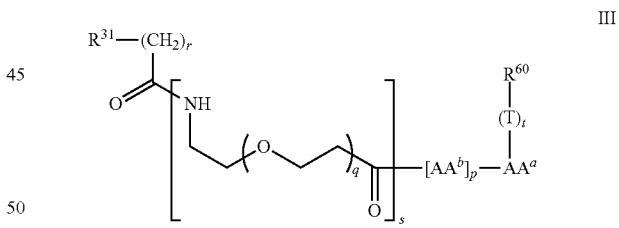

wherein
$R^{60}$ is according to formula IIIa, IIIa', or IIIa"

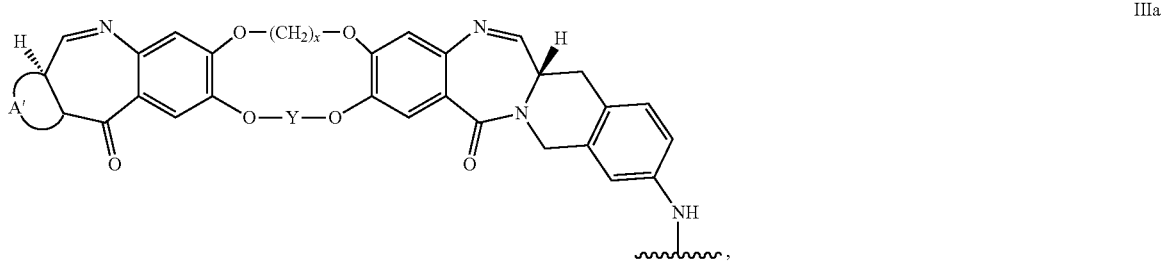

-continued

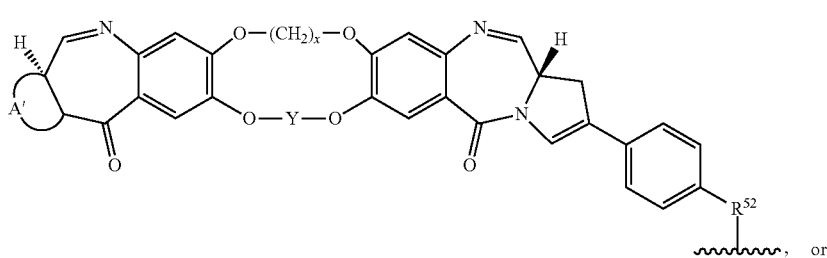
IIIa'

, or

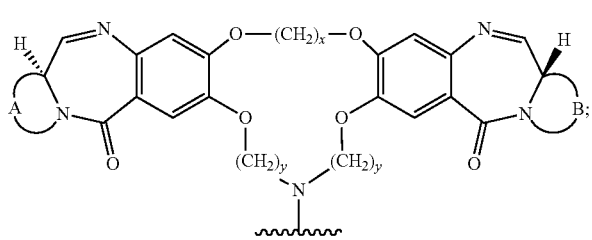
IIIa"

Y is $(CH_2)_{6-10}$ (preferably $(CH_2)_8$);
x is 3 or 5 (preferably 3);
each y is independently 2, 3, or 4 (preferably both are 4);
A and B are independently according to formula Ia or Ib

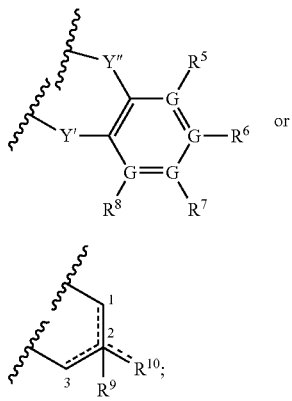

Ia

Ib wherein, in formula Ia
Y' and Y" are independently absent, $CH_2$, $C=O$, or $CHR^{12}$; wherein each $R^{12}$ is independently F, Cl, Br, or $C_1-C_3$ alkyl, with the proviso that Y' and Y" are not both absent;
each G is independently C or N, with the proviso that no more than two Gs are N; and
each $R^5$, $R^6$, $R^7$, and $R^8$ is independently H, Cl, Br, $C_{1-3}$ alkyl, $NO_2$, CN, $NH_2$, $O(C_{1-3}$ alkyl), or $(OCH_2CH_2)_{1-2}O(C_{1-3}$ alkyl) (preferably H);
or where a $R^5$, $R^6$, $R^7$, or $R^8$ is attached to—i.e., is associated with—a G that is N, such $R^5$, $R^6$, $R^7$, or $R^8$ is absent;
and
wherein, in formula Ib,
the dotted lines indicate the optional presence of a C1-C2, C2-C3, or C2-$R^{10}$ double bond;

$R^9$ is absent if a C1-C2, C2-C3, or C2-$R^{10}$ double bond is present and otherwise is H;
$R^{10}$ is H, Cl, Br, $=CH_2$, $=CH(C_{1-5}$ alkyl), $C_{1-3}$ alkyl, $NO_2$, CN, or $NH_2$ (preferably H);
A' is

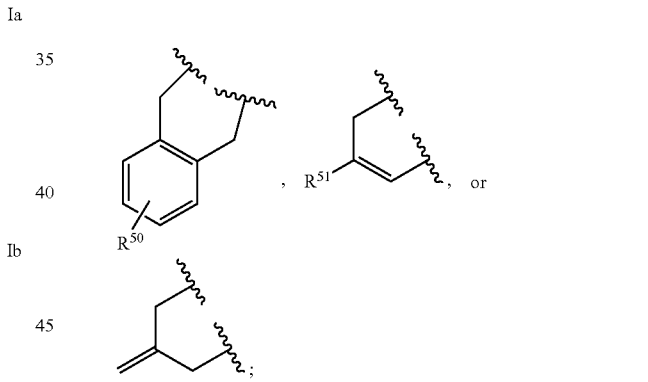

$R^{50}$ is H, Cl, Br, $C_{1-3}$ alkyl, $NO_2$, CN, $NH_2$, $O(C_{1-3}$ alkyl), or $(OCH_2CH_2)_{1-2}O(C_{1-3}$ alkyl) (preferably H);
$R^{51}$ is H, Cl, Br, $C_{1-3}$ alkyl, $NO_2$, CN, or $NH_2$ (preferably H);
T is a self-immolating group;
t is 0 or 1;
$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 1, 2, 3, 4, 5, 6, 7, 8, 9, or 10 (preferably 2, 3, 4, or 8);
r is 1, 2, 3, 4, or 5 (preferably 2, 3, 4, or 5);
s is 0 or 1; and $R^{31}$ is

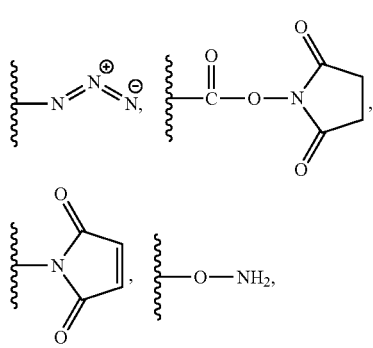

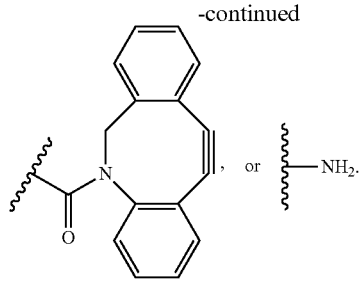

In a preferred dimer-linker compound according to formula III, $R^{60}$ is IIIa, corresponding to a dimer-linker of the following structure:

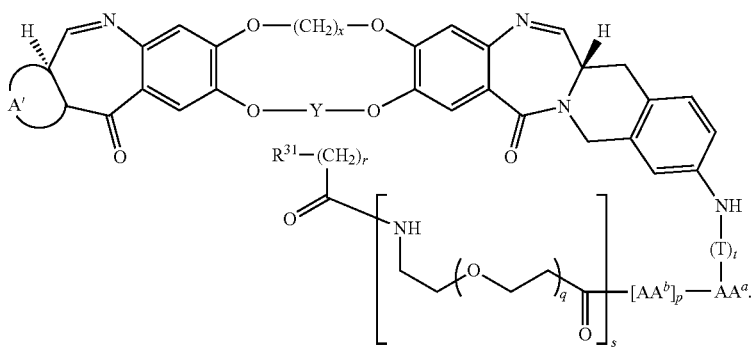

In another preferred dimer-linker compound according to formula III, $R^{60}$ is IIIa', corresponding to a dimer-linker of the following structure:

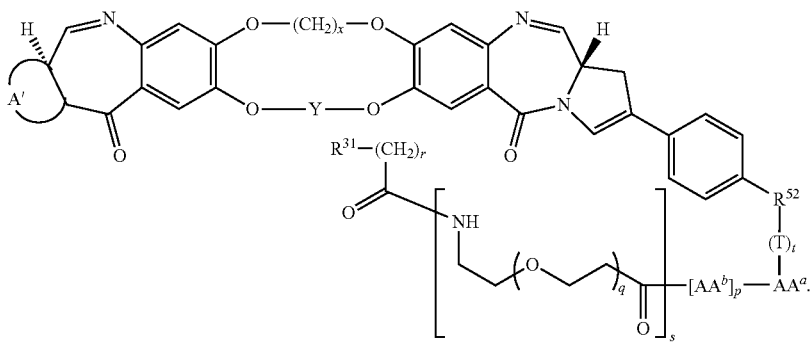

In yet another preferred dimer-linker compound according to formula III, $R^{60}$ is IIIa", corresponding to a dimer-linker of the following structure:

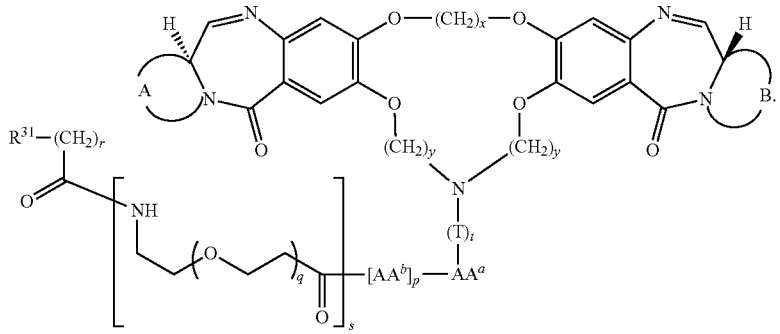

R³¹ in formula III is a reactive functional group capable of reacting with a complementary functional group on the antibody to effect conjugation, as described above.

In formula III, -AAᵃ-[AAᵇ]ₚ- represents a polypeptide whose length is determined by the value of p (dipeptide if p is 1, tetrapeptide if p is 3, etc.). AAᵃ is at the carboxy terminus of the polypeptide and its carboxyl group forms a peptide (amide) bond with an amine nitrogen of the dimer. Conversely, the last AAᵇ is at the amino terminus of the polypeptide and its α-amino group forms a peptide bond with

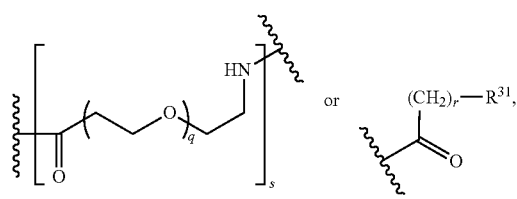 or 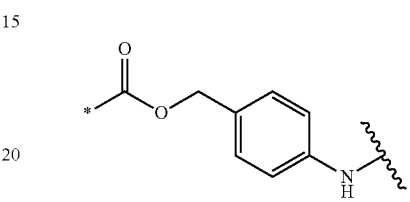

depending on whether s is 1 or 0, respectively. Preferred polypeptides -AAᵃ-[AAᵇ]ₚ- are Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit, written in the conventional N-to-C direction, as in H₂N-Val-Cit-CO₂H). More preferably, the polypeptide is Val-Cit, Val-Lys, or Val-Ala. Preferably, a polypeptide -AAᵃ-[AAᵇ]ₚ- is cleavable by an enzyme found inside the target (cancer) cell, for example a cathepsin and especially cathepsin B.

As indicated by the subscript t equals 0 or 1, a self-immolating group T is optionally present in dimer-linker compounds of formula III. When present, the self-immolating group T preferably is a p-aminobenzyl oxycarbonyl (PABC) group, whose structure is shown below, with an asterisk (*) denoting the end of the PABC bonded to an amine nitrogen of the dimer and a wavy line (~~~) denoting the end bonded to the polypeptide -AAᵃ-[AAᵇ]ₚ-.

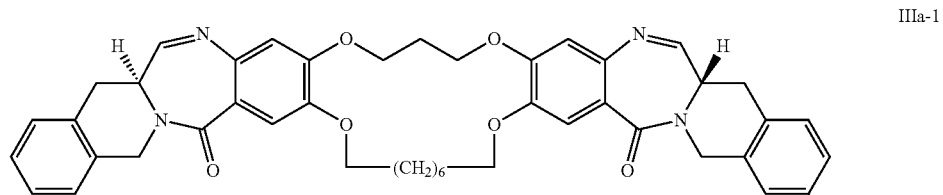

Preferred dimer linker compounds are selected from the group having structures represented by formulae IIIa-1, IIIa-3, IIIa-4, IIIa-5, IIIa-6, and IIIa-7.

IIIa-1

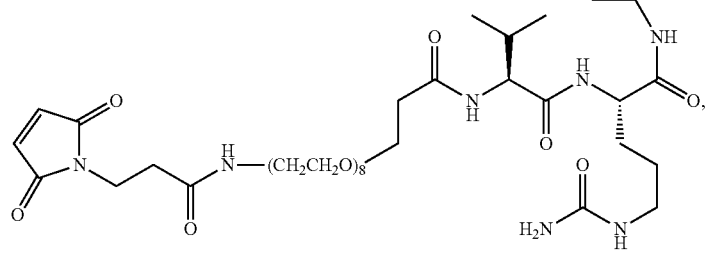

IIIa-2

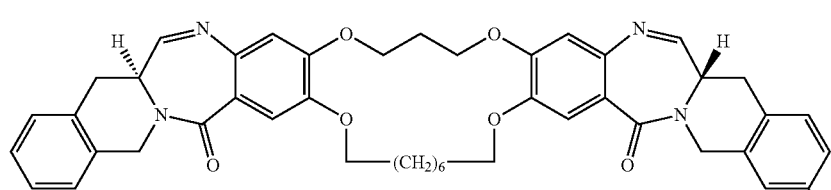

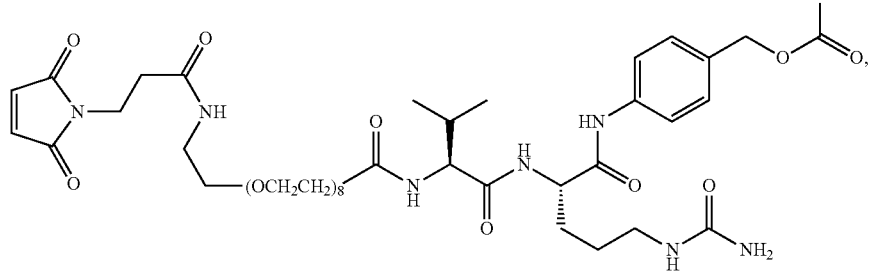

-continued
IIIa-3
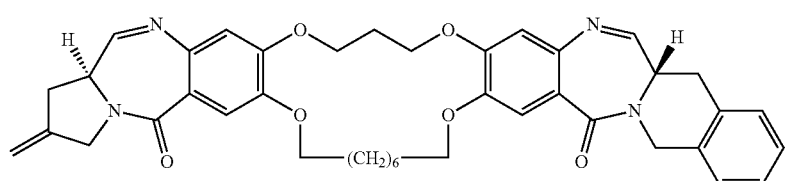
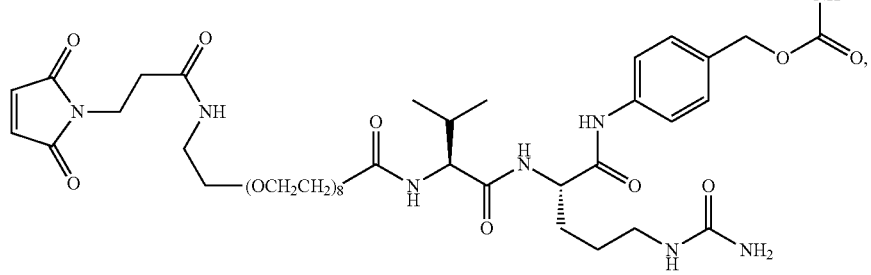
IIIa-4
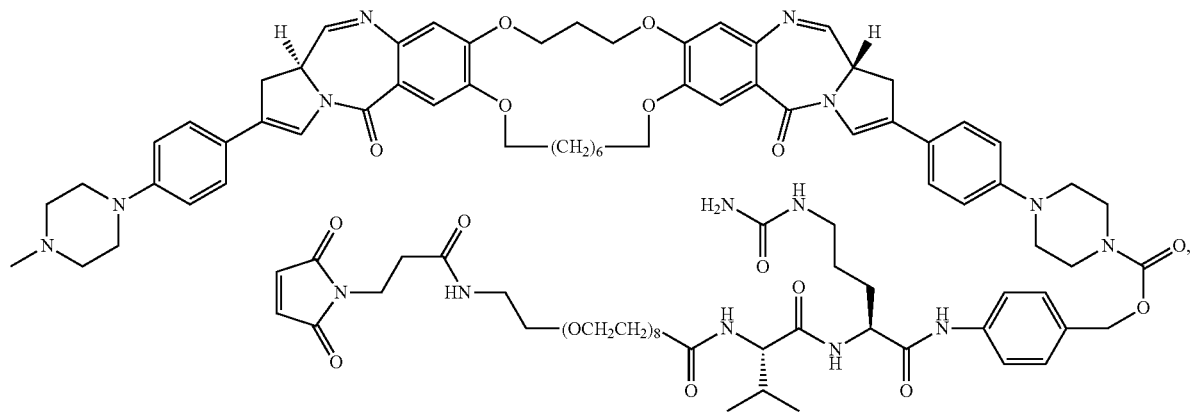
IIIa-5
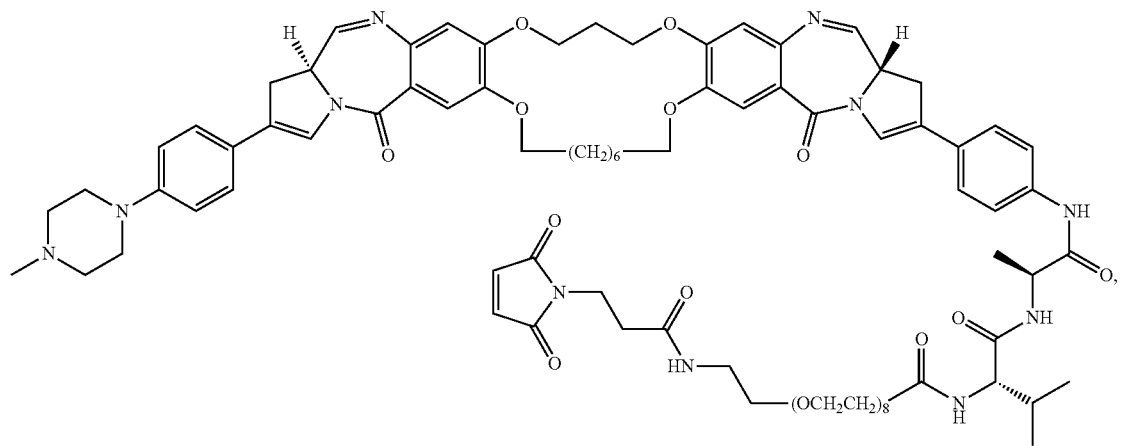

-continued

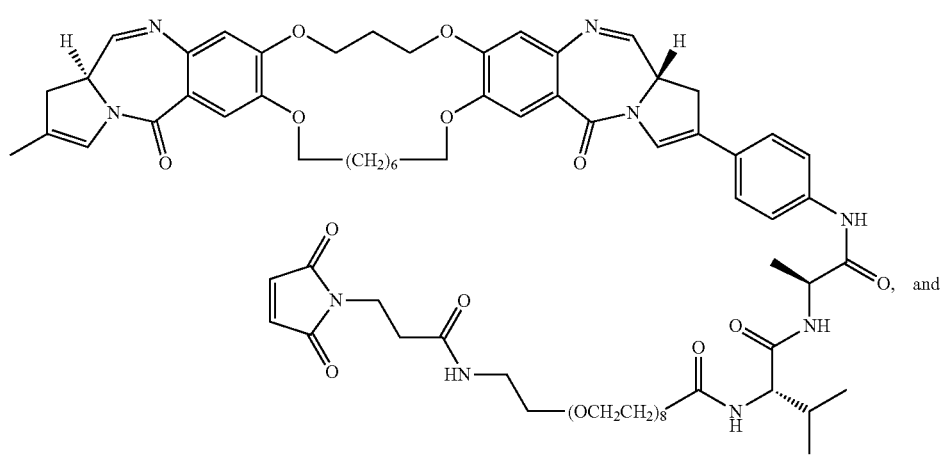

IIIa-6

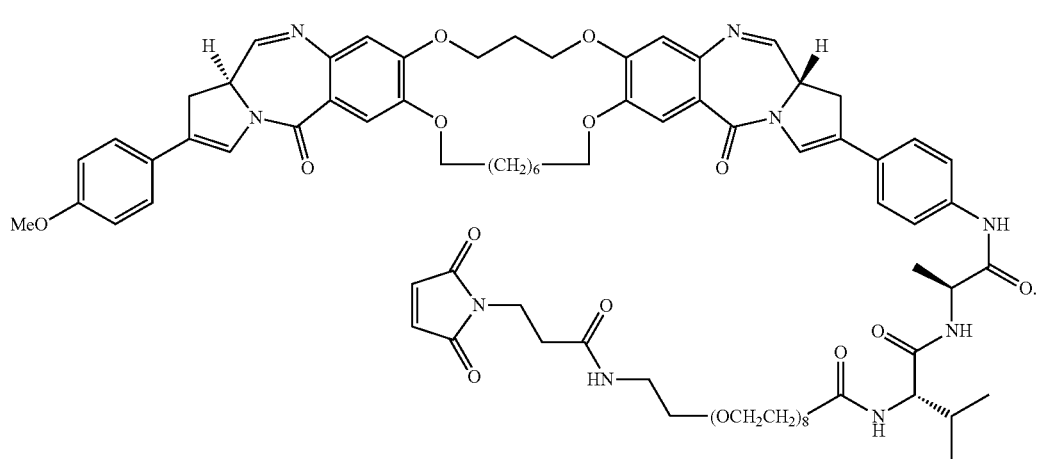

IIIa-7

Preparation of Conjugates

This general procedure is based on introduction of free thiol groups into an antibody by reaction of lysine ε-amino groups with 2-iminothiolane, followed by reaction with a maleimide-containing drug-linker moiety, such as described above. Initially the antibody is buffer exchanged into 0.1 M phosphate buffer (pH 8.0) containing 50 mM NaCl and 2 mM diethylene triamine pentaacetic acid (DTPA) and concentrated to 5-10 mg/mL. Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT (room temperature, circa 25° C.), the antibody is desalted into 50 mM HEPES, 5 mM Glycine, 2 mM DTPA, pH 5.5 using a SEPHADEX™ G-25 column and the number of thiol groups introduced determined rapidly by reaction with dithiodipyridine (DTDP). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about two to three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM HEPES, 5 mM glycine, 2 mM DTPA, pH 5.5)). The thiolated material is maintained on ice while the number of thiols introduced is quantitated as described above.

After verification of the number of thiols introduced, the drug (dimer)-linker moiety is added at a 2.5-fold molar excess per thiol. The conjugation reaction is allowed to proceed in conjugation buffer containing a final concentration of 25% propylene glycol and 5% trehalose. Commonly, the drug-linker stock solution is dissolved in 100% DMSO. The stock solution is added directly to the thiolated antibody.

The conjugation reaction mixture is incubated at RT for 2 h with gentle stirring. A 10-fold molar excess of N-ethyl maleimide (100 mM Stock in DMSO) is then added to the conjugation mixture and stirred for an additional hour to block any unreacted thiols.

The sample is then filtered via a 0.2μ filter The material is buffer exchanged via TFF VivaFlow 50 Sartorius 30 MWCO PES membrane into 10 mg/mL glycine, 20 mg/mL sorbitol, 15% acetonitrile (MeCN) pH 5.0 (5×TFF buffer exchange volume), to remove any unreacted drug. The final formulation is carried out by TFF into 20 mg/mL sorbitol, 10 mg/mL glycine, pH 5.0.

Those skilled in the art will understand that the above-described conditions and methodology are exemplary and non-limiting and that other approaches for conjugation are known in the art and usable in the present invention.

A preferred conjugate of this invention has a structure represented by formula IV:

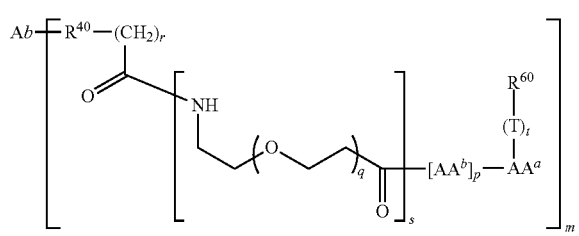

wherein
Ab is an antibody;
m is 1, 2, 3, or 4;

$R^{40}$ is

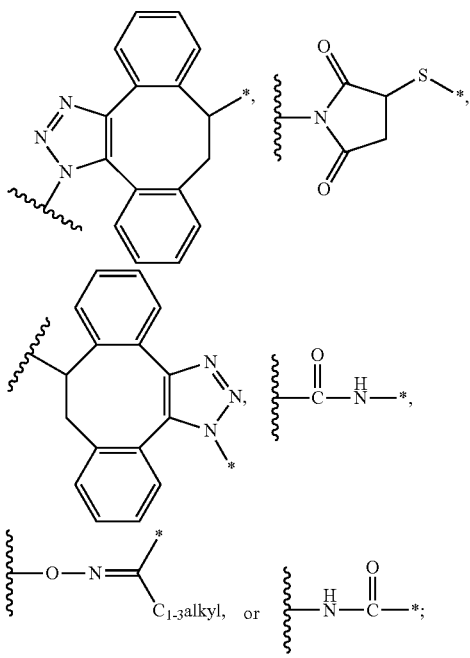

where the open valence of $R^{40}$ that is bonded to Ab is denoted by an asterisk (*) and the open valence of $R^{40}$ that is bonded to $(CH_2)_r$ is denoted by a wavy line (∿∿);

$R^{60}$ is according to formula IIIa, IIIa', or IIIa"

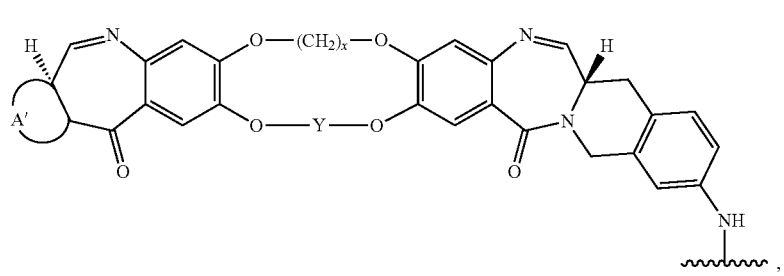

IIIa

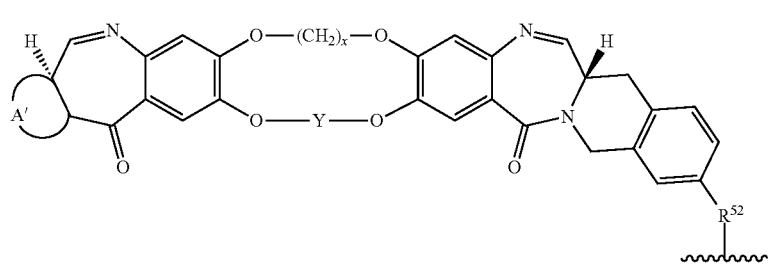

IIIa', or

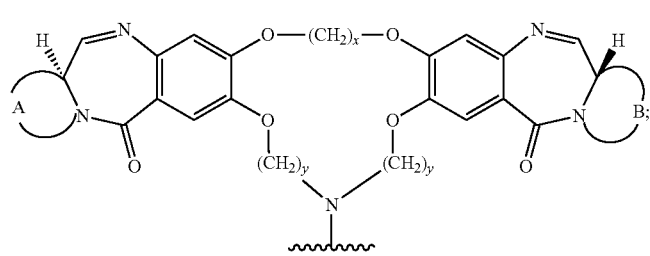

IIIa";

Y is (CH₂)₆₋₁₀ (preferably (CH₂)₈);
x is 3 or 5 (preferably 3);
each y is independently 2, 3, or 4 (preferably both are 4);
A and B are independently according to formula Ia or Ib

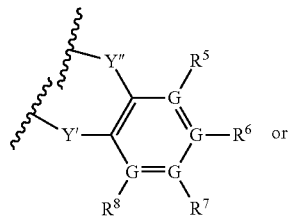

Ia

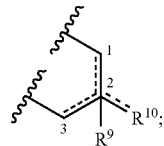

Ib wherein, in formula Ia
Y' and Y" are independently absent, CH₂, C=O, or CHR¹²; wherein each R¹² is independently F, Cl, Br, or C₁-C₃ alkyl, with the proviso that Y' and Y" are not both absent;
each G is independently C or N, with the proviso that no more than two Gs are N; and
each R⁵, R⁶, R⁷, and R⁸ is independently H, Cl, Br, C₁₋₃ alkyl, NO₂, CN, NH₂, O(C₁₋₃ alkyl), or (OCH₂CH₂)₁₋₂O(C₁₋₃ alkyl) (preferably H);
or where a R⁵, R⁶, R⁷, or R⁸ is attached to—i.e., is associated with—a G that is N, such R⁵, R⁶, R⁷, or R⁸ is absent;
and
wherein, in formula Ib,
the dotted lines indicate the optional presence of a C1-C2, C2-C3, or C2-R¹⁰ double bond;
R⁹ is absent if a C1-C2, C2-C3, or C2-R¹⁰ double bond is present and otherwise is H;

R¹⁰ is H, Cl, Br, =CH₂, =CH(C₁₋₅ alkyl), C₁₋₃ alkyl, NO₂, CN, or NH₂ (preferably H);
A' is

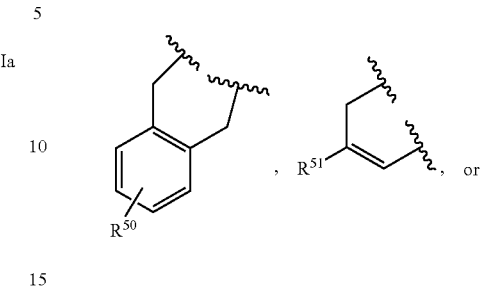

R⁵⁰ is H, Cl, Br, C₁₋₃ alkyl, NO₂, CN, NH₂, O(C₁₋₃ alkyl), or (OCH₂CH₂)₁₋₂O(C₁₋₃ alkyl) (preferably H);
R⁵¹ is H, Cl, Br, C₁₋₃ alkyl, NO₂, CN, NH₂ (preferably H);
T is a self-immolating group;
t is 0 or 1;
AAᵃ and each AAᵇ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 1, 2, 3, 4, 5, 6, 7, 8, 9, or 10 (preferably 2, 3, 4, or 8);
r is 1, 2, 3, 4, or 5 (preferably 2, 3, 4, or 5); and
s is 0 or 1.

In a preferred conjugate according to formula IV, R⁶⁰ is IIIa, corresponding to a conjugate having a structure represented by formula IVa:

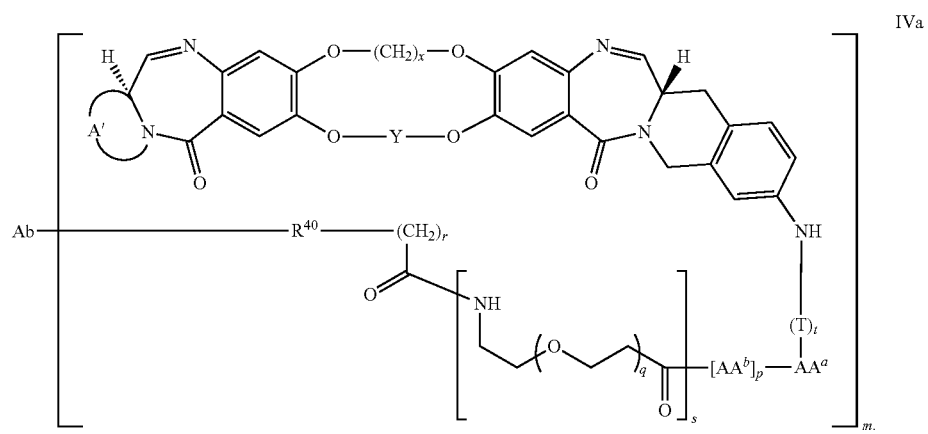

In another preferred conjugate according to formula IV, R$^{60}$ is IIIa', corresponding to a conjugate having a structure represented by formula IVa':

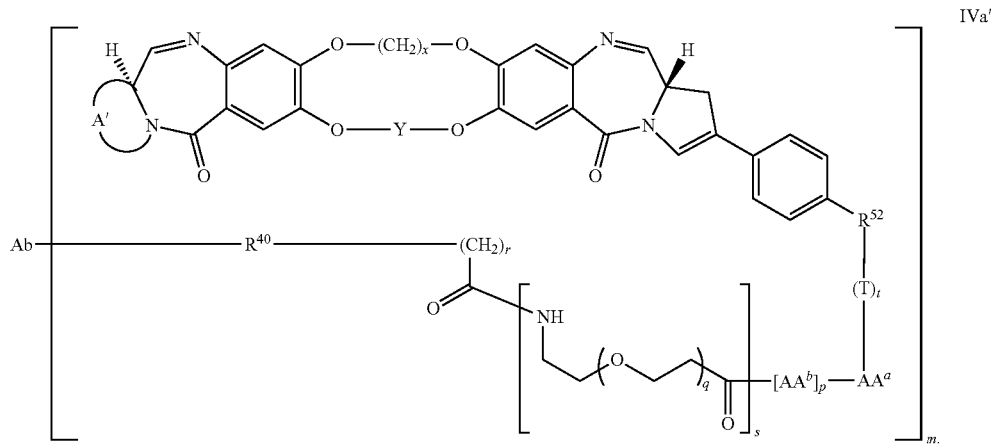

In another preferred conjugate according to formula IV, R$^{60}$ is IIIa", corresponding to a conjugate having a structure represented by formula IVa":

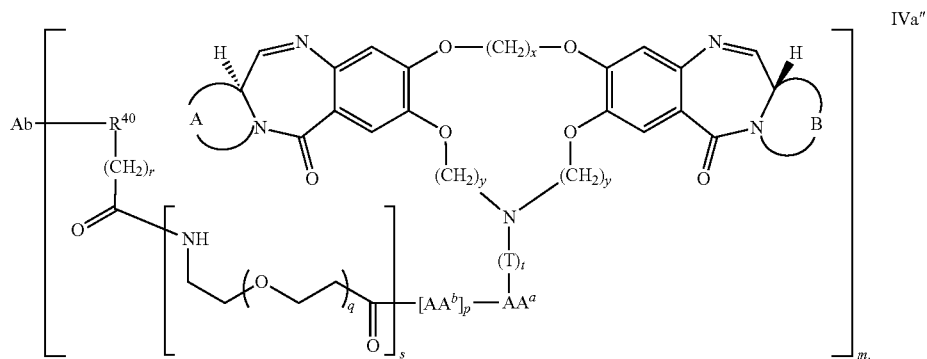

Pharmaceutical Compositions

In another aspect, the present disclosure provides a pharmaceutical composition comprising a compound of the present invention, or of a conjugate thereof, formulated together with a pharmaceutically acceptable carrier or excipient. It may optionally contain one or more additional pharmaceutically active ingredients, such as an antibody or another drug. The pharmaceutical compositions can be administered in a combination therapy with another therapeutic agent, especially another anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20th Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µ/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

The pharmaceutical composition can be a controlled or sustained release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al. (1995) *FEBS Lett.* 357:140; M. Owais et al. (1995) *Antimicrob. Agents Chemother.* 39:180; Briscoe et al. (1995) *Am. J. Physiol.* 1233:134; Schreier et al. (1994 *J. Biol. Chem.* 269:9090; Keinanen and Laukkanen (1994) *FEBS Lett.* 346:123; and Killion and Fidler (1994) *Immunomethods* 4:273.

Uses

Compounds of this invention or their conjugates can be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as: inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be renal, lung, gastric, or ovarian cancer.

Compounds of this invention or their conjugates can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immuno-modulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

EXAMPLES

The practice of this invention can be further understood by reference to the following examples, which are provided by way of illustration and not of limitation. The following general procedures are illustrative, with those skilled in the art understanding that alternative but equivalent methods can be used.

Example 1—Dimer IIa-9

Figure 1B:
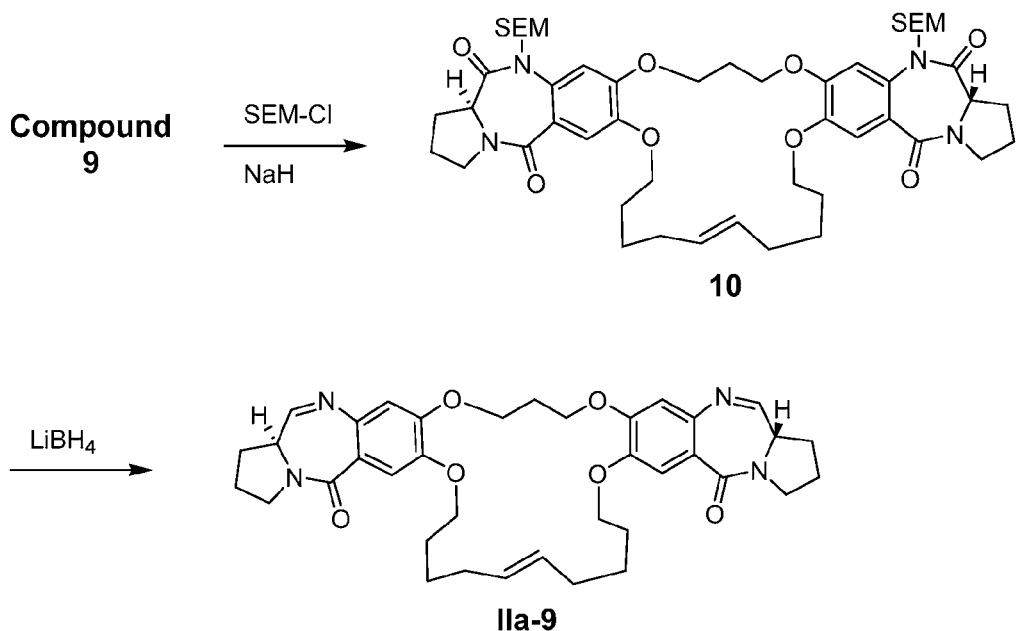

This example pertains to FIGS. 1A-1B and the synthesis of dimer IIa-9.

4-(Benzyloxy)-5-methoxy-2-nitrobenzoyl chloride 1 was prepared from the corresponding methyl ester as follows: To a solution of methyl 4-(benzyloxy)-5-methoxy-2-nitrobenzoate (Harve Chem, 15 g, 47.3 mmol) in tetrahydrofuran (THF, 350 mL) was added a solution of aq. NaOH (56.7 mL, 142 mmol, 2.5M). The reaction was stirred at 50° C. for 5 h. The reaction was cooled to room temperature (RT) and then concentrated in vacuo to remove the THF. The remaining aqueous layer was acidified with aq. HCl (6 N) to pH 2. The resulting yellow precipitate was filtered, washed with water, and dried under vacuum to give 4-(benzyloxy)-5-methoxy-2-nitrobenzoic acid (14.32 g, 100% yield). LCMS (M+H)=304.08; $^1$H NMR (400 MHz, METHANOL-$d_4$) δ 7.60 (s, 1H), 7.53-7.45 (m, 2H), 7.45-7.31 (m, 3H), 7.29 (s, 1H), 5.23 (s, 2H), 3.98 (s, 3H).

To a solution of the above nitrobenzoic acid (1.2 g, 3.96 mmol) in THF (30 mL) was added dropwise oxalyl chloride (0.416 mL, 4.75 mmol), followed by N,N-dimethyl-formamide (DMF, 20 uL). The resulting solution was stirred at RT for 35 h before it was concentrated in vacuo to give acid chloride 1 as a yellow solid.

Acid chloride 1 was dissolved in THF (20 mL) and added dropwise to a solution of of S-methyl pyrrolidine-2-carboxylate 2 hydrochloride (0.768 g, 4.75 mmol) and triethylamine (NEt$_3$, 1.65 mL, 11.87 mmol) in THF (10 mL) at 0° C. The reaction mixture was warmed to RT and stirred at RT for 1 h before quenching with aq. LiCl and concentrated to remove the THF. The resulting mixture was extracted with EtOAc (3×). The combined organic layers were washed with sat. aq. NaHCO$_3$ and then brine and dried over Na$_2$SO$_4$ and concentrated in vacuo. The crude product mixture was purified using ISCO silica gel chromatography (80 g column, gradient from 0% to 100% EtOAc/dichloromethane (DCM) in 15 minutes) to give ester 3 (1.18 mg, 72% yield). LCMS (M+H)=415.4; $^1$H NMR (400 MHz, CHLOROFORM-d) δ 7.77 (s, 1H), 7.51-7.32 (m, 5H), 6.92-6.80 (m, 1H), 5.25-5.20 (m, 2H), 4.80-4.73 (m, 1H), 4.03-3.93 (m, 3H), 3.82 (s, 2H), 3.56 (s, 1H), 3.38-3.30 (m, 1H), 3.21 (s, 1H), 2.41-2.30 (m, 1H), 2.16-2.07 (m, 1H), 2.04-1.87 (m, 2H).

A suspension of ester 3 (900 mg, 2.172 mmol) and Pd(OH)$_2$ (20% on carbon, 90 mg) in EtOH (15 mL) was stirred under H$_2$ (50 psi) for 3 h. The reaction mixture was filtered through a pad of CELITE™ and washed with EtOAc. The combined filtrates were concentrated and dissolved in MeOH (10 mL). After a drop of AcOH was added, the reaction was heated at 80° C. for 5 h. The reaction was then cooled to RT and concentrated. The residue was purified using ISCO silica gel chromatography (40 g column, 0-100% EtOAc/Hexane gradient) to give compound 4. LCMS (M+H)=263; $^1$H NMR (400 MHz, CHLOROFORM-d) δ 10.18 (s, 1H), 9.89 (br. s., 1H), 7.22 (s, 1H), 6.55 (s, 1H), 4.17-3.96 (m, 1H), 3.77 (s, 3H), 3.63-3.37 (m, 2H), 1.96-1.63 (m, 4H).

A suspension of compound 4 (0.8 g, 3.05 mmol) and 1,3-bromopropane 4a (0.308 g, 1.525 mmol) and K$_2$CO$_3$ (527 mg, 3.81 mmol) in DMSO (8 mL) were stirred at RT for 12 h. The reaction mixture was diluted with aq. NH$_4$Cl and extracted with chloroform (3×). The combined organic layers were washed with brine, dried over Na$_2$SO$_4$, and concentrated in vacuo. The crude product mixture was purified using ISCO silica gel chromatography (gradient from 0% to 10% MeOH/DCM) to give compound 5 (670 mg, 78% yield). LCMS (M+H)=565; $^1$H NMR (400 MHz, CHLOROFORM-d) δ 7.45 (s, 2H), 6.54 (s, 2H), 4.19 (d, J=7.5 Hz, 4H), 4.03 (d, J=5.9 Hz, 2H), 3.89 (s, 6H), 3.82-3.72 (m, 2H), 3.64-3.55 (m, 2H), 2.73 (br. s., 2H), 2.37-2.32 (m, 2H), 2.07-1.95 (m, 6H).

To a solution of compound 5 (650 mg, 1.151 mmol) in DCM (2 mL) at −78° C. was added dropwise a solution of boron tribromide (10.04 mL, 10.4 mmol, 1M in DCM). The reaction was slowly warmed to −5° C. and stirred for 30 min. The reaction was then quenched with aq. potassium phosphate dibasic buffer (5 mL), and then concentrated to remove DCM. The remaining slurry was filtered to give a grey solid, which was purified using ISCO silica gel chromatography (120 g column, gradient from 0% to 10% MeOH/DCM) to give compound 6 (202 mg, 33% yield). LCMS (M+H)=537; $^1$H NMR (400 MHz, DMSO-$d_6$) δ 10.10 (br. s., 2H), 9.44-9.01 (m, 2H), 7.17 (s, 2H), 6.66 (s, 2H), 4.13 (br. s., 5H), 4.03 (d, J=6.4 Hz, 2H), 3.51 (br. s., 6H), 2.46 (br. s., 1H), 2.32-2.16 (m, 2H), 2.06-1.66 (m, 7H).

A suspension of compound 6 (86 mg, 0.160 mmol), 6-bromohex-1-ene 6a (52.3 mg, 0.321 mmol), and K$_2$CO$_3$ (66.5 mg, 0.481 mmol) in DMF (1.5 mL) was stirred at RT for 15 h. The reaction mixture was filtered and purified using ISCO silica gel chromatography (40 g column, gradient from 0% to 10% MeOH/DCM) to give compound 7 (55 mg, 49% yield). LCMS (M+H)=701.7.

A vial was charged with compound 7 (52 mg, 0.074 mmol). A solution of Grubbs-II catalyst (6.30 mg, 7.42 μmol) in DCE (10 mL) was then added. The resulting solution was degassed and heated to 75° C. for 1 h. The reaction mixture was then concentrated and purified using ISCO silica gel chromatography (12 g column, gradient 0% to 10% MeOH/DCM) to give the 21-membered macrocycle 8 (44 mg, 88%, along with ~10% 20-membered macrocycle by-product 9). LCMS (M+H)=673.7.

To a solution of the mixture of compounds 8 and 9 (18 mg, 0.027 mmol) in DMF (1 mL) at 0° C. was added NaH (4.01 mg, 0.067 mmol). The resulting suspension was stirred at 0° C. for 30 min before 2-(chloromethoxy)ethyl)trimethylsilane (SEM-Cl, 0.014 mL, 0.080 mmol) was added. The reaction was then stirred at 0° C. for 1 h before quenching with brine. The mixture was extracted with EtOAc (3×). The combined organic layers were dried over Na$_2$SO$_4$, concentrated, and purified using ISCO silica gel chromatography (12 g column, gradient from 0% to 100% MeOH/DCM) to give compound 10. LCMS (M+H)=933; $^1$H NMR (400 MHz, CHLOROFORM-d) δ 7.37 (s, 2H), 7.22 (s, 2H), 5.48 (m, 2H), 5.43 (t, J=3.5 Hz, 2H), 4.70 (m, 2H), 4.29-4.21 (m, 4H), 4.14-4.03 (m, 6H), 3.84-3.65 (m, 7H), 3.62-3.50 (m, 2H), 2.79-2.67 (m, 2H), 2.35 (m, 2H), 2.12-1.96 (m, 10H), 1.80 (m, 4H), 1.58-1.47 (m, 2H), 0.98 (m, 4H), 0.04-0.02 (s, 18H).

To a solution of compound 10 in THF/EtOH (1:1, 1 mL) at 0° C. was added a solution of lithium borohydride (0.268 mL, 0.535 mmol, 2M in THF). The resulting solution was stirred at 0° C. for 1 h before it was warmed to RT and stirred for 5 min. The reaction was then quenched with brine and extracted with CHCl$_3$ (3×). The combined organic layers were dried over Na$_2$SO$_4$ and concentrated. The residue was then taken up in CHCl$_3$/EtOH (1:1, 2 mL). Silica gel (0.9 g) was added, followed by water (1 mL). The resulting suspension was stirred at RT for 48 h and then filtered, washing with 10% MeOH/CHCl$_3$. The filtrate was concentrated and purified using reverse phase HPLC (Column: Phenomenex Luna C18 20×100 mm; Mobile Phase A: 10:90 MeCN:water with 0.1% trifluoroacetic acid (TFA); Mobile Phase B: 90:10 MeCN:water with 0.1% TFA acid; Gradient: 0-80% B over 15 minutes; Flow: 20 mL/min; Detection: UV at 220 nm) to give The fractions containing desired fractions were combined and neutralized with aq. NaHCO3, then extracted with chloroform, and dried and concentrated to give dimer IIa-9. (7.1 mg, 39% over two steps). LCMS (M+H)=641.3; $^1$H NMR (400 MHz, CHLOROFORM-d) δ 7.68 (d, J=4.4 Hz, 2H), 7.53 (s, 2H), 6.85 (s, 2H), 5.46 (m, 2H), 4.36-4.23 (m, 4H), 4.20-4.12 (m, 2H), 4.11-4.03 (m, 2H), 3.87-3.82 (m, 2H), 3.75 (dt, J=7.5, 4.0 Hz, 2H), 3.60 (dt, J=11.8, 7.8 Hz, 2H), 2.41-2.30 (m, 6H), 2.14-2.01 (m, 8H), 1.88-1.77 (m, 4H), 1.67-1.58 (m, 4H).

Example 2—Dimers IIa-3 and IIa-4

Figure 2:
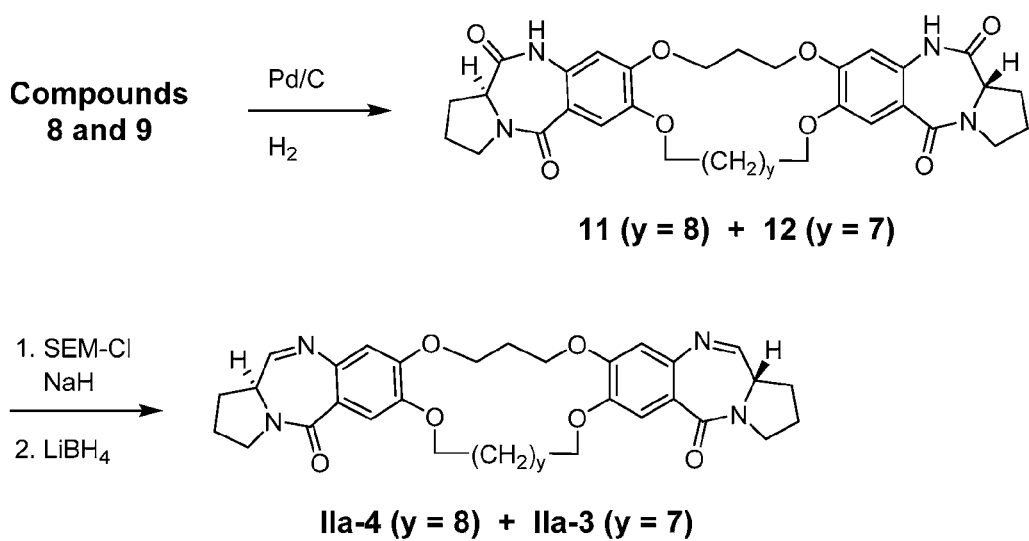

This example pertains to FIG. 2 and the synthesis of dimers IIa-3 and IIa-4.

A suspension of a mixture of compounds 8 and 9 (24 mg, 0.036 mmol) and 10% Pd/C (6 mg) in MeOH (3 mL) was stirred under a balloon of H$_2$ for 3 h. The reaction mixture was purged with N$_2$ and filtered through a pad of CELITE™, washing with EtOAc. The combined filtrates were concentrated to give 21-membered macrocycle 11 (24 mg, 100% yield, along with ~10% macrocycle 12). LCMS (M+H)=675.4.

To a solution of the mixture of macrocycle 11 and 12 (24 mg, 0.036 mmol) in DMF (1 mL) at 0° C. was added NaH (5.33 mg, 0.089 mmol). The resulting suspension was stirred at 0° C. for 30 min before SEM-Cl (0.019 mL, 0.107 mmol) was added. The reaction was stirred at 0° C. for 1 h before it was quenched with brine. The mixture was extracted with EtOAc (3×). The combined organic layers were dried over Na$_2$SO$_4$, concentrated, and purified using ISCO silica gel chromatography (12 g column, gradient from 0% to 100% MeOH/DCM) to give a mixture of SEM-macrocycles (21-membered macrocycle: LCMS (M+H)=935. 20-membered macrocycle: LCMS (M+H)=921).

To a solution of the mixture of the above SEM-macrocycles in THF/EtOH (1:1, 1 mL) at 0° C. was added a solution of LiBH$_4$ (0.356 mL, 0.71 mmol, 2M in THF). The resulting solution was stirred at 0° C. for 1 h before warming to RT and stirring for 15 min. The reaction was quenched with brine and extracted with CHCl$_3$ (3×). The combined organic layers were dried over Na$_2$SO$_4$ and concentrated. The residue was taken up in CHCl$_3$/EtOH (1:1, 2 mL). Silica gel (0.9 g) was added, followed by water (1 mL). The resulting suspension was stirred at RT for 48 h and filtered, washing with 10% MeOH/CHCl$_3$. The filtrate was concentrated and purified using reverse phase HPLC to give dimers IIa-4 and IIa-3 (Column: Phenomenex Luna C18 20×100 mm; Mobile Phase A: 10:90 MeCN:water with 0.1% trifluoroacetic acid (TFA); Mobile Phase B: 90:10 MeCN:water with 0.1% TFA acid; Gradient: 0-80% B over 15 minutes; Flow: 20 mL/min; Detection: UV at 220 nm).

Dimer IIa-4: (7.5 mg, 31% yield); LCMS (M+H)=643.4; $^1$H NMR (400 MHz, CHLOROFORM-d) δ 7.68 (d, J=4.4 Hz, 2H), 7.53 (s, 2H), 6.84 (s, 2H), 4.33-4.16 (m, 6H), 4.13-4.06 (m, 2H), 3.88-3.80 (m, 2H), 3.79-3.71 (m, 2H), 3.64-3.57 (m, 2H), 2.44-2.30 (m, 6H), 2.15-2.04 (m, 4H), 1.85-1.77 (m, 4H), 1.61-1.52 (m, 4H), 1.44-1.38 (m, 8H).

Dimer IIa-3: (1 mg, 4% yield); LCMS (M+H)=629.4; $^1$H NMR (400 MHz, CHLOROFORM-d) δ 7.68 (d, J=4.4 Hz, 2H), 7.55 (s, 2H), 6.86 (s, 2H), 4.37-4.24 (m, 4H), 4.21-4.14 (m, 2H), 4.12-4.06 (m, 2H), 3.87-3.80 (m, 2H), 3.79-3.70 (m, 4H), 3.63-3.56 (m, 2H), 2.42-2.31 (m, 6H), 2.14-2.06 (m, 4H), 1.83-1.78 (m, 4H), 1.61-1.52 (m, 4H), 1.43-1.33 (m, 6H).

Example 3—Dimer IIa-1

Figure 3:
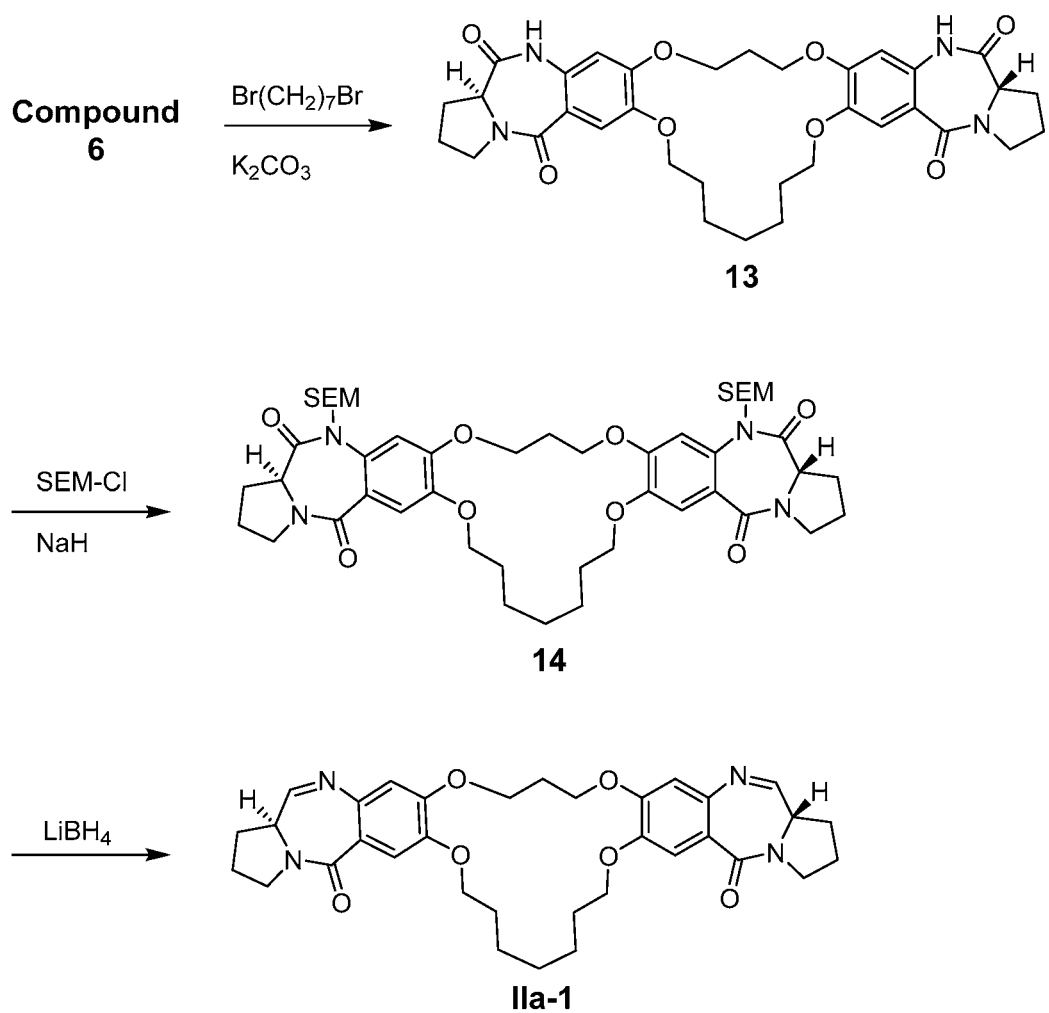

This example pertains to FIG. 3 and the synthesis of dimer IIa-1.

To a suspension of compound 6 (29 mg, 0.054 mmol) and K$_2$CO$_3$ (7.47 mg, 0.054 mmol) in DMF (1.5 mL) was added 1,7-dibromoheptane (14.64 mg, 0.057 mmol). The mixture was heated at 50° C. for 2 h. The reaction was cooled to RT. The reaction mixture was filtered and purified using ISCO silica gel chromatography (12 g column, gradient from 0 to 10% MeOH/DCM) to give macrocycle 13. LCMS (M+H)=633.5.

To a solution of macrocycle 13 in DMF (0.8 mL) at 0° C. was added NaH (4.32 mg, 0.108 mmol). The resulting suspension was stirred at 0° C. for 30 min before SEM-Cl (0.019 mL, 0.11 mmol) was added. The reaction was stirred at 0° C. for 1 h before it was quenched with brine. The mixture was extracted with EtOAc (3×). The combined organic layers were dried over Na$_2$SO$_4$, concentrated, and purified using ISCO silica gel chromatography (12 g column, gradient from 0% to 100% MeOH/DCM) to give SEM-macrocycle 14 (9 mg, 10.08 μmol, 18.6% yield over two steps). LCMS (M+H)=893.4.

To a solution of SEM-macrocycle 14 (9 mg, 10.08 μmol) in THF/EtOH (1:1, 1 mL) at 0° C. was added a solution of LiBH$_4$ (101 μL, 0.202 mmol, 2M in THF). The resulting solution was stirred at 0° C. for 1 h before warming to RT and stirring for 15 min. The reaction was quenched with brine and extracted with CHCl$_3$ (3×). The combined organic layers were dried over Na$_2$SO$_4$ and concentrated. The residue was taken up in CHCl$_3$/EtOH (1:1, 2 mL). Silica gel (0.7 g) was added, followed by water (0.6 mL). The resulting suspension was stirred at RT for 24 h and filtered and washed with 10% MeOH/CHCl$_3$. The filtrate was concentrated and purified using reverse phase HPLC (Column: Phenomenex Luna C18 20×100 mm; Mobile Phase A: 10:90 MeCN:H$_2$O with 0.1% trifluoroacetic acid (TFA); Mobile Phase B: 90:10 MeCN:water with 0.1% TFA acid; Gradient: 0-70% B over 15 min; Flow: 20 mL/min; Detection: UV at 220 nm) to give dimer IIa-1 (1.8 mg, 2.70 μmol, 26.8% yield). LCMS (M+H)=601.2; $^1$H NMR (400 MHz, CHLOROFORM-d) δ

7.68 (d, J=4.4 Hz, 2H), 7.54 (s, 2H), 6.90 (s, 2H), 4.35-4.25 (m, 4H), 4.18 (dt, J=9.5, 5.7 Hz, 2H), 4.15-4.05 (m, 2H), 3.86-3.78 (m, 2H), 3.77-3.72 (m, 2H), 3.65-3.54 (m, 2H), 2.42-2.28 (m, 6H), 2.14-2.03 (m, 4H), 1.91-1.80 (m, 4H), 1.70-1.61 (m, 4H), 1.49-1.41 (m, 2H).

Example 4—Dimer IIb-5

Figure 4A:
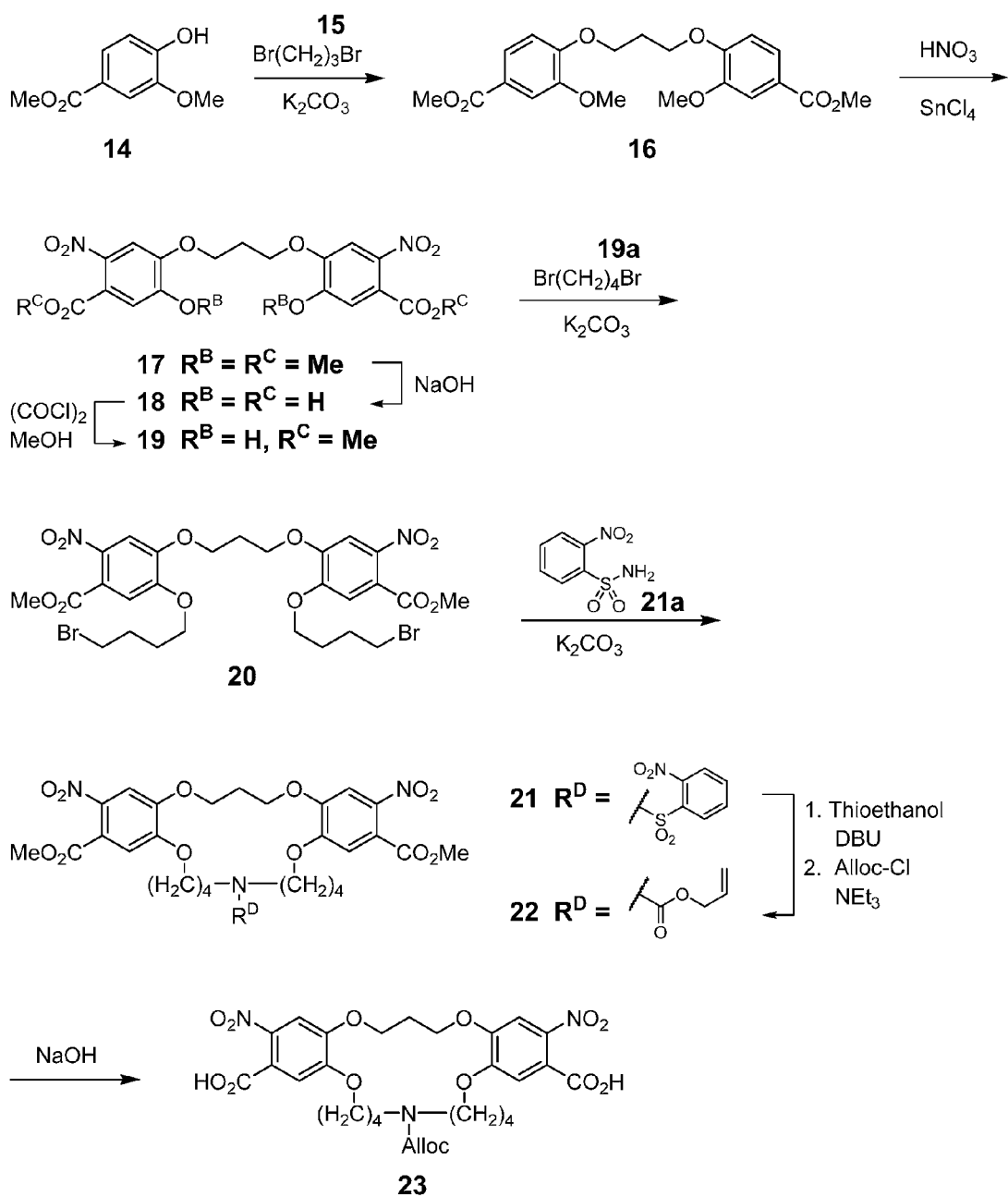
Figure 4B:
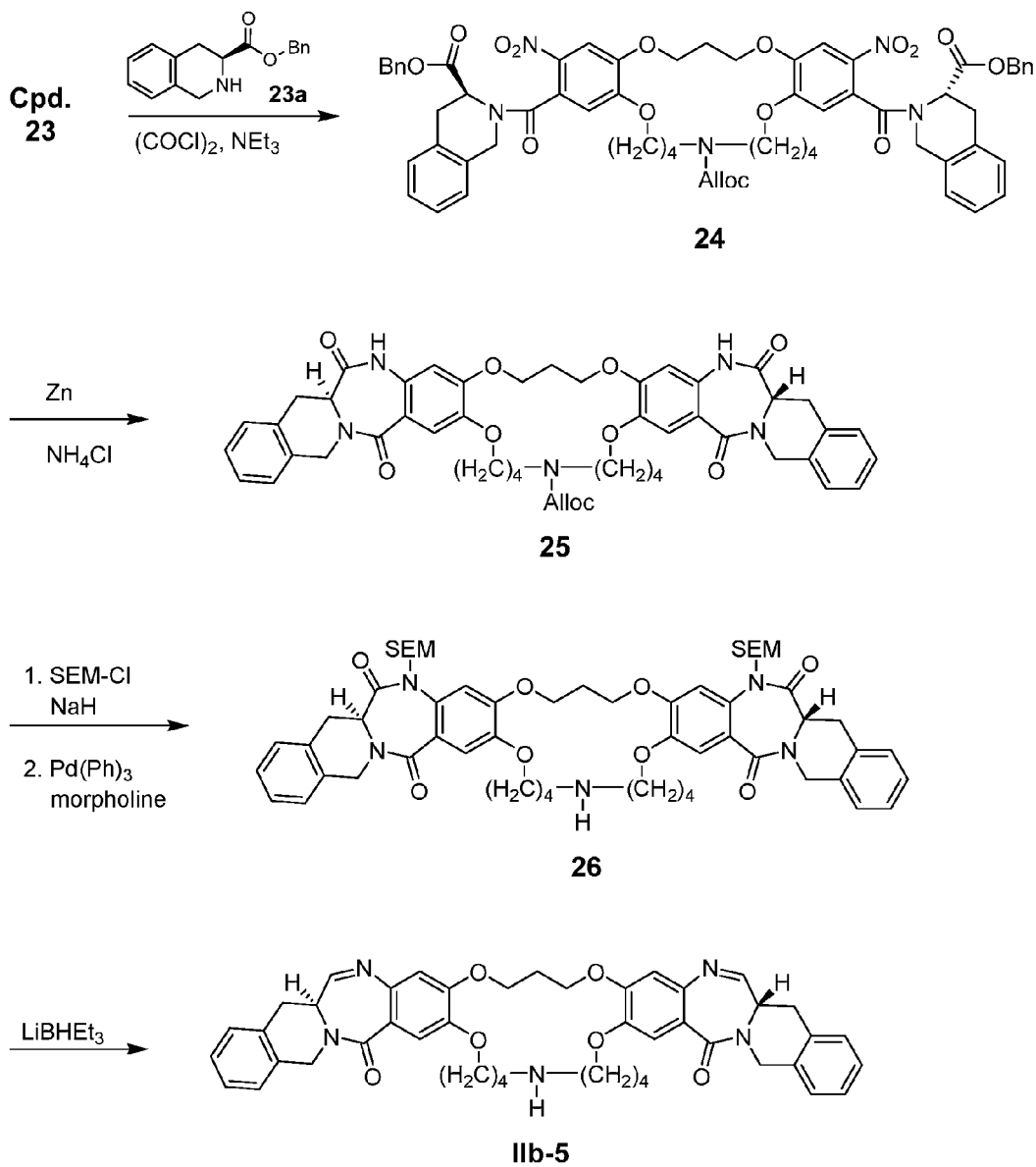

This example pertains to FIGS. 4A-4B and the synthesis of dimer IIb-5.

A suspension of methyl 4-hydroxy-3-methoxybenzoate 14 (18 g, 99 mmol), $K_2CO_3$ (20.48 g, 148 mmol) and 1,3-dibromopropane 15 (5.04 ml, 49.4 mmol) in DMSO (300 mL) was stirred at RT for 16 hours. To the reaction mixture was added water, and the resulting solution stirred at RT for 20 min. The resulting precipitate was filtered, washed with water and dried under vacuum. The resulting white solid was triturated with EtOAc/DCM and filtered to give compound 16 (10.45 g, 52.4%) and a dark brown filtrate. The filtrate was purified by ISCO (0%-50% of EtOAC/DCM in 15 minutes, 120 g column) to provide additional compound 16 (3.55 g, 17.7%). LCMS (M+H)=405; $^1$H NMR (400 MHz, DMSO-$d_6$) δ 7.58 (dd, J=8.4, 2.0 Hz, 2H), 7.46 (d, J=2.0 Hz, 2H), 7.12 (d, J=8.6 Hz, 2H), 4.22 (t, J=6.2 Hz, 4H), 3.83 (s, 6H), 3.81 (s, 6H), 2.24 (t, J=6.2 Hz, 2H).

To a solution of tin (IV) chloride (19.91 mL, 19.91 mmol, 1M in DCM) at 0° C. was added dropwise concentrated nitric acid (1.375 mL, 27.7 mmol). The resulting mixture was added dropwise to a solution of compound 16 (3.5 g, 8.65 mmol) in DCM (15 mL) at −25° C. The reaction was stirred at −25° C. for 30 min before it was quenched with water (100 mL). The organic layer was separated. The aq. layer was extracted with EtOAc (2×). The combined organic layers were concentrated to give a crude product, which was recrystallized from hot DCM/Hexane to give compound 17 (3.5 g, 82% yield) as off white crystals. LCMS (M+H)=495; $^1$H NMR (400 MHz, DMSO-$d_6$) δ 7.68 (s, 2H), 7.32 (s, 2H), 4.29 (t, J=6.2 Hz, 4H), 3.91 (s, 6H), 3.83 (s, 6H), 2.35-2.13 (m, 2H).

A flask was charged with compound 17 (3.1 g, 6.27 mmol) and aq. NaOH (25.08 mL, 62.7 mmol, 2.5 M). The reaction mixture was heated at 100° C. for 16 h. The heterogenous mixture became reddish solution at the end of the reaction. The reaction mixture was cooled to RT and acidified with aq. HCl to pH2. The resulting precipitate was filtered, washed with water and dried to give compound 18 (2.65 g, 6.05 mmol, 96% yield). $^1$H NMR (400 MHz, DMSO-$d_6$) δ 13.41 (br. s., 2H), 10.62 (br. s., 2H), 7.59 (s, 2H), 7.10 (s, 2H), 4.31 (t, J=6.2 Hz, 4H), 2.25 (quin, J=6.1 Hz, 2H).

To a solution of compound 18 (2.9 g, 6.62 mmol) in THF (5 mL) at RT was added oxalyl chloride (1.390 mL, 15.88 mmol), followed by 2 drops of DMF. The reaction was stirred at RT for 2 h before it was concentrated and dissolved in MeOH (20 mL). The resulting solution was stirred at RT for 30 min and concentrated. The crude product was triturated with water, filtered, and dried to give compound 19 (3 g, 6.43 mmol, 97% yield) LCMS (M+H)=467; $^1$H NMR (400 MHz, DMSO-$d_6$) δ 10.80 (br. s., 2H), 7.65 (s, 2H), 7.10 (s, 2H), 4.33 (t, J=5.9 Hz, 4H), 3.80 (s, 6H), 2.39-2.15 (m, 2H).

To a suspension of compound 19 (1 g, 2.144 mmol) and $K_2CO_3$ (0.889 g, 6.43 mmol) in DMF (1 mL) was added 1,4-dibromobutane 19a (3.70 g, 17.15 mmol). The reaction mixture was heated to 80° C. for 2 h before it was cooled to RT, diluted with water, and extracted with EtOAc (3×). The combined organic layers were concentrated and purified using ISCO silica gel chromatography (40 g column, gradient from 0% to 50% EtOAC/Hexane) to give compound 20 (0.95 g, 60.2% yield). LCMS (M+H)=521; $^1$H NMR (400 MHz, CHLOROFORM-d) δ 7.47 (s, 2H), 7.04 (s, 2H), 4.31 (s, 5H), 4.11 (s, 4H), 3.89 (s, 6H), 3.51 (t, J=6.3 Hz, 4H), 2.42 (s, 2H), 2.14-1.92 (m, 8H).

A suspension of compound 20 (0.95 g, 1.290 mmol), 2-nitrobenzenesulfonamide 21a (0.261 g, 1.290 mmol) and $K_2CO_3$ (0.535 g, 3.87 mmol) in DMF (20 mL) was heated at 80° C. for 2 h. The reaction was diluted with water and extracted with EtOAc (3×). The combined organic layers were concentrated and purified using ISCO silica gel chromatography (80 g column, gradient from 0% to 80% EtOAC/Hexane) to give macrocycle 21 (330 mg, 32.9% yield). LCMS (M+H)=777.5; $^1$H NMR (400 MHz, CHLOROFORM-d) δ 7.97 (dd, J=7.6, 1.7 Hz, 1H), 7.74-7.64 (m, 2H), 7.63-7.56 (m, 1H), 7.51 (s, 2H), 7.07 (s, 2H), 4.36-4.28 (m, 4H), 4.17-4.07 (m, 4H), 3.90 (s, 6H), 3.36 (br. s., 4H), 2.31 (t, J=6.1 Hz, 2H), 1.86-1.80 (m., 8H)

To a solution of macrocycle 21 (320 mg, 0.412 mmol) in DMF (3 mL) was added 2-mercaptoethanol (322 mg, 4.12 mmol) and 1,8-diazabicyclo[5.4.0]undec-7-ene (DBU, 310 μL, 2.060 mmol). The mixture was stirred at RT for 2 h, diluted with DCM, washed with water and then brine, dried over sodium sulfate, and concentrated. The residue was taken up in DCM (4 mL) and cooled to 0° C. Triethylamine (115 μl, 0.824 mmol) was then added, followed by chloro allylformate (Alloc-Cl, 99 mg, 0.824 mmol). The mixture was stirred at 0° C. for 30 min before it was quenched with water, extracted with DCM, dried, and concentrated. The crude product was purified using ISCO silica gel chromatography (40 g column, gradient from 0% to 70% EtOAc/Hexane) to give macrocycle 22 (140 mg, 0.207 mmol, 50.3% yield). LCMS (M+H)=676.2

To a suspension of macrocycle 22 in MeOH (1 mL) and THF (6 mL) was added aq. NaOH (1M, 1 mL). The resulting mixture was stirred at RT for 12 h. The reaction mixture was concentrated to remove THF and MeOH. The residue was acidified with aq. HCL (1N) and extracted with EtOAc (3×). The combined organic layers were washed with brine, dried, and concentrated to give acid 23 (135 mg, 0.208 mmol, 97% yield). LCMS (M+H)=485.

To a solution of acid 23 (135 mg, 0.208 mmol) in THF (2 mL) was added oxalyl chloride (45.6 μl, 0.521 mmol), followed by DMF (5 uL). The reaction mixture was stirred at RT for 2 h and concentrated. The residue was dissolved in THF (10 mL) and cooled to 0° C. A solution of (S)-benzyl 1,2,3,4-tetrahydroisoquinoline-3-carboxylate p-toluenesulfonic acid salt 23a (Accela, 275 mg, 0.625 mmol) and $NEt_3$ (0.29 mL, 2.09 mmol) in THF (5 mL) was added dropwise. The reaction mixture was slowly warmed to RT and stirred for 15 min before quenching with water. The resulting mixture was extracted with EtOAc (3×). The combined organic layers were dried, concentrated, and purified using ISCO silica gel chromatography (12 g column, gradient from 0% to 100% EtOAc/hexane) to give compound 24 (190 mg, 0.166 mmol, 80% yield). LCMS (M+H)=1146.8.

A suspension of compound 24 (190 mg, 0.166 mmol), zinc powder (108 mg, 1.658 mmol), and $NH_4Cl$ (133 mg, 2.486 mmol) in MeOH (4 mL) was heated to 50° C. and stirred for 8 h. The reaction mixture was cooled to RT, diluted with MeOH, and filtered through a pad of CELITE™, washing with MeOH followed by EtOAc. The combined filtrates were concentrated and purified using ISCO silica gel chromatography (24 g column, gradient from 0% to 10% MeOH/DCM,) to give compound 25 (125 mg, 0.144 mmol, 87% yield). LCMS (M+H)=870.1; $^1$H NMR (400 MHz, CHLOROFORM-d) δ 7.40-7.36 (m, 3H), 7.35-7.21 (m, 9H), 6.52 (br. s., 2H), 6.01-5.76 (m, 1H), 5.25 (dd, J=17.2, 1.5 Hz, 1H), 5.16 (dd, J=10.5, 1.4 Hz, 1H), 5.06 (d, J=15.2 Hz, 2H), 4.55 (d, J=5.5 Hz, 2H), 4.45 (d, J=15.4 Hz, 2H), 4.24-4.05 (m, 4H), 4.00 (br. s., 2H), 3.49 (dd, J=15.4, 7.0 Hz, 2H), 3.31 (br. s., 4H), 3.01 (d, J=15.4, 6.4 Hz, 2H), 2.19 (d, J=5.5 Hz, 2H), 1.84-1.76 (m., 8H).

To a solution of compound 25 (120 mg, 0.138 mmol) in DMF (5 mL) at 0° C. was added NaH (9.93 mg, 0.414 mmol). The resulting suspension was stirred for 30 min before SEM-Cl (0.073 mL, 0.414 mmol) was added. The reaction mixture was then slowly warmed to RT and stirred for 2 h before quenching with brine. The resulting mixture was extracted with EtOAC (3×). The combined organic layers were dried, concentrated and purified using ISCO silica gel chromatography (24 g column, gradient from 0% to 100% EtOAc/hexane) to give an intermediate SEM-macrocycle (82 mg, 0.073 mmol, 52.6% yield).

The preceding intermediate SEM macrocycle (82 mg, 0.073 mmol) was dissolved in DCM (5 mL). The solution was purged with $N_2$ before $Pd(Ph_3P)_4$ (7.97 mg, 6.90 μmol) and morpholine (0.060 mL, 0.690 mmol) were added sequentially. The reaction mixture was stirred at RT overnight before it was concentrated and purified using ISCO silica gel chromatography (12 g column, gradient from 0% to 20% MeOH/DCM) to give macrocycle 26 (56 mg, 0.054 mmol, 38.8% yield). LCMS (M+H)=1046.3; $^1$H NMR (400 MHz, CHLOROFORM-d) δ 7.40-7.27 (m, 12H), 5.51 (d, J=10.1 Hz, 2H), 5.11 (d, J=15.4 Hz, 2H), 4.66 (d, J=10.1 Hz, 2H), 4.45 (d, J=15.4 Hz, 2H), 4.35-4.24 (m, 6H), 4.21-4.14 (m, 2H), 4.08-3.99 (m, 2H), 3.79 (d, J=6.8 Hz, 2H), 3.73-3.62 (m, 2H), 3.54 (s, 2H), 3.32-3.13 (m, 4H), 3.04 (s, 2H), 2.30 (br. s., 2H), 2.18 (d, J=6.2 Hz, 4H), 1.95 (br. s., 4H), 1.65 (br. s., 4H), 0.97 (dd, J=4.2, 3.1 Hz, 4H), 0.03 (s, 18H).

To a solution of macrocycle 26 (46 mg, 44 μmol) in THF (1 mL) at −78° C. was added a solution of lithium triethylborohydride (SUPER-HYDRIDE®, 0.13 mL, 0.123 mmol, 1M in THF). The resulting solution was stirred at −78° C. for 2 h before quenching with brine and extracted with $CHCl_3$ (3×). The combined organic layers were dried over $Na_2SO_4$ and concentrated. The residue was then taken up in $CHCl_3$/EtOH (1:1, 2 mL). Silica gel (0.8 g) was added, followed by water (0.6 mL). The resulting suspension was stirred at RT for 24 h and then filtered, washing with 10% MeOH/$CHCl_3$. The filtrate was concentrated and purified using reverse phase HPLC (Column: Phenomenex Luna C18 20×100 mm; Mobile Phase A: 10:90 MeCN:water with 0.1% TFA; Mobile Phase B: 90:10 MeCN:water with 0.1% TFA; Gradient: 10-70% B over 15 min; Flow: 20 mL/min; Detection: UV at 220 nm). to give dimer IIb-5 (20 mg, 24 μmol, 54.3% yield). LCMS (M+H)=754.2; $^1$H NMR (400 MHz, CHLOROFORM-d) δ 7.54 (s, 2H), 7.49 (d, J=5.3 Hz, 2H), 7.42-7.30 (m, 8H), 6.84 (s, 2H), 5.03 (d, J=15.6 Hz, 2H), 4.56 (d, J=15.4 Hz, 2H), 4.37-4.20 (m, 4H), 4.15-4.07 (m, 2H), 4.02-3.94 (m, 2H), 3.36-3.25 (m, 2H), 3.23-3.13 (m, 2H), 3.05-2.95 (m, 6H), 2.42-2.30 (m, 2H), 1.96 (br. s., 8H).

Example 5—Intermediate Compound 48

Figure 5:
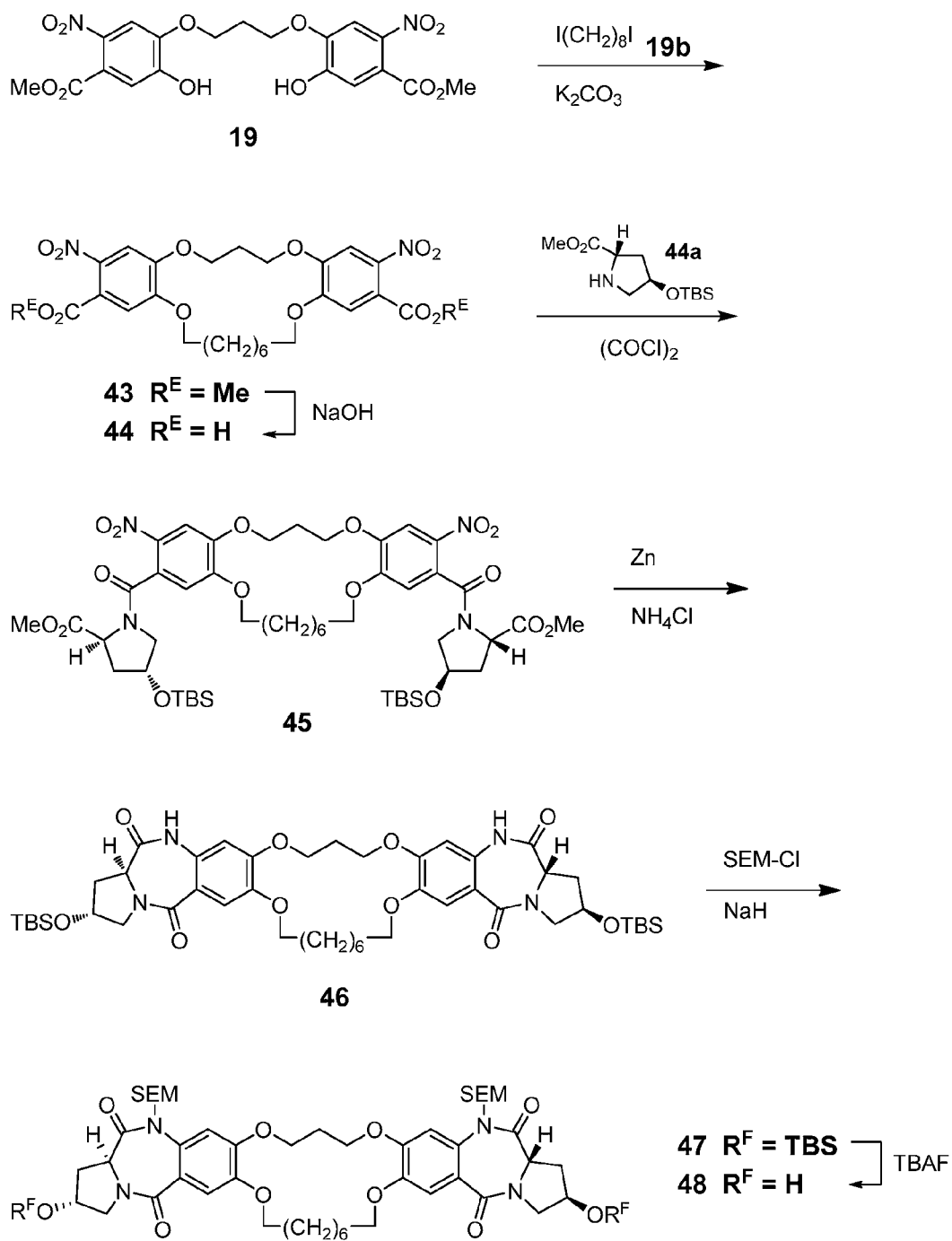

This example pertains to FIG. 5 and the synthesis of intermediate compound 48.

To a RT solution of compound 19 (10.36 g, 22.21 mmol) in DMF (178 mL) was added $K_2CO_3$ (12.28 g, 89 mmol). The mixture was heated to 100° C., then a solution of 1,8-diiodooctane 19b (5.30 mL, 26.7 mmol) in DMF (44.4 mL) was added dropwise over 1.5 h. The reaction mixture was stirred at 100° C. for 3 h more, cooled to RT, and slowly added to a stirred flask of $H_2O$ (2000 mL). The resulting precipitate was collected by vacuum filtration (washed with $H_2O$). The crude material was purified by flash chromatography (220 g silica gel; linear gradient 0-10% EtOAc-DCM) to provide macrocycle 43 (5.994 g, 47%) as a white solid. LC-MS m/z 594 [M+18]$^+$; $^1$H NMR (400 MHz, CDCl$_3$) δ 7.53 (s, 2H), 7.08 (s, 2H), 4.33 (t, J=6.1 Hz, 4H), 4.15 (t, J=5.3 Hz, 4H), 3.91 (s, 6H), 2.36 (quin, J=6.0 Hz, 2H), 1.86-1.78 (m, 4H), 1.61-1.52 (m, 4H), 1.49-1.42 (m, 4H).

To a RT suspension of macrocycle 43 (5.994 g, 10.40 mmol) in THF (78 mL) was added MeOH (26.0 mL) followed by 1 M aq. NaOH (104 mL, 104 mmol). The yellow suspension was stirred at 50° C. for 4 h, gradually becoming a clear yellow solution. The reaction mixture was cooled to RT, partially concentrated, and acidified with 1 M aq. HCl. The resulting solids were collected by vacuum filtration (washed with $H_2O$) to provide macrocycle 44 (5.41 g, 95%) as a yellow solid. LC-MS m/z 566 [M+18]$^+$; $^1$H NMR (400 MHz, DMSO-d$_6$) δ 13.58 (br s, 2H), 7.64 (s, 2H), 7.30 (s, 2H), 4.27 (t, J=6.2 Hz, 4H), 4.16 (t, J=5.1 Hz, 4H), 2.20 (quin, J=6.1 Hz, 2H), 1.74-1.65 (m, 4H), 1.53-1.44 (m, 4H), 1.42-1.32 (m, 4H).

To a RT solution of macrocycle 44 (5.144 g, 9.38 mmol) in THF (94 mL) was added oxalyl chloride (2.140 mL, 22.51 mmol) followed by DMF (7.29 μL, 0.094 mmol). The reaction mixture was stirred at RT for 1 h then concentrated in vacuo. The residue was taken up in THF (94 mL) and cooled to 0° C. NEt$_3$ (7.84 mL, 56.3 mmol) and compound 44a (5.84 g, 22.51 mmol) were added. The cooling bath was removed and the reaction mixture was stirred at RT for 3 h. The reaction was quenched by the addition of a mixture of sat. aq. NH$_4$Cl (250 mL) and H$_2$O (250 mL) and extracted with EtOAc (2×250 mL). The combined organic layers were washed with sat. aq. NaCl (250 mL), dried over Na$_2$SO$_4$, filtered, and concentrated in vacuo. The crude material was purified by flash chromatography (120 g silica gel; linear gradient 0-100% EtOAc-hexanes) to provide compound 45 (9.274 g, 96%) as a yellow foam. LC-MS m/z 1031 [M+H]$^+$.

To a 0° C. solution of compound 45 (9.274 g, 8.99 mmol) in MeOH (56.2 mL) and THF (56.2 mL) was added NH$_4$Cl (9.62 g, 180 mmol) and zinc dust (11.76 g, 180 mmol). The resulting suspension was stirred at 50° C. for 22 h. The reaction was cooled to RT and filtered through CELITE™ (washed with 300 mL EtOAc). The filtrate was concentrated in vacuo. The crude material was taken up in DCM (400 mL), washed with H$_2$O (400 mL), dried over Na$_2$SO$_4$, filtered, and concentrated in vacuo to provide compound 46 (8.2 g, quantitative yield) as a yellow foam. LC-MS m/z 907 [M+H]$^+$; $^1$H NMR (400 MHz, DMSO-d$_6$) δ 10.25 (s, 2H), 7.27 (s, 2H), 6.73 (s, 2H), 4.46 (quin, J=5.2 Hz, 2H), 4.24-4.12 (m, 6H), 4.06-3.96 (m, 4H), 3.60-3.53 (m, 2H), 3.50-3.43 (m, 2H), 2.69-2.56 (m, 2H), 2.26-2.16 (m, 2H), 1.98-1.89 (m, 2H), 1.72-1.62 (m, 4H), 1.54-1.43 (m, 4H), 1.41-1.32 (m, 4H), 0.87-0.83 (m, 18H), 0.08 (s, 12H).

To a 0° C. solution of compound 46 (8.16 g, 8.99 mmol) in DMF (90 mL) was added NaH (1.798 g, 60% w/w in mineral oil, 45.0 mmol). The reaction mixture was stirred at 0° C. for 30 min and SEM-Cl (6.38 mL, 36.0 mmol) was added dropwise. The reaction mixture was stirred at 0° C. for 30 min. Reaction was quenched by the dropwise addition of saturated aq. NH$_4$Cl, followed by warming to RT, dilution with EtOAc (400 mL), washing with H$_2$O (2×400 mL) and sat. aq. NaCl (200 mL), drying over Na$_2$SO$_4$, filtering, and concentrating in vacuo. The crude material was purified by flash chromatography (220 g silica gel; linear gradient 0-100% EtOAc-hexanes) to provide compound 47 (7.980 g, 76%) as a white foam. LC-MS m/z 1168[M+H]$^+$; $^1$H NMR (400 MHz, CDCl$_3$) δ 7.36 (s, 2H), 7.24 (s, 2H), 5.48 (d, J=10.0 Hz, 2H), 4.69 (d, J=9.9 Hz, 2H), 4.58 (quin, J=5.7 Hz, 2H), 4.31-4.21 (m, 6H), 4.19-4.06 (m, 4H), 3.82-3.63 (m, 6H), 3.56 (dd, J=11.9, 5.6 Hz, 2H), 2.90-2.81 (m, 2H), 2.33 (quin, J=6.0 Hz, 2H), 2.07-1.98 (m, 2H), 1.84-1.75 (m, 4H), 1.62-1.54 (m, 4H), 1.50-1.40 (m, 4H), 1.01-0.95 (m, 4H), 0.88 (s, 18H), 0.10 (s, 12H), 0.04 (s, 18H).

To a RT solution of compound 47 (7.979 g, 6.83 mmol) in THF (68.3 mL) was added tetrabutylammonium fluoride (TBAF, 17.08 mL, 1 M solution in THF, 17.08 mmol). The clear yellow solution was stirred at RT for 15 h. The reaction mixture was diluted with DCM (400 mL), washed with H$_2$O (400 mL) and sat. aq. NaCl (400 mL), dried over Na$_2$SO$_4$, filtered, and concentrated in vacuo. The crude material was purified by flash chromatography (120 g silica gel with 25 g prepacked load cartridge; linear gradient 0-10% MeOH—CH$_2$Cl$_2$) to provide compound 48 (5.360 g) as a white foam. The combined aqueous layers from the workup were extracted with DCM (250 mL). The organic layer was dried over Na$_2$SO$_4$, filtered, and concentrated in vacuo. This material was purified by flash chromatography (3×) (80 g silica gel with 25 g prepacked load cartridge; linear gradient 0-10% MeOH—CH$_2$Cl$_2$) to provide an additional 0.617 g compound 48. The two isolates were combined to provide compound 48 (5.997 g, 93%) as a white foam. LC-MS m/z 939 [M+H]$^+$; $^1$H NMR (400 MHz, CDCl$_3$) δ 7.37 (s, 2H), 7.25 (s, 2H), 5.48 (d, J=10.0 Hz, 2H), 4.70 (d, J=10.0 Hz, 2H), 4.69-4.64 (m, 2H), 4.33-4.25 (m, 6H), 4.16-4.03 (m, 4H), 3.85 (dd, J=12.7, 2.1 Hz, 2H), 3.78 (td, J=9.6, 7.1 Hz, 2H), 3.72-3.63 (m, 4H), 2.97 (dt, J=13.6, 5.5 Hz, 2H), 2.32 (quin, J=6.1 Hz, 2H), 2.16-2.07 (m, 2H), 1.95-1.87 (m, 2H), 1.84-1.74 (m, 4H), 1.63-1.53 (m, 4H), 1.48-1.42 (m, 4H), 0.99 (ddd, J=9.5, 6.9, 2.3 Hz, 4H), 0.08--0.01 (m, 18H).

Example 6—Dimers IIc-7 and IIc-8

Figure 6:
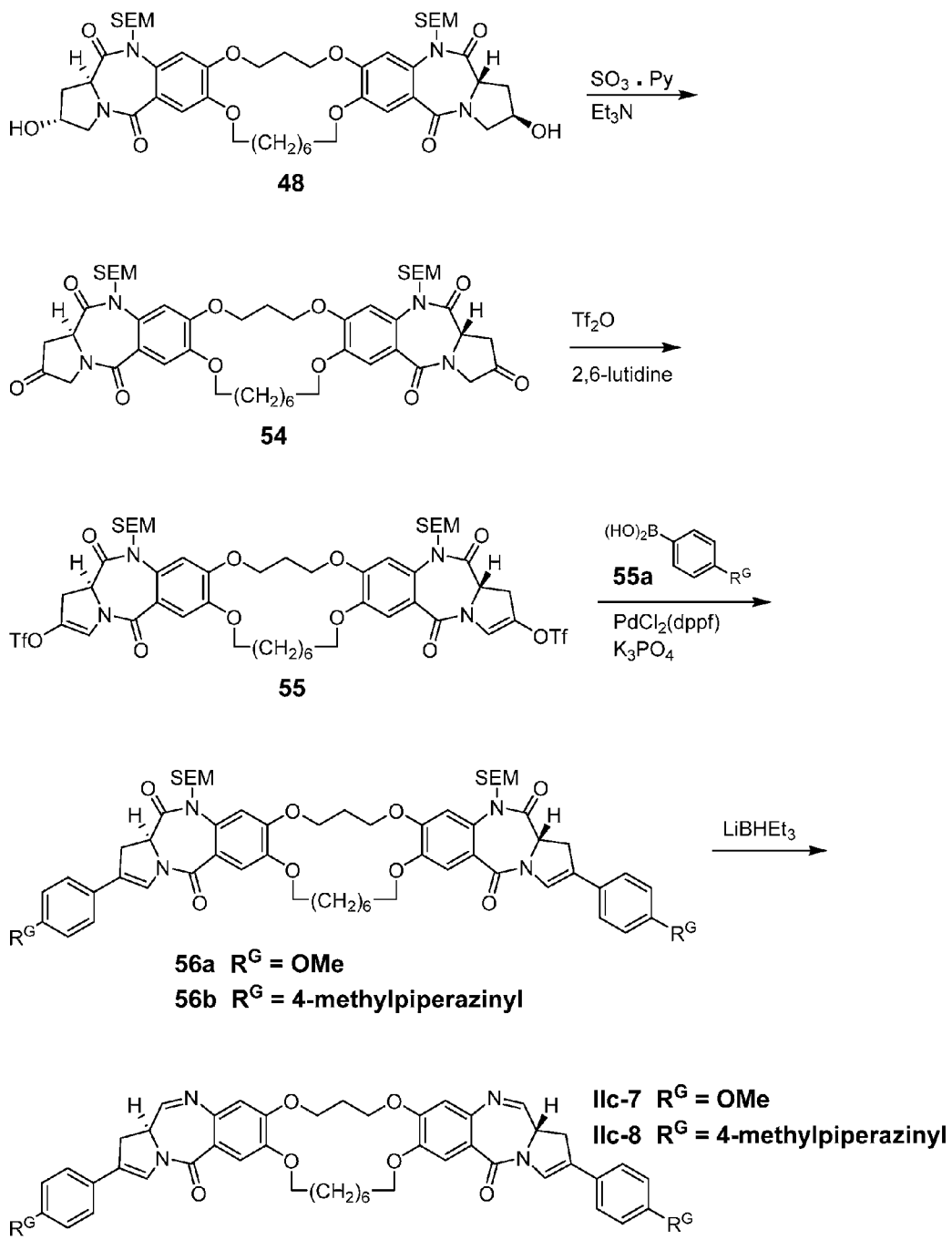

This example pertains to FIG. 6 and the synthesis of dimers IIc-7 and IIc-8.

To a 0° C. solution of compound 48 (5.997 g, 6.38 mmol) in DCM (31.9 mL) and DMSO (31.9 mL) was added NEt$_3$ (8.90 mL, 63.8 mmol) followed by SO$_3$-pyridine complex (4.06 g, 25.5 mmol). The reaction was allowed to warm to RT as it was stirred for 16 h. The reaction was diluted with DCM (400 mL), washed with sat. aq. NH$_4$Cl (400 mL), H$_2$O (2×400 mL), and sat. aq. NaHCO$_3$ (400 mL), dried over Na$_2$SO$_4$, filtered, and concentrated in vacuo. The crude material was purified by flash chromatography (120 g silica gel with 25 g prepacked load cartridge; linear gradient 0-100% EtOAc—CH$_2$Cl$_2$) to provide compound 54 (4.822 g, 81%) as a white foam. LC-MS m/z 935 [M+H]$^+$; $^1$H NMR (400 MHz, CDCl$_3$) δ 7.36 (s, 2H), 7.28 (s, 2H), 5.52 (d, J=10.1 Hz, 2H), 4.76 (d, J=10.0 Hz, 2H), 4.65 (dd, J=9.8, 3.0 Hz, 2H), 4.36-4.28 (m, 4H), 4.28-4.20 (m, 2H), 4.18-4.06 (m, 4H), 3.94-3.86 (m, 2H), 3.78 (td, J=9.8, 6.7 Hz, 2H), 3.69 (td, J=9.8, 6.6 Hz, 2H), 3.58 (dd, J=19.1, 2.9 Hz, 2H), 2.85-2.73 (m, 2H), 2.39-2.31 (m, 2H), 1.86-1.77 (m, 4H), 1.64-1.53 (m, 4H), 1.50-1.42 (m, 4H), 0.99 (ddd, 6.6, 4.7 Hz, 4H), 0.04 (s, 18H).

To a −78° C. solution of compound 54 (4.822 g, 5.16 mmol) in DCM (129 mL) was added 2,6-lutidine (3.72 mL, 32.0 mmol) and trifluoromethanesulfonic anhydride (Tf$_2$O, 30.9 mL, 1 M solution in DCM, 30.9 mmol) dropwise over 30 min. The bright yellow solution was allowed to warm to −20° C. over 1.5 h, then it was stirred at −20° C. for an additional 1 h. The reaction was diluted with sat. aq. NaHCO$_3$ (400 mL) and extracted with DCM (2×200 mL). The combined organic layers were washed with H$_2$O (200 mL), dried over Na$_2$SO$_4$, filtered, and concentrated in vacuo. The crude material was purified by flash chromatography (2×) (120 g silica gel with 25 g prepacked load cartridge; linear gradient 0-100% EtOAc-hexanes) to provide compound 55 (4.018 g, 65%) as an orange foam. $^1$H NMR (400 MHz, DMSO-d$_6$) δ 7.38 (t, J=2.0 Hz, 2H), 7.28 (s, 2H), 7.25 (s, 2H), 5.33-5.26 (m, 2H), 5.21 (d, J=10.5 Hz, 2H), 4.91 (dd, J=10.8, 3.5 Hz, 2H), 4.31-4.18 (m, 4H), 4.10-4.03 (m, 4H), 3.65-3.57 (m, 2H), 3.53-3.38 (m, 4H), 3.18 (ddd, J=16.3, 11.0, 2.1 Hz, 2H), 2.26-2.18 (m, 2H), 1.75-1.66 (m, 4H), 1.55-1.46 (m, 4H), 1.44-1.35 (m, 4H), 0.85-0.70 (m, 4H), −0.08 (s, 18H).

A mixture of compound 55 (65 mg, 0.054 mmol), (4-methoxyphenyl)boronic acid (18.12 mg, 0.119 mmol), and [1,1'-bis(diphenylphosphino)ferrocene]dichloropalladium(II) (PdCl$_2$(dppf), 1.983 mg, 2.71 μmol) was evacuated and backfilled with N$_2$, then THF (1084 μL) and tribasic potassium phosphate (542 μL, 0.5 M solution in H$_2$O, 0.271 mmol) were added. The mixture was sparged with N$_2$ for 5 min then stirred at RT for 1.5 h. The reaction was diluted with EtOAc (50 mL) and washed with sat. aq. NaHCO$_3$ (50 mL) and sat. aq. NaCl (50 mL), dried over Na$_2$SO$_4$, filtered, and concentrated in vacuo. The crude material was purified by flash chromatography (24 g silica gel with 5 g prepacked load cartridge; linear gradient 0-100% EtOAc-hexanes) to provide compound 56a (50.3 mg, 83%) as a white foam. LC-MS m/z 1116 [M+H]$^+$; $^1$H NMR (400 MHz, CDCl$_3$) δ 7.42 (s, 2H), 7.40-7.36 (m, 4H), 7.34-7.32 (m, 2H), 7.29 (s, 2H), 6.91-6.87 (m, 4H), 5.53 (d, J=10.1 Hz, 2H), 4.76 (d, J=10.1 Hz, 2H), 4.65 (dd, J=10.5, 3.4 Hz, 2H), 4.32 (t, J=6.2 Hz, 4H), 4.19-4.06 (m, 4H), 3.98-3.91 (m, 2H), 3.83 (s, 6H), 3.84-3.77 (m, 2H), 3.71 (td, J=9.6, 7.0 Hz, 2H), 3.15 (ddd, J=16.1, 10.7, 2.1 Hz, 2H), 2.35 (quin, J=5.9 Hz, 2H), 1.85-1.77 (m, 4H), 1.64-1.55 (m, 4H), 1.50-1.42 (m, 4H), 1.00 (ddd, J=9.5, 7.0, 2.2 Hz, 4H), 0.04 (s, 18H).

To a −78° C. solution of compound 56a (50.3 mg, 0.045 mmol) in THF (1503 μL) was added lithium triethylborohydride (225 μL, 1 M solution in THF, 0.225 mmol) dropwise. The reaction mixture was stirred at −78° C. for 1 h. The reaction mixture was diluted with H$_2$O (10 mL) and extracted with DCM (2×10 mL). The combined organic layers were dried over Na$_2$SO$_4$, filtered, and concentrated in vacuo. The residue was taken up in CHCl$_3$ (1.0 mL) and EtOH (1.0 mL), then silica gel (0.50 g) and H$_2$O (0.50 mL) were added. The reaction was stirred at RT for 3 days. The mixture was filtered through CELITE™ (washed with CHCl$_3$) and the filtrate was concentrated in vacuo. The crude material was purified by preparative HPLC (3 injections, each in 2 mL of DMSO; Phenomenex Luna C18 21.2×100 mm; linear gradient 42-90% MeCN—H$_2$O with 0.1% v/v TFA over 12 min; 20 mL/min; 220 nm detection). The product-containing fractions were immediately diluted with sat. aq. NaHCO$_3$ (100 mL) and extracted with CHCl$_3$ (2×50 mL). The combined organic layers were dried over MgSO$_4$, filtered, and concentrated in vacuo to provide dimer IIc-7 (6.0 mg, 15%) as a orange solid. LC-MS m/z 823 [M+H]$^+$; $^1$H NMR (400 MHz, CDCl$_3$) δ 7.89 (d, J=4.0 Hz, 2H), 7.54 (s, 2H), 7.40 (s, 2H), 7.37-7.33 (m, 4H), 6.94-6.89 (m, 4H), 6.88 (s, 2H), 4.47-4.40 (m, 2H), 4.39-4.25 (m, 4H), 4.22-4.16 (m, 2H), 4.14-4.05 (m, 2H), 3.84 (s, 6H), 3.59 (ddd, J=16.3, 11.5, 1.9 Hz, 2H), 3.43-3.34 (m, 2H), 2.42-2.29 (m, 2H), 1.86-1.76 (m, 4H), 1.64-1.55 (m, 4H), 1.49-1.43 (m, 4H).

Dimer IIc-8 was prepared analogously according to the synthetic procedures described above for dimer IIc-7. The analytical data for dimer IIc-8 were: LC-MS m/z 960 [M+H]$^+$; $^1$H NMR (400 MHz, CDCl$_3$) δ 7.88 (d, J=4.0 Hz, 2H), 7.55-7.52 (m, 2H), 7.39-7.36 (m, 2H), 7.34-7.30 (m, 4H), 6.94-6.90 (m, 4H), 6.89-6.87 (m, 2H), 4.45-4.38 (m, 2H), 4.37-4.25 (m, 4H), 4.21-4.15 (m, 2H), 4.14-4.05 (m, 2H), 3.62-3.53 (m, 2H), 3.42-3.33 (m, 2H), 3.29-3.22 (m, 8H), 2.62-2.56 (m, 8H), 2.37 (s, 6H), 2.38-2.30 (m, 2H), 1.84-1.76 (m, 4H), 1.62-1.52 (m, 4H), 1.48-1.40 (m, 4H).

Example 7—Dimers IIc-9, IIc-10, IIc-11, and IId-1

This example pertains to FIG. 7 and the synthesis of dimers IIc-9, IIc-10, IIc-11 and IId-1.

A mixture of compound 55 (0.51 g, 0.425 mmol), (4-aminophenyl)boronic acid (58 mg, 0.425 mmol), and PcCl$_2$(dppf) (16 mg, 21 μmol) was evacuated and backfilled with N$_2$. THF (8.5 mL) and tribasic potassium phosphate (4.25 mL, 0.5 M solution in H$_2$O, 2.126 mmol) were added. The mixture was sparged with N$_2$ for 5 min then stirred at RT for 1 h. The reaction mixture was diluted with DCM (30 mL), washed with sat. aq. NaCl (30 mL), dried over Na$_2$SO$_4$, filtered, and concentrated in vacuo. The crude material was purified by flash chromatography (40 g column; linear gradient 0-100% EtOAc-hexanes) to provide compound 57b (205 mg, 42%) as a yellow foam. LC-MS m/z 1142 [M+H]$^+$.

A mixture of compound 57b (70 mg, 0.061 mmol), (4-methoxyphenyl)boronic acid (12.1 mg, 0.080 mmol), and PcCl$_2$(dppf) (2.24 mg, 3.1 μmol) was evacuated and backfilled with N$_2$. THF (1226 μL) and tribasic potassium phosphate (613 μL, 0.5 M solution in H$_2$O, 0.306 mmol) were added. The mixture was sparged with N$_2$ for 5 min then stirred at RT for 30 min. The reaction was diluted with EtOAc (30 mL), washed with sat. aq. NaCl (30 mL), dried over Na$_2$SO$_4$, filtered, and concentrated in vacuo. The crude material was purified by flash chromatography (40 g column; linear gradient 0-100% EtOAc-hexanes) to provide compound 58a (60 mg, 89%) as a yellow foam. LC-MS m/z 1100.8 [M+H]$^+$.

Alternatively to using a boronic acid, a Grignard reagent can be used, as illustrated by the following synthesis of compound 58d from compound 57b: To a –30° C. solution of compound 57b (112 mg, 0.098 mmol) and iron(III) acetylacetonate (3.46 mg, 9.80 μmol) in THF (1334 μL) and NMP (66.7 μL) was added methylmagnesium bromide (131 μL, 3.0 M solution in Et$_2$O, 0.392 mmol), dropwise slowly. The reaction was stirred at –30° C. for 10 min, then it was quenched by the addition of sat. aq. NH$_4$Cl (30 mL) and extracted with EtOAc (2×30 mL). The combined organic layers were washed with sat. aq. NaCl (30 mL), dried over Na$_2$SO$_4$, filtered, and concentrated in vacuo. The crude material was purified by flash chromatography (12 g silica gel with 5 g prepacked load cartridge; linear gradient 0-100% EtOAc—CH$_2$Cl) to provide compound 58d (50 mg, 51%) as a yellow foam. LC-MS m/z 1008 [M+H]$^+$; $^1$H NMR (400 MHz, CDCl$_3$) δ 7.42-7.38 (m, 2H), 7.29-7.24 (m, 5H), 6.70-6.64 (m, 3H), 5.55-5.48 (m, 2H), 4.77-4.71 (m, 2H), 4.62 (dd, J=10.6, 3.2 Hz, 1H), 4.48 (dd, J=10.4, 3.3 Hz, 1H), 4.35-4.27 (m, 4H), 4.18-4.05 (m, 4H), 3.95-3.88 (m, 1H), 3.84-3.64 (m, 6H), 3.49-3.42 (m, 1H), 3.12 (ddd, J=16.1, 10.5, 2.0 Hz, 1H), 2.83-2.72 (m, 1H), 2.34 (quin, J=6.0 Hz, 2H), 1.84 (d, J=1.1 Hz, 3H), 1.83-1.76 (m, 4H), 1.63-1.56 (m, 4H), 1.49-1.43 (m, 4H), 0.99 (ddd, J=9.6, 6.9, 2.4 Hz, 4H), 0.04 (s, 18H).

To a –78° C. solution of the crude compound 58a (30 mg, 0.027 mmol) in THF (1 mL) was added lithium triethylborohydride (273 μL, 1 M solution in THF, 0.273 mmol) dropwise. The reaction was stirred at –78° C. for 1 h. The reaction was diluted with brine and extracted with EtOAc (3×). The combined organic layers were dried over Na$_2$SO$_4$, filtered, and concentrated in vacuo. The crude material was taken up in EtOH/THF (1:1, 2 mL) and aq. formic acid (0.055, 1 mL). The resulting solution was stirred at RT for 2 h before it was neutralized with aq. NaHCO$_3$. The resulting mixture was extracted with chloroform (3×). The combined organic layers were dried over Na$_2$SO$_4$, filtered, and concentrated in vacuo. The crude product was then purified by flash chromatography (12 g column, 0-10% MeOH/DCM) to give dimer IIc-11 (11 mg, 45%). LC-MS m/z 808.4 [M+H]$^+$.

Dimers IIc-9, IIc-10, and IId-1 were analogously prepared according to the synthetic procedures described for above for dimer IIc-11. Their analytical data is provided below.

Dimer IIc-9: LC-MS m/z 876 [M+H]$^+$; $^1$H NMR (400 MHz, CDCl$_3$) δ 7.90-7.86 (m, 2H), 7.56-7.52 (m, 2H), 7.39-7.36 (m, 1H), 7.35-7.33 (m, 1H), 7.31 (d, J=8.6 Hz, 2H), 7.22 (d, J=8.6 Hz, 2H), 6.92 (d, J=9.0 Hz, 2H), 6.88 (s, 2H), 6.68 (d, J=8.6 Hz, 2H), 4.45-4.37 (m, 2H), 4.36-4.25 (m, 4H), 4.22-4.15 (m, 2H), 4.13-4.06 (m, 2H), 3.79-3.69 (m, 2H), 3.63-3.52 (m, 2H), 3.41-3.32 (m, 2H), 3.31-3.23 (m, 4H), 2.65-2.57 (m, 4H), 2.38 (s, 3H), 2.41-2.30 (m, 2H), 1.84-1.76 (m, 4H), 1.62-1.54 (m, 4H), 1.49-1.40 (m, 4H).

Dimer IIc-10: LC-MS m/z 946 [M+H]$^+$; $^1$H NMR (400 MHz, CDCl$_3$) δ 7.88 (d, J=4.0 Hz, 2H), 7.56-7.51 (m, 2H), 7.39-7.36 (m, 2H), 7.35-7.29 (m, 4H), 6.94-6.90 (m, 4H), 6.89-6.86 (m, 2H), 4.45-4.38 (m, 2H), 4.37-4.24 (m, 4H), 4.22-4.15 (m, 2H), 4.13-4.05 (m, 2H), 3.62-3.52 (m, 2H), 3.42-3.33 (m, 2H), 3.29-3.22 (m, 4H), 3.22-3.15 (m, 4H), 3.07-3.02 (m, 4H), 2.61-2.55 (m, 4H), 2.39-2.29 (m, 6H), 1.84-1.76 (m, 4H), 1.64-1.51 (m, 4H), 1.48-1.40 (m, 4H).

Dimer IId-1: LC-MS 716 [M+H]$^+$; $^1$H NMR (400 MHz, CDCl$_3$) δ 7.87 (d, J=4.0 Hz, 1H), 7.80 (d, J=4.0 Hz, 1H), 7.55-7.50 (m, 2H), 7.35-7.32 (m, 1H), 7.24-7.20 (m, 2H), 6.88-6.84 (m, 2H), 6.76-6.73 (m, 1H), 6.70-6.66 (m, 2H), 4.44-4.36 (m, 1H), 4.35-4.22 (m, 5H), 4.22-4.14 (m, 2H), 4.13-4.05 (m, 2H), 3.84-3.69 (m, 2H), 3.61-3.48 (m, 1H), 3.40-3.31 (m, 1H), 3.23-3.11 (m, 1H), 3.00-2.91 (m, 1H), 2.34 (quin, J=6.1 Hz, 2H), 1.84 (d, J=1.1 Hz, 3H), 1.82-1.75 (m, 4H), 1.63-1.53 (m, 4H), 1.48-1.40 (m, 4H).

Example 8—Dimer IIb-6

Figure 8:
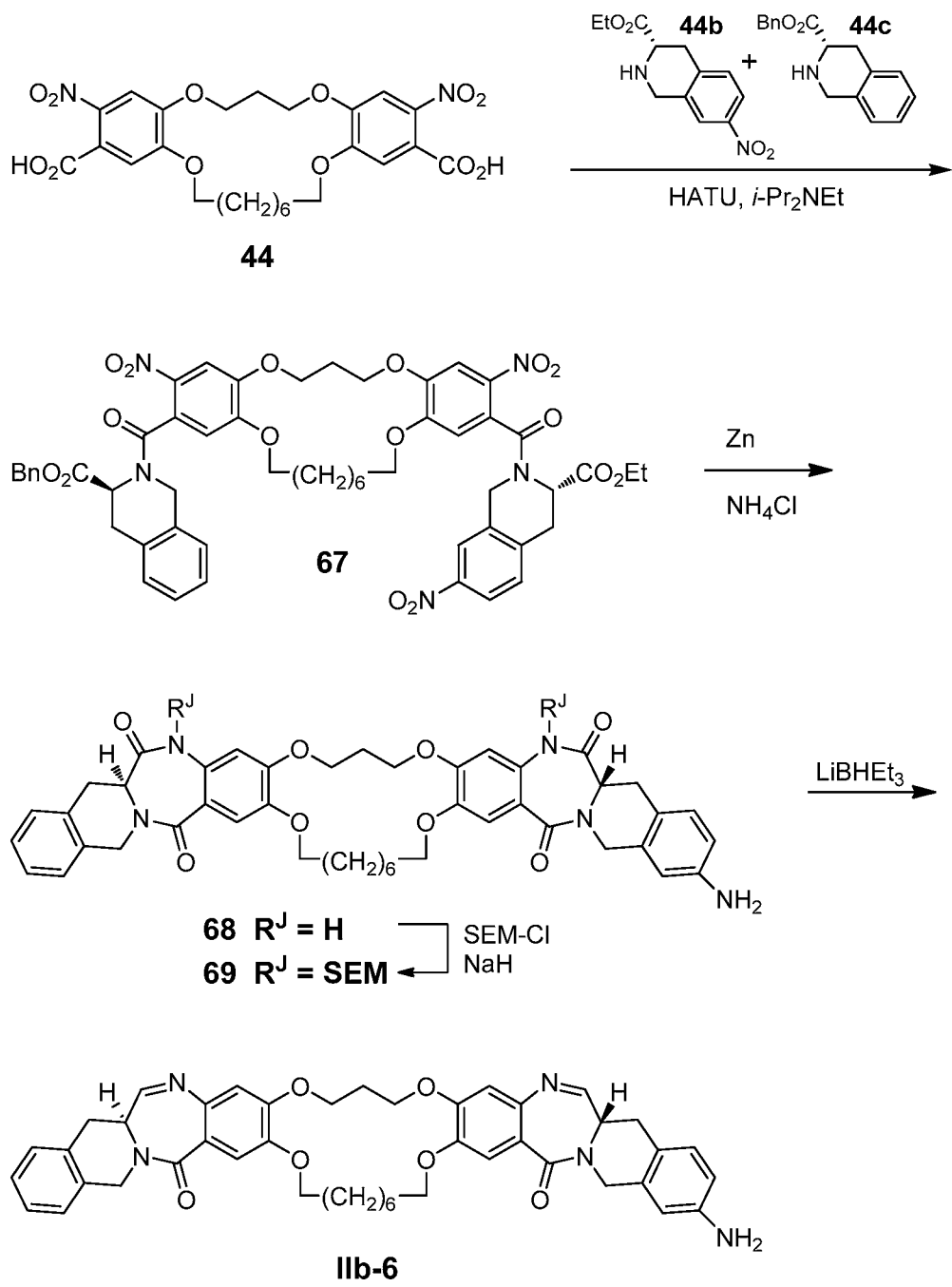

This example pertains to FIG. 8 and the synthesis of dimer IIb-6.

To a RT solution of compound 44 (1.006 g, 1.834 mmol) in DMF (12.23 mL) was added N,N,N',N'-tetramethyl-O-(7-azabenzotriazol-1-yl)uronium hexafluorophosphate (HATU, 1.743 g, 4.59 mmol) followed by (S)-ethyl 7-nitro-1,2,3,4-tetrahydroisoquinoline-3-carboxylate 44b (0.459 g, 1.834 mmol) portionwise, and then N,N-diisopropylethylamine (DIEA, 1.917 mL, 11.00 mmol) dropwise. The resulting clear brown solution was stirred at RT for 30 min, then (S)-benzyl 1,2,3,4-tetrahydroisoquinoline-3-carboxylate 4-methylbenzenesulfonate 44c (0.806 g, 1.834 mmol) was added. The reaction was stirred at RT for an additional 1 h. The reaction mixture was slowly added to a stirred flask of H$_2$O (125 mL) at 0° C. and the resulting precipitate was collected by vacuum filtration (washed with H$_2$O). The solids were dissolved in EtOAc (200 mL), washed with sat. aq. NaCl (150 mL), dried over Na$_2$SO$_4$, filtered, and concentrated in vacuo. The crude material was purified by flash chromatography (220 g RediSep Gold silica gel with 25 g prepacked load cartridge; linear gradient 0-100% EtOAc-hexanes) to provide compound 67 (538 mg, 29%) as a brown foam. LC-MS m/z 1030 [M+H]$^+$.

To a RT solution of compound 67 (538 mg, 0.522 mmol) in MeOH (3264 μL) and THF (3264 μL) was added NH₄Cl (559 mg, 10.45 mmol), zinc dust (683 mg, 10.45 mmol), and HOAc (1 drop). The resulting suspension was stirred at 60° C. for 18 h. The reaction was cooled to RT and filtered through CELITE™ (washed with EtOAc, DCM, MeOH, and %5 v/v Et₃N in DCM). The filtrate was concentrated in vacuo. The crude material was taken up in DCM (200 mL), washed with sat. aq. NaHCO₃ (200 mL) and H₂O (200 mL), dried over Na₂SO₄, filtered, and concentrated in vacuo to provide compound 68 (250 mg, 61%) as an orange solid. LC-MS m/z 786 [M+H]⁺.

To a 0° C. solution of compound 68 (250 mg, 0.318 mmol) in DMF (3181 μL) was added NaH (63.6 mg, 60% w/w in mineral oil, 1.591 mmol). The reaction was stirred at 0° C. for 30 min, then SEM-Cl (226 μL, 1.272 mmol) was added. The reaction was stirred at 0° C. for 30 min. The reaction was quenched by the addition of sat. aq. NH₄Cl, then it was warmed to RT, diluted with EtOAc (100 mL), washed with H₂O (100 mL) and sat. aq. NaCl (100 mL), dried over Na₂SO₄, filtered, and concentrated in vacuo. The crude material was purified by flash chromatography (40 g silica gel with 5 g prepacked load cartridge; linear gradient 0-10% MeOH—CH₂Cl₂) to provide compound 69 (289 mg, 87%) as a yellow foam. LC-MS m/z 1047 [M+H]⁺.

To a −78° C. solution of compound 69 (43.9 mg, 0.042 mmol) in THF (1398 μL) was added lithium triethylborohydride (210 μL, 1 M solution in THF, 0.210 mmol) dropwise. The reaction was stirred at −78° C. for 1.5 h. The reaction was diluted with H₂O (10 mL) and extracted with CHCl₃ (2×10 mL). The combined organic layers were dried over Na₂SO₄, filtered, and concentrated in vacuo. The residue was taken up in CHCl₃ (1 mL) and EtOH (1 mL), then silica gel (0.5 g) and H₂O (0.5 mL) were added. The reaction was stirred at RT for 2 days. The mixture was filtered through CELITE™ (washed with acetone, CHCl₃, and 10% MeOH—CHCl₃) and the filtrate was concentrated in vacuo. This material was taken up in CHCl₃ and H₂O and the layers were separated. The aqueous layer was extracted with CHCl₃, dried over Na₂SO₄, filtered, and concentrated in vacuo. The crude material was purified by preparative HPLC (2 injections, each in 2 mL of 1:1 MeCN-DMSO; Phenomenex Luna C18 21.2×100 mm; linear gradient 26-90% MeCN—H₂O with 0.1% v/v TFA over 12 min; 20 mL/min; 220 nm detection). The product-containing fractions were immediately diluted with sat. aq. NaHCO₃ (100 mL) and extracted with CHCl₃ (2×50 mL). The combined organic layers were dried over Na₂SO₄, filtered, and concentrated in vacuo to provide dimer IIb-6 (6.6 mg, 19%) as an off-white solid. LC-MS m/z 754 [M+H]⁺; ¹H NMR (400 MHz, CDCl₃) δ 7.54-7.52 (m, 2H), 7.49-7.45 (m, 2H), 7.39-7.29 (m, 4H), 7.13 (d, J=8.1 Hz, 1H), 6.86-6.83 (m, 2H), 6.66-6.62 (m, 2H), 5.01 (d, J=15.6 Hz, 1H), 4.90 (d, J=15.6 Hz, 1H), 4.56 (d, J=15.6 Hz, 1H), 4.44 (d, J=15.4 Hz, 1H), 4.35-4.23 (m, 4H), 4.22-4.15 (m, 2H), 4.08 (dt, J=9.6, 4.9 Hz, 2H), 3.98-3.93 (m, 1H), 3.92-3.87 (m, 1H), 3.78-3.65 (m, 2H), 3.31-3.24 (m, 1H), 3.20-3.12 (m, 2H), 3.05-2.99 (m, 1H), 2.33 (quin, J=6.1 Hz, 2H), 1.84-1.74 (m, 4H), 1.62-1.50 (m, 4H), 1.48-1.39 (m, 4H).

Example 9—Dimer IId-2

Figure 9:
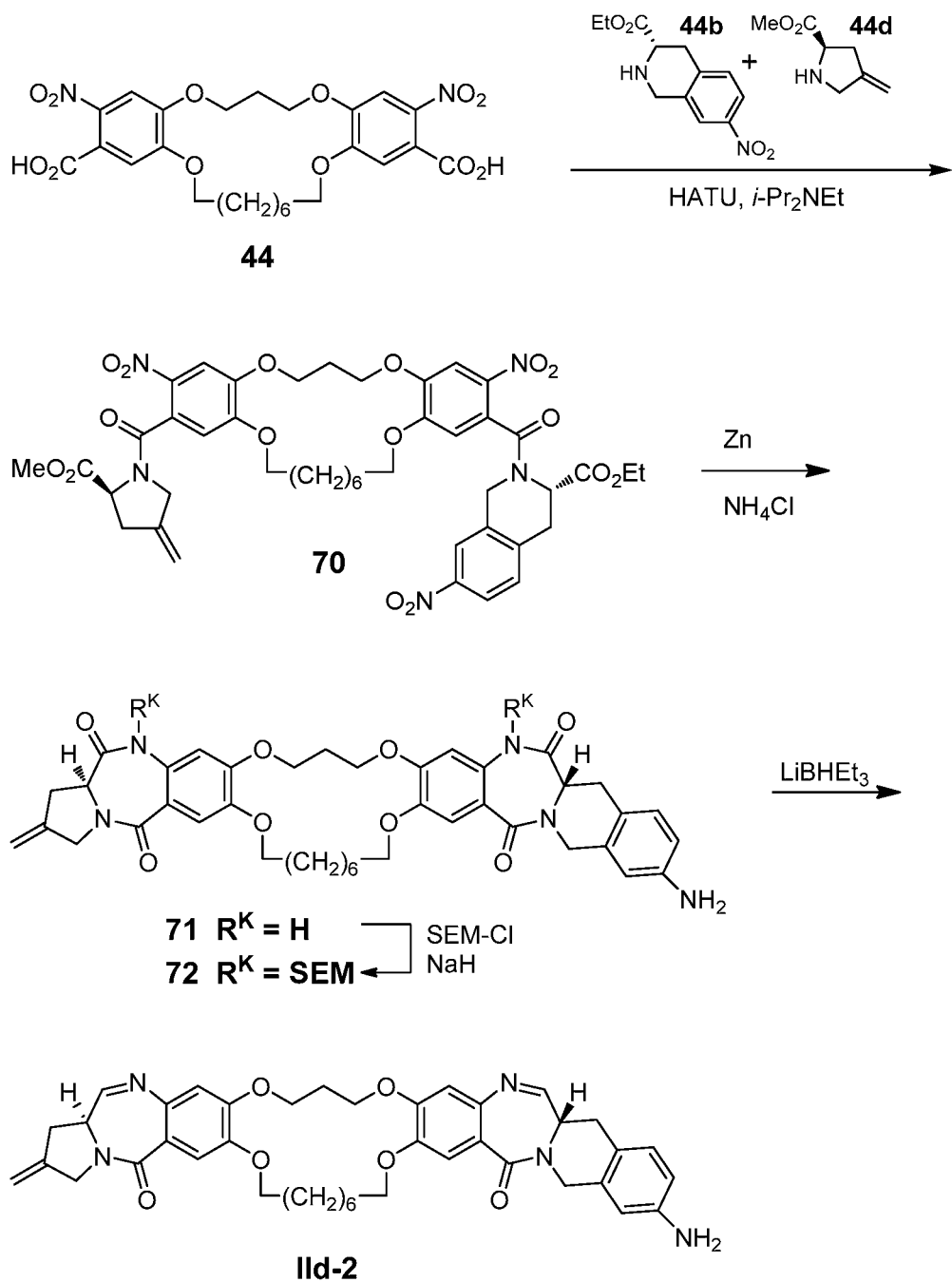

This example pertains to FIG. 9 and the synthesis of dimer IId-2.

Following the reaction scheme shown in FIG. 9, dimer IId-2 was synthesized analogously to the procedures of the previous example. LC-MS m/z 704 [M+H]⁺.

Example 10—Dimers IId-3 and IId-4

Figure 10:
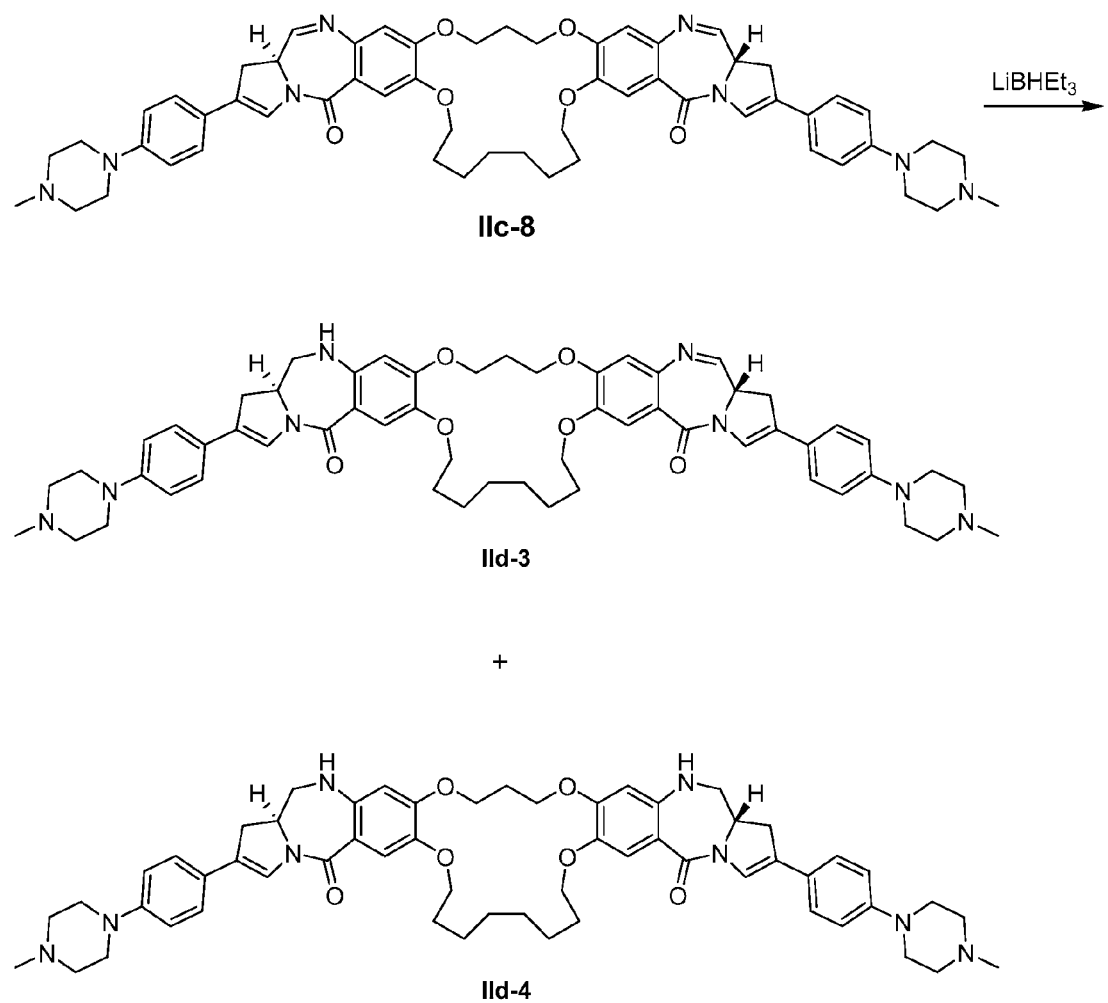

This example pertains to FIG. 10 and the synthesis of dimers IId-3 and IId-4.

To a −78° C. suspension of dimer IIc-8 (46.2 mg, 0.048 mmol) in THF (482 μL) was added LiBHEt₃ (48.2 μL, 1 M solution in THF, 0.048 mmol), dropwise. The reaction mixture was stirred at −78° C. for 15 min. Then it was quenched by the addition of H₂O, warmed to RT, diluted with sat. aq. NaHCO₃ (25 mL) and H₂O (25 mL), and extracted with 10% MeOH—CHCl₃ (2×50 mL). The combined organic layers were dried over Na₂SO₄, filtered, and concentrated in vacuo. The crude material was purified by preparative HPLC (4 1-mL injections in DMSO; Phenomenex Luna C18 21.2×100 mm; linear gradient 0-50% MeCN—H₂O w/0.05% v/v HCO₂H over 25 min; 20 mL/min; 220 nm detection). The fractions containing the mono- and bis-reduced products were separately lyophilized then repurified by preparative HPLC to provide dimer IId-3 (2.7 mg, 6%) as a light yellow solid and dimer IId-4 (1.24 mg, 3%), also as a light yellow solid. Their analytical data is presented below.

Dimer IId-3: LC-MS m/z 961 [M+H]⁺; ¹H NMR (400 MHz, CDCl₃) δ 7.87 (d, J=4.0 Hz, 1H), 7.56 (s, 1H), 7.54-7.52 (m, 1H), 7.52-7.50 (m, 1H), 7.39-7.37 (m, 1H), 7.34-7.29 (m, 4H), 6.94-6.86 (m, 5H), 6.13 (s, 1H), 4.41 (dt, J=11.1, 4.7 Hz, 1H), 4.37-4.22 (m, 5H), 4.18 (dt, J=9.8, 5.1 Hz, 1H), 4.13-3.96 (m, 3H), 3.62-3.52 (m, 3H), 3.41-3.32 (m, 2H), 3.31-3.24 (m, 8H), 2.75-2.69 (m, 1H), 2.70-2.64 (m, 8H), 2.41 (s, 6H), 2.35-2.28 (m, 2H), 1.84-1.70 (m, 4H), 1.62-1.51 (m, 4H), 1.47-1.38 (m, 4H).

Dimer IId-4: LC-MS m/z 963 [M+H]⁺; ¹H NMR (400 MHz, CDCl₃) δ 7.56 (s, 2H), 7.51-7.50 (m, 2H), 7.30-7.26 (m, 4H), 6.90 (d, J=8.8 Hz, 4H), 6.10 (s, 2H), 4.36-4.29 (m, 2H), 4.24-4.17 (m, 4H), 4.10-3.97 (m, 4H), 3.59-3.50 (m, 4H), 3.40-3.32 (m, 2H), 3.27-3.21 (m, 8H), 2.72 (dd, J=16.0, 3.4 Hz, 2H), 2.62-2.55 (m, 8H), 2.36 (s, 6H), 2.34-2.26 (m, 2H), 1.77-1.68 (m, 4H), 1.64-1.50 (m, 4H), 1.43-1.36 (m, 4H).

Example 11—Dimer-Linker IIIa-1

Figure 11:
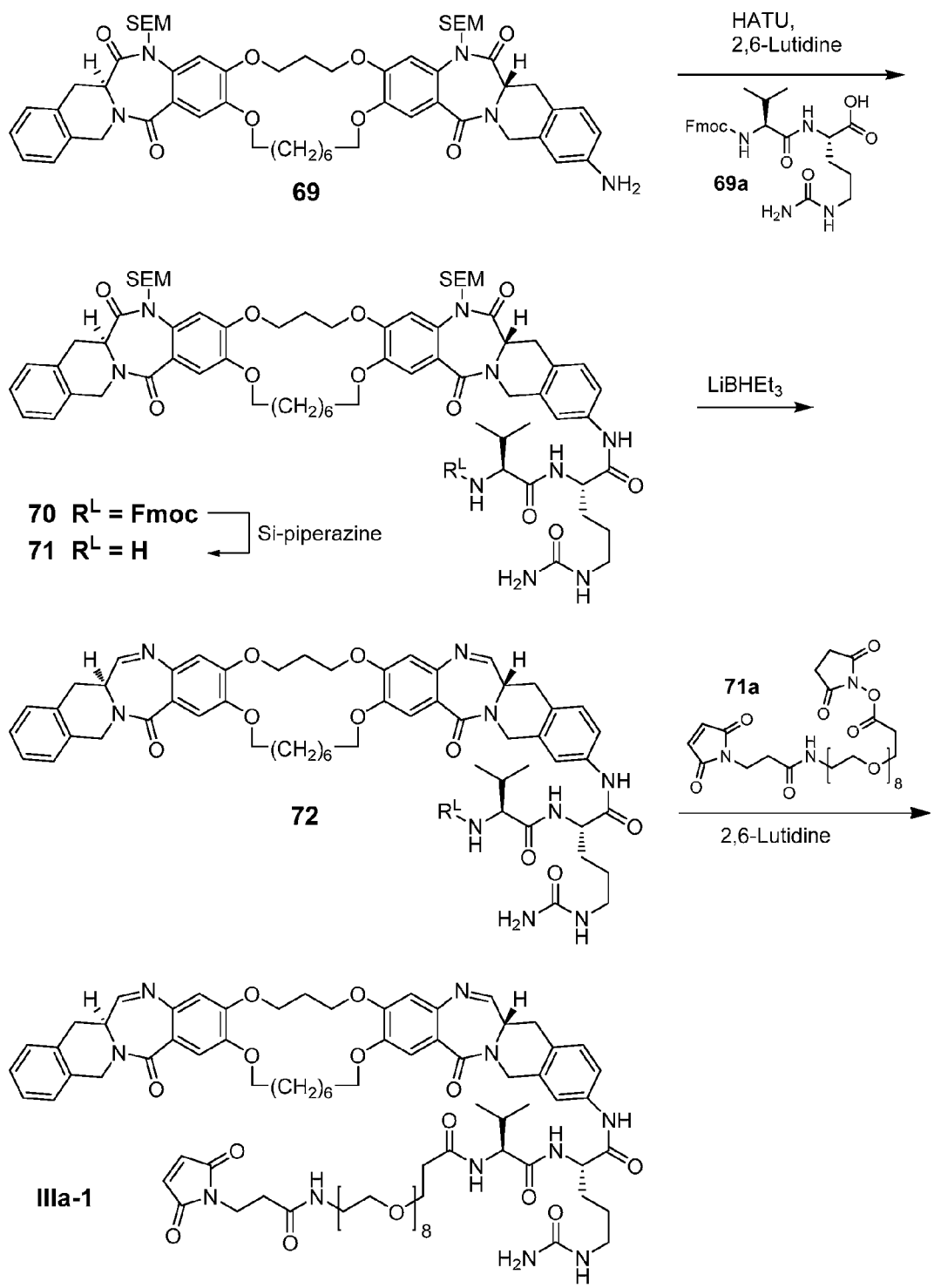

This example pertains to FIG. 11 and the synthesis of dimer-linker IIIa-1.

To a 0° C. mixture of dipeptide 69a (70.4 mg, 0.142 mmol) and HATU (53.9 mg, 0.142 mmol) was added DMF (945 μL). The mixture was stirred at 0° C. for 10 min and 2,6-lutidine (22.02 μL, 0.189 mmol) was added. This mixture was added dropwise to compound 69 (98.9 mg, 0.095 mmol) in a vial at 0° C. The reaction was allowed to warm to RT as it was stirred for 22 h. Then it was added dropwise to a stirred flask of H₂O (20 mL) in a 0° C. bath. The precipitate was collected by vacuum filtration (washed with H₂O), taken up in DCM (50 mL), and washed with H₂O (50 mL). The aqueous layer was extracted with DCM (50 mL). The combined organic layers were dried over Na₂SO₄, filtered, and concentrated in vacuo. The crude material was purified by flash chromatography (24 g silica gel with 5 g prepacked load cartridge; linear gradient 0-10% MeOH- DCM). The mixed fractions were repurified by flash chromatography (24 g RediSep Gold silica gel with 5 g prepacked load cartridge; linear gradient 0-10% MeOH—$CH_2Cl$) and the products of the two columns were combined to provide compound 70 (68.8 mg, 48%). LC-MS m/z 1525 $[M+H]^+$.

To a RT solution of compound 70 (39.9 mg, 0.026 mmol) in DMF (1047 μL) was added silica-supported piperazine (575 mg, 0.91 mmol/g loading, 0.523 mmol). The suspension was stirred at RT for 18 h, then it was filtered (washed with ~2 mL DMF), and the filtrate was concentrated in vacuo. This crude compound 71 was combined with crude compound 71 from another batch (0.019 mmol scale) and used without further purification. LC-MS m/z 1303 $[M+H]^+$.

To a −78° C. solution of crude compound 71 in THF (1356 μL) was added $LiBHEt_3$ (203 μL, 1 M solution in THF, 0.203 mmol), dropwise. The reaction was stirred at −78° C. for 1.5 h, then it was diluted with sat. aq. NaCl (50 mL) and extracted with DCM (2×50 mL). The combined organic layers were dried over $Na_2SO_4$, filtered, and concentrated in vacuo. The residue was taken up in $CHCl_3$ (1 mL) and EtOH (1 mL), then silica gel (0.5 g) and $H_2O$ (0.5 mL) were added. The reaction mixture was stirred at RT for 2 days, then it was filtered through CELITE™ (washed with 10% EtOH—$CHCl_3$) and the filtrate was concentrated in vacuo. The crude material was purified by preparative HPLC (2 injections, each in 2 mL DMSO; Phenomenex Luna C18 21.2×100 mm; linear gradient 18-90% MeCN—$H_2O$ with 0.1% v/v TFA over 12 min; 20 mL/min; 220 nm detection). The product-containing fractions were filtered under gravity through an SPE cartridge packed with $PL-HCO_3$ MP resin (Agilent, 500 mg, 1.8 mmol/g loading) (washed with 3 mL of 1:1 MeCN—$H_2O$), and the eluent was lyophilized to provide compound 72 (4.9 mg, 12%) as a white solid. LC-MS m/z 1011 $[M+H]^+$.

To a RT solution of compound 72 (4.9 mg, 4.85 μmol) in DMSO (129 μL) was added a solution of compound 71a (6.69 mg, 9.70 μmol) in DMSO (64.7 μL), followed by 2,6-lutidine (1.130 μL, 9.70 μmol). The clear colorless solution was stirred at RT for 4 h. The reaction was purified by preparative HPLC (1 injection; Phenomenex Luna C18 21.2×100 mm; linear gradient 18-90% MeCN—$H_2O$ with 0.1% v/v TFA over 12 min; 20 mL/min; 220 nm detection). The product-containing fraction was filtered under gravity through an SPE cartridge packed with $PL-HCO_3$ MP resin (Agilent, 200 mg, 1.8 mmol/g loading) (washed with 2 mL of 1:1 MeCN—$H_2O$), and the eluent was lyophilized to provide dimer-linker compound IIIa-1 (2.4 mg, 31%) as a white solid. LC-MS m/z 1585 $[M+H]^+$.

Example 12—Dimer-Linkers IIIa-2, IIIa-3, and IIIa-4

Figure 12:
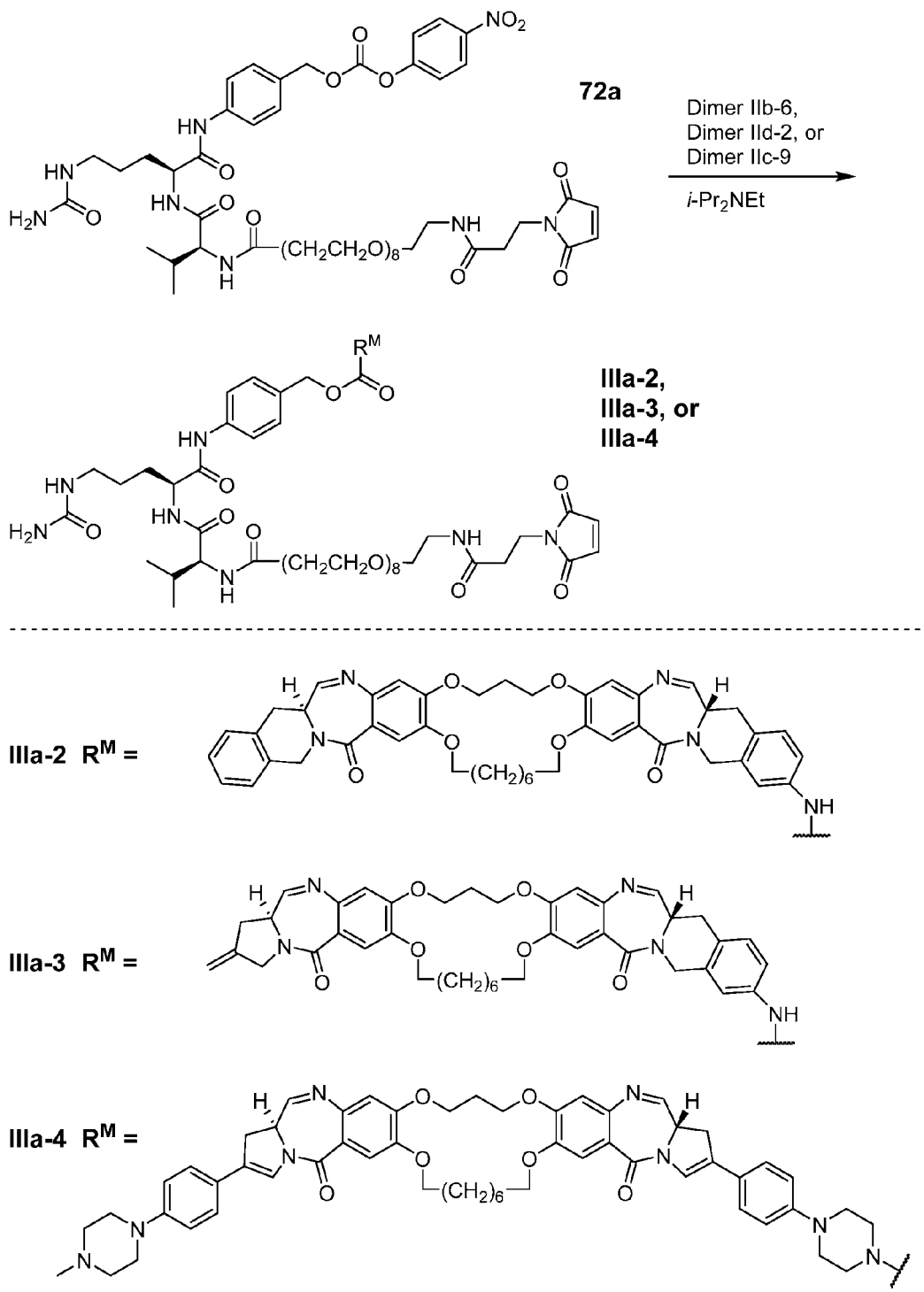

This example pertains to FIG. 12 and the synthesis of dimer-linkers IIIa-2, IIIa-3, and IIIa-4.

To a RT solution of dimer IIb-6 (7 mg, 9.29 μmol) in DMF (93 μL) was added a solution of compound 72a (12.47 mg, 0.011 mmol) in DMF (93 μL), followed by DIEA (4.85 μL, 0.028 mmol). The clear orange solution was stirred at RT for 15 mi; then 1-hydroxy-7-azabenzotriazole (1.517 mg, 0.011 mmol) was added. The reaction mixture was stirred at RT for 29 h, then diluted with DMSO and purified by preparative HPLC (1 injection; Phenomenex Luna C18 21.2×100 mm; linear gradient 18-90% MeCN—$H_2O$ with 0.1% v/v TFA over 15 min; 20 mL/min; 220 nm detection). The product-containing fraction was filtered under gravity through an SPE cartridge packed with $PL-HCO_3$ MP resin (Agilent, 200 mg, 1.8 mmol/g loading) (washed with 2 mL of 1:1 MeCN—H2O), and the eluent was lyophilized to provide dimer-linker IIIa-2 (4.43 mg, 28%) as a white solid. LC-MS m/z 1734 [M+H]+.

Dimer-linkers IIIa-3 and IIIa-4 were analogously prepared. Dimer-linker IIIa-3: LC-MS m/z 1684 $[M+H]^+$. Dimer-linker IIIa-4: LC-MS m/z 1925 $[M+H]^+$.

Example 13—Dimer-Linker IIIa-11

Figure 13A:
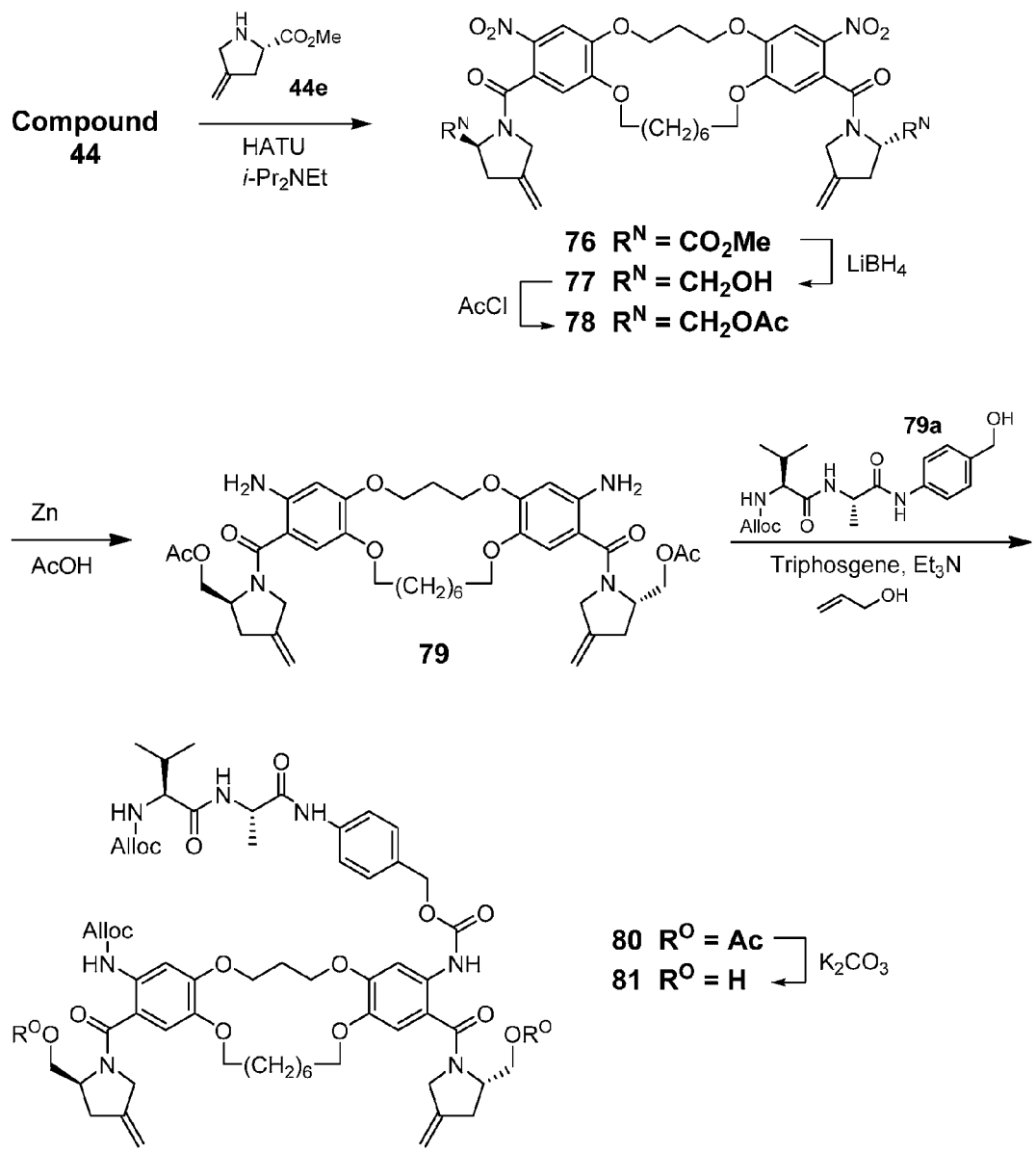
Figure 13B:
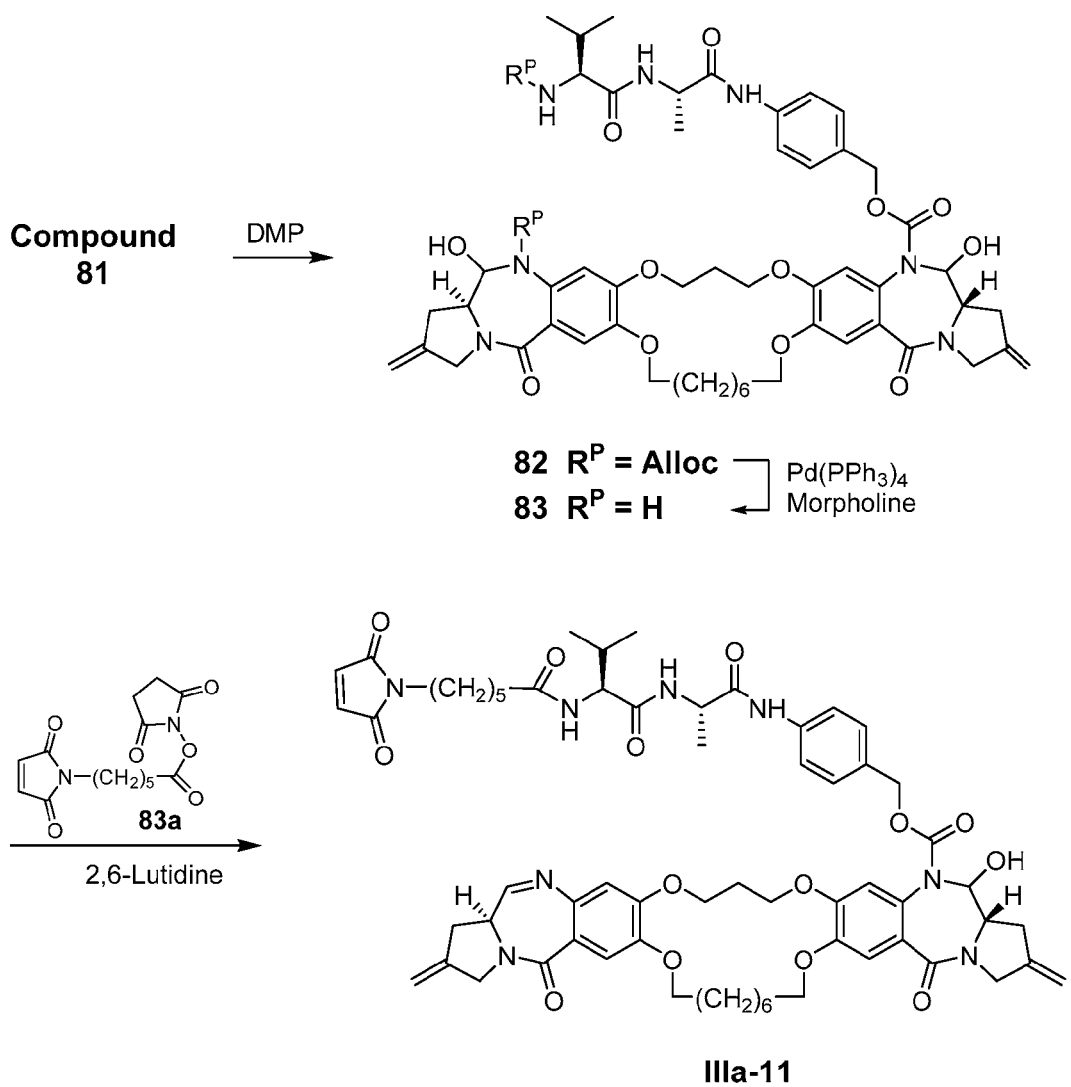

This example pertains to FIGS. 13A-13B and the synthesis of dimer-linker IIIa-11.

To a 0° C. solution of compound 44e (2.065 g, 8.09 mmol) in DMF (25.7 mL) was added compound 44 (2.114 g, 3.85 mmol), followed by DIEA (5.37 mL, 30.8 mmol) and HATU (3.22 g, 8.48 mmol), portionwise. The reaction was stirred at 0° C. for 5 min and RT for 1 h. Then it was slowly added to a stirred flask of $H_2O$ (200 mL) in a 0° C. bath. The resulting precipitate was collected by vacuum filtration ($H_2O$ wash), dissolved in EtOAc (200 mL), washed with sat. aq. NaCl (200 mL), dried over $Na_2SO_4$, filtered, and concentrated in vacuo. The crude material was purified by flash chromatography (40 g RediSep Gold silica gel with 25 g prepacked load cartridge; linear gradient 0-100% EtOAc—$CH_2Cl_2$) to provide compound 76 (3.1 g, quantitative) as an orange film. LC-MS m/z 795 $[M+H]^+$.

To a 0° C. solution of compound 76 (3.1 g, 3.90 mmol) in THF (39.0 mL) was added $LiBH_4$ (5.85 mL, 2.0 M solution in THF, 11.70 mmol), dropwise. The reaction was stirred at 0° C. for 30 min, then was allowed to warm to RT and stirred for an additional 3 h. The reaction was cooled to 0° C. and quenched by the addition of 1 M aq. HCl (100 mL), diluted with $H_2O$ (400 mL), and extracted with 10% MeOH-EtOAc (400 mL) and EtOAc (400 mL). The combined organic layers were washed with sat. aq. NaCl (200 mL), dried over $Na_2SO_4$, filtered, and concentrated in vacuo. The crude product 77 was used without further purification. LC-MS MS m/z 739 $[M+H]^+$.

To a 0° C. solution of the crude product 77 in DCM (77 mL) was added $NEt_3$ (1.607 mL, 11.53 mmol), followed by acetyl chloride (0.713 mL, 9.99 mmol). The reaction was allowed to warm to RT as it was stirred for 20 h, diluted with DCM (400 mL), washed with $H_2O$ (400 mL), dried over $Na_2SO_4$, filtered, and concentrated in vacuo. The crude material was purified by flash chromatography (80 g silica gel with 25 g prepacked load cartridge; linear gradient 0-100% EtOAc-hexanes) to provide compound 78 (1.59 g, 50%) as a white foam. LC-MS m/z 823 $[M+H]^+$.

To a RT solution of compound 78 (1.59 g, 1.932 mmol) in EtOH (61.8 mL) was added AcOH (15.46 mL), followed by zinc dust (3.79 g, 58.0 mmol). The reaction was stirred at reflux for 1 h, then it was cooled to RT and filtered through CELITE™ (washed with 400 mL DCM). The filtrate was washed with $H_2O$ (400 mL), sat. aq. $NaHCO_3$ (400 mL), and $H_2O$ (400 mL), dried over $Na_2SO_4$, filtered, and concentrated in vacuo. The crude material was purified by flash chromatography (40 g silica gel with 2.5 g prepacked load cartridge; linear gradient 0-10% MeOH—$CH_2Cl_2$). The mixed fractions were repurified by flash chromatography (12 g silica gel with 2.5 g prepacked load cartridge; linear gradient 0-10% MeOH-DCM) and the products from both columns were combined to provide compound 79 (1.162 g, 79%) as a white foam. LC-MS m/z 763 $[M+H]^+$; $^1$H NMR (400 MHz, $CDCl_3$) δ 6.80 (s, 2H), 6.27 (s, 2H), 5.04-5.00 (m, 2H), 4.99-4.95 (m, 2H), 4.86-4.75 (m, 2H), 4.37 (br s, 4H), 4.24-4.08 (m, 12H), 3.94 (t, J=5.5 Hz, 4H), 2.83-2.72

(m, 2H), 2.50-2.42 (m, 2H), 2.31 (quin, J=6.4 Hz, 2H), 2.04 (s, 6H), 1.76-1.65 (m, 4H), 1.61-1.52 (m, 4H), 1.44-1.37 (m, 4H).

To a 0° C. solution of triphosgene (117 mg, 0.396 mmol) and NEt$_3$ (487 µL, 3.49 mmol) in THF (3695 µL) was added a solution of compound 79 (444 mg, 0.582 mmol) in THF (3695 µL), dropwise. The cloudy mixture was stirred at 0° C. for 10 min, then a suspension of compound 79a (231 mg, 0.611 mmol) in THF (5543 µL) was added dropwise, followed by allyl alcohol (41.7 µL, 0.611 mmol). The suspension was stirred at 0° C. for 1 h, then it was allowed to warm to RT as it was stirred for 5 h. The reaction was diluted with H$_2$O (125 mL) and extracted with CH$_2$Cl$_2$ (2×125 mL). The combined organic layers were dried over Na$_2$SO$_4$, filtered, and concentrated in vacuo. The crude material was purified by flash chromatography (80 g RediSep Gold silica gel with 5 g prepacked load cartridge; linear gradient 0-10% MeOH-DCM) to provide compound 80 (214 mg, 29%) as an off-white solid. LC-MS m/z 1250 [M+H]$^+$; $^1$H NMR (400 MHz, DMSO-d$_6$) δ 9.98 (s, 1H), 9.13-9.02 (m, 2H), 8.14 (d, J=6.8 Hz, 1H), 7.58 (d, J=8.6 Hz, 2H), 7.31 (d, J=8.7 Hz, 2H), 7.23 (d, J=8.7 Hz, 1H), 7.20-7.12 (m, 2H), 6.99-6.89 (m, 2H), 5.98-5.85 (m, 2H), 5.36-5.26 (m, 2H), 5.22-5.13 (m, 2H), 5.06-4.93 (m, 6H), 4.62-4.50 (m, 4H), 4.50-4.46 (m, 2H), 4.45-4.38 (m, 1H), 4.22-3.80 (m, 17H), 2.78-2.67 (m, 2H), 2.44-2.35 (m, 2H), 2.21-2.13 (m, 2H), 2.04-1.90 (m, 7H), 1.69-1.62 (m, 4H), 1.54-1.46 (m, 4H), 1.40-1.35 (m, 4H), 1.30 (d, J=7.0 Hz, 3H), 0.88 (d, J=6.8 Hz, 3H), 0.83 (d, J=6.6 Hz, 3H).

To a RT solution of compound 80 (213 mg, 0.170 mmol) in MeOH (3097 µL) was added H$_2$O (310 µL) and K$_2$CO$_3$ (118 mg, 0.852 mmol). The reaction was stirred at RT for 1 h, diluted with H$_2$O (100 mL), and extracted with EtOAc (2×100 mL). The combined organic layers were washed with sat. aq. NaCl (100 mL), dried over Na$_2$SO$_4$, filtered, and concentrated in vacuo. The crude material was purified by flash chromatography (40 g silica gel with 5 g prepacked load cartridge; linear gradient 0-10% MeOH—CH$_2$Cl$_2$) to provide compound 81 (159 mg, 80%) as a white solid. LC-MS m/z 1166 [M+H]$^+$; $^1$H NMR (400 MHz, DMSO-d$_6$) δ 9.99 (s, 1H), 9.17-8.86 (m, 2H), 8.15 (d, J=7.0 Hz, 1H), 7.58 (d, J=8.6 Hz, 2H), 7.32 (d, J=8.7 Hz, 2H), 7.27-7.16 (m, 3H), 7.03-6.96 (m, 2H), 5.98-5.85 (m, 2H), 5.35-5.26 (m, 2H), 5.23-5.14 (m, 2H), 5.07-4.76 (m, 8H), 4.56-4.52 (m, 2H), 4.50-4.46 (m, 2H), 4.45-4.39 (m, 1H), 4.37-4.30 (m, 1H), 4.18-4.11 (m, 4H), 4.08-3.80 (m, 10H), 3.57-3.46 (m, 1H), 3.39-3.26 (m, 2H), 3.22-3.03 (m, 1H), 2.65-2.46 (m, 4H), 2.21-2.12 (m, 2H), 2.03-1.93 (m, 1H), 1.70-1.61 (m, 4H), 1.55-1.46 (m, 4H), 1.42-1.34 (m, 4H), 1.30 (d, J=7.0 Hz, 3H), 0.88 (d, J=6.8 Hz, 3H), 0.84 (d, J=6.7 Hz, 3H).

To a RT solution of compound 81 (157 mg, 0.135 mmol) in CH$_2$Cl$_2$ (3365 µL) was added Dess-Martin periodinane (DMP, 120 mg, 0.283 mmol). The reaction was stirred at RT for 4 h, diluted with sat. aq. NaHCO$_3$ (50 mL), and extracted with CH$_2$Cl$_2$ (2×50 mL). The combined organic layers were dried over Na$_2$SO$_4$, filtered, and concentrated in vacuo. The crude material was purified by flash chromatography (40 g silica gel with 5 g prepacked load cartridge; linear gradient 0-10% MeOH—CH$_2$Cl$_2$). The mixed fractions were repurified by flash chromatography (40 g RediSep silica gel with 5 g prepacked load cartridge; linear gradient 0-10% MeOH—CH$_2$Cl$_2$) and the products from both columns were combined to provide compound 82 (115 mg, 74%) as a white solid. LC-MS m/z 1162 [M+H]$^+$.

To a RT suspension of compound 82 (96.5 mg, 0.083 mmol) in DCM (1661 µL) was added morpholine (36.5 µL, 0.415 mmol) and tetrakis(triphenylphosphine)palladium(O) (4.80 mg, 4.15 µmol). The reaction was stirred at RT for 2 h, was concentrated under a stream of N$_2$, and purified by flash chromatography (12 g silica gel; linear gradient 0-10% MeOH-DCM). The mixed fractions were repurified by flash chromatography (12 g silica gel; linear gradient 0-10% MeOH—CH$_2$Cl$_2$) and the products from both columns were combined to provide compound 83 (54.9 mg, 68%). LC-MS m/z 976 [M+H]$^+$.

To a RT solution of compound 83 (42.3 mg, 0.043 mmol) in DMF (867 µL) was added 2,6-lutidine (15.14 µL, 0.130 mmol), followed by compound 83a (20.04 mg, 0.065 mmol). The reaction was stirred at RT for 2 days, diluted with DMSO, and purified by preparative HPLC (5 1-mL injections; Phenomenex Luna C18 21.2×100 mm; linear gradient 20-80% MeCN—H$_2$O with 0.05% v/v HCO$_2$H over 25 min; 20 mL/min; 220 nm detection). The product-containing fractions were lyophilized and purified by flash chromatography (12 g RediSep Gold silica gel; linear gradient 0-20% MeOH-DCM) to provide dimer-linker IIIa-11 (3.67 mg, 7%) as an off-white solid. LC-MS m/z 1170 [M+H]$^+$.

Example 14—Dimer-Linker 111a-5

Figure 14:
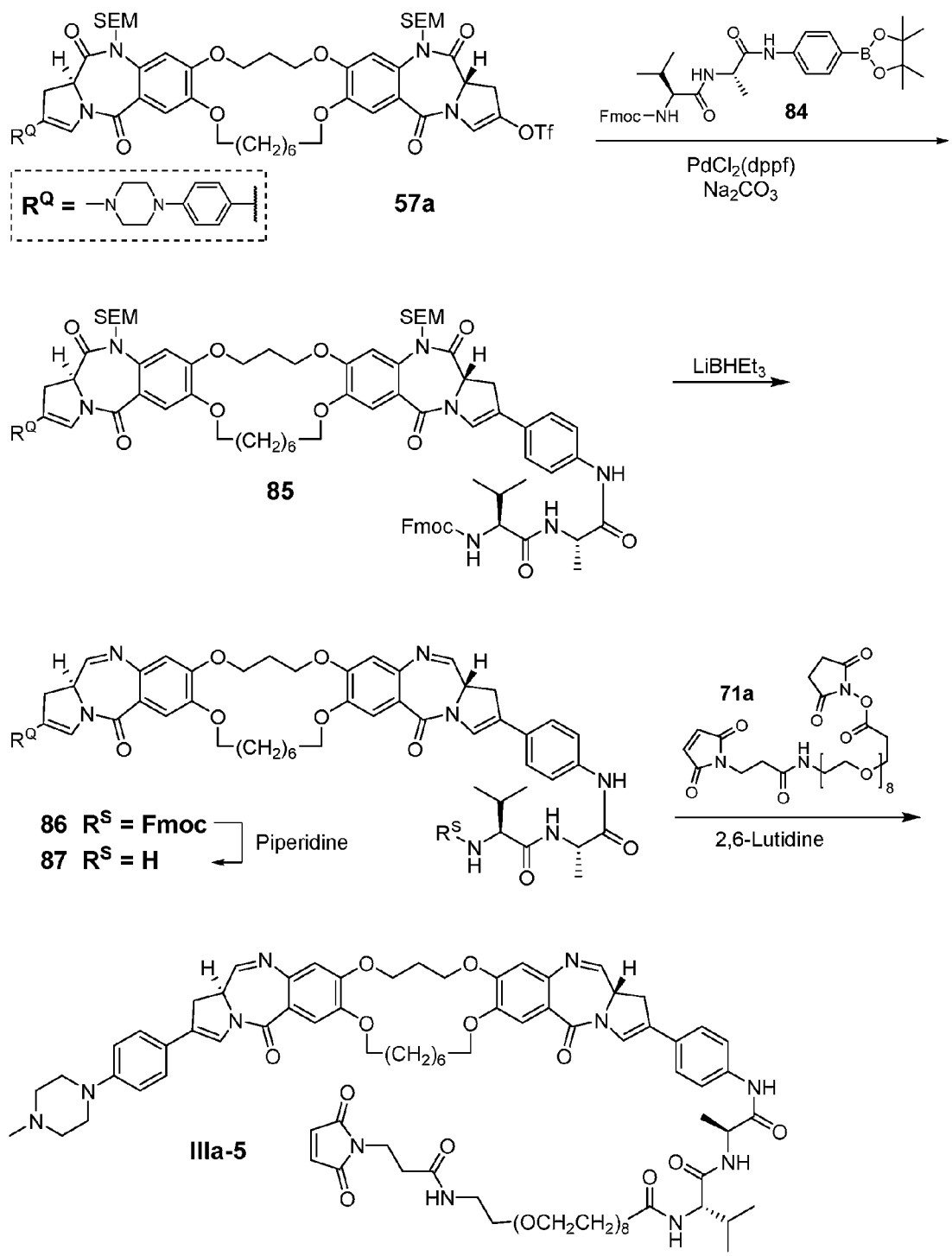

This example pertains to FIG. 14 and the synthesis of dimer-linker IIIa-5.

A mixture of compound 57a (82.5 mg, 0.067 mmol), compound 84 (45.3 mg, 0.074 mmol), PdCl$_2$(dppf) (2.463 mg, 3.37 µmol), and Na$_2$CO$_3$ (35.7 mg, 0.337 mmol) was evacuated and backfilled with N$_2$. THF (898 µL) and H$_2$O (449 µL) were added. The mixture was sparged with N$_2$ for 5 min and stirred at RT for 30 min. The reaction mixture was diluted H$_2$O (50 mL) and extracted with DCM (2×50 mL). The combined organic layers were dried over Na$_2$SO$_4$, filtered, and concentrated in vacuo. The crude material was purified by flash chromatography (24 g silica gel with 5 g prepacked load cartridge; linear gradient 0-20% MeOH-DCM) to provide compound 85 (98.9 mg, 94%) as an orange film. LC-MS m/z 1561 [M+H]$^+$.

To a −78° C. solution of compound 85 (98.9 mg, 0.063 mmol) in THF (2112 µL) was added LiBHEt$_3$ (317 µL, 1 M solution in THF, 0.317 mmol), dropwise. The reaction mixture was stirred at −78° C. for 1 h, diluted with H$_2$O (50 mL) and extracted with CHCl$_3$ (50 mL) and 10% MeOH—CHCl$_3$ (50 mL). The combined organic layers were dried over Na$_2$SO$_4$, filtered, and concentrated in vacuo. The residue was taken up in a mixture of THF (4217 µL), MeCN w/0.05% v/v HCO$_2$H (2109 µL), and H$_2$O w/0.05% v/v HCO$_2$H (2109 µL), and stirred at RT for 1 h. The reaction was quenched by the addition of sat. aq. NaHCO$_3$ (50 mL) and extracted with CHCl$_3$ (2×50 mL). The combined organic layers were dried over Na$_2$SO$_4$, filtered, and concentrated in vacuo. The crude material was purified by flash chromatography (24 g basic alumina; linear gradient 0-20% MeOH—CHCl$_3$) to provide compound 86 (54.6 mg, 68%) as an orange solid. LC-MS m/z 1286 [M+18]$^+$.

To a RT solution of compound 86 (29.0 mg, 0.023 mmol) in THF (457 µL) was added piperidine (45.3 µL, 0.457 mmol). The clear orange solution was stirred at RT for 45 min and then concentrated in vacuo. The crude material was taken up in a mixture of MeCN (2 mL) and MeOH (2 mL) and washed with heptane (4×2 mL). The MeCN-MeOH layer was concentrated in vacuo. The residue was taken up in CHCl$_3$ and concentrated (2×), to give compound 87, which was used without further purification. LC-MS m/z 1065 [M+H]$^+$.

To a RT solution of crude 87 and compound 71a (23.65 mg, 0.034 mmol) in DMSO (457 μL) was added 2,6-lutidine (6.66 μL, 0.057 mmol). The clear yellow solution was stirred at RT for 1.5 h, diluted with DMSO, and purified by preparative HPLC (3 1-mL injections; Phenomenex Luna C18 21.2×100 mm; linear gradient 20-60% MeCN—$H_2O$ w/0.05% v/v $HCO_2H$ over 25 min; 20 mL/min; 220 nm detection). The product-containing fractions were lyophilized to provide dimer-linker IIIa-5 (6.97 mg, 19%) as a light yellow solid. LC-MS m/z 1621 [M+H]$^+$.

Example 15—Dimer-Linker IIIa-6

Figure 15:
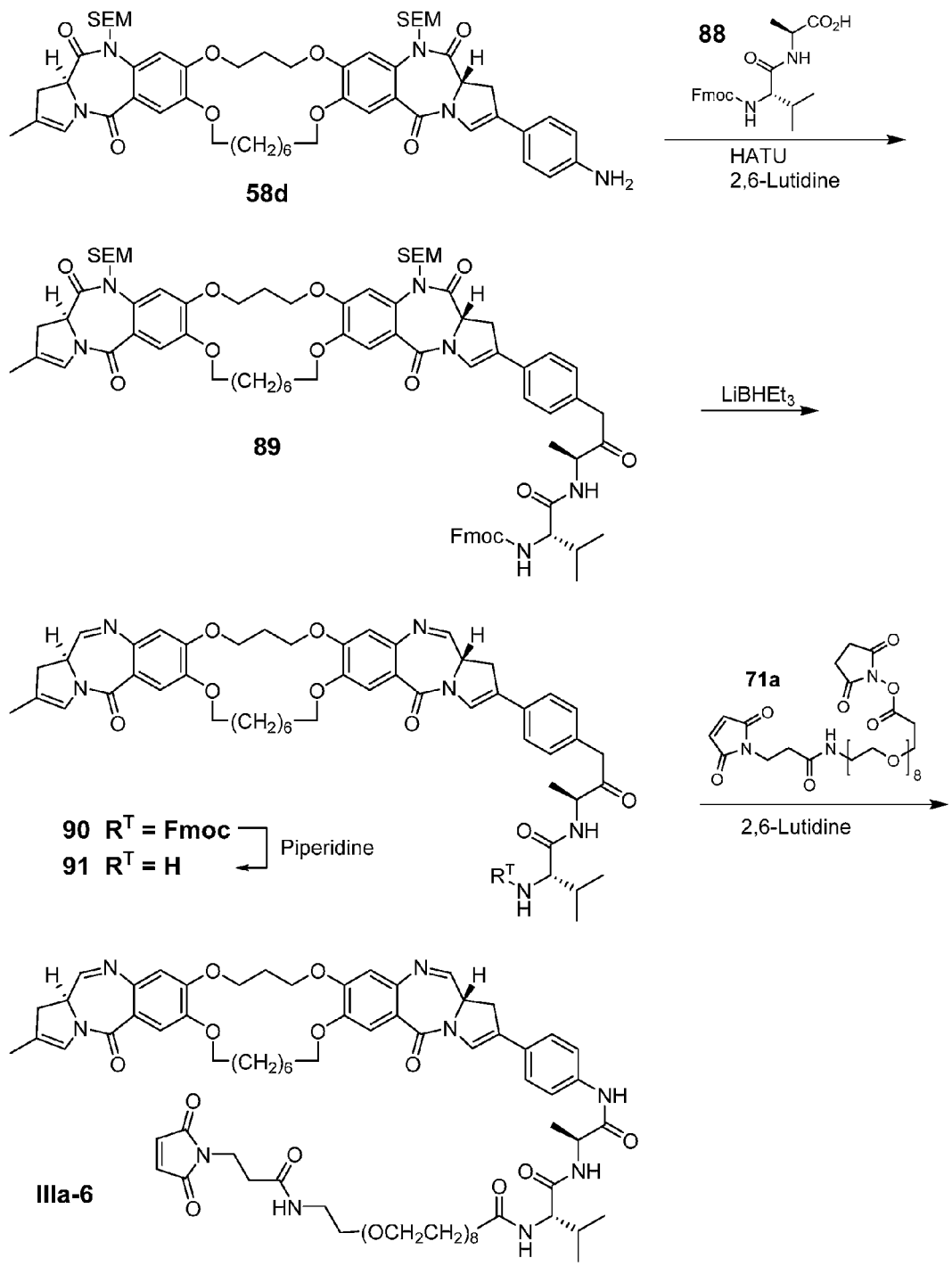

This example pertains to FIG. 15 and the synthesis of dimer-linker IIIa-6.

To a 0° C. solution of compound 58d (50.0 mg, 0.050 mmol) and compound 88 (24.42 mg, 0.060 mmol) in DMF (496 μL) was added HATU (22.62 mg, 0.060 mmol), followed by 2,6-lutidine (14.44 μL, 0.124 mmol). The reaction mixture was stirred at 0° C. for 10 min and RT for 2 h and added dropwise to a stirred flask of $H_2O$ (20 mL) in a 0° C. bath. The resulting precipitate was collected by vacuum filtration (washed with $H_2O$), then taken up in DCM (50 mL) and sat. aq. $NaHCO_3$ (50 mL). The layers were separated and the aqueous layer was extracted with DCM (50 mL). The combined organic layers were dried over $Na_2SO_4$, filtered, and concentrated in vacuo. The crude product was purified by flash chromatography (12 g silica gel; linear gradient 0-10% MeOH-DCM) to provide compound 89 (61.5 mg, 89%) as a yellow solid. LC-MS m/z 1401 [M+H]$^+$.

To a −78° C. solution of compound 89 (61.5 mg, 0.044 mmol) in THF (1463 μL) was added LiBHEt$_3$ (220 μL, 1 M solution in THF, 0.220 mmol), dropwise. The reaction mixture was stirred at −78° C. for 1 h, quenched by the addition of $H_2O$, warmed to RT, diluted with a mixture of sat. aq. $NaHCO_3$ (25 mL) and $H_2O$ (25 mL), and extracted with 10% MeOH—$CHCl_3$ (2×50 mL). The combined organic layers were dried over $Na_2SO_4$, filtered, and concentrated in vacuo. This residue was taken up in a mixture of THF (5867 μL), EtOH (5867 μL), and $H_2O$ w/0.05% v/v $HCO_2H$ (2933 μL) and stirred at RT for 2 h. The reaction was diluted with sat. aq. $NaHCO_3$ (50 mL) and extracted with $CHCl_3$ (50 mL), followed by 10% MeOH—$CHCl_3$ (50 mL). The combined organic layers were dried over $Na_2SO_4$, filtered, and concentrated in vacuo. The crude product was purified by flash chromatography (12 g silica gel; linear gradient 0-20% MeOH-DCM) to provide compound 90 (49 mg, quant.) as a yellow solid. LC-MS m/z 1109 [M+H]$^+$.

To a RT solution of compound 90 (49 mg, 0.044 mmol) in THF (884 μL) was added piperidine (88 μL, 0.884 mmol). The clear orange solution was stirred at RT for 1 h and concentrated in vacuo. The crude product was taken up in a mixture of MeCN (2 mL) and MeOH (2 mL) and washed with heptane (4×2 mL). The MeCN-MeOH layer was concentrated in vacuo. This product 91 was taken up in $CHCl_3$ and concentrated (2×) and then used without further purification. LC-MS m/z 887 [M+H]$^+$.

To a RT solution of crude product 91 and compound 71a (22.76 mg, 0.033 mmol) in DMSO (440 μL) was added 2,6-lutidine (6.41 μL, 0.055 mmol). The clear, yellow solution was stirred at RT for 30 min. An additional solution of compound 71a (3.2 μL, 0.027 mmol) in DMSO (0.220 mL) was added, and the reaction mixture was stirred for an additional 1.5 h, diluted with DMSO and purified by preparative HPLC (3 1-mL injections; Phenomenex Luna C18 21.2×100 mm; linear gradient 20-60% MeCN—$H_2O$ w/0.05% v/v $HCO_2H$ over 25 min; 20 mL/min; 220 nm detection). The product-containing fractions were lyophilized to provide dimer-linker IIIa-6 (6.51 mg, 20%) as a yellow solid. LC-MS m/z 1461 [M+H]$^+$.

Example 16—Dimer IIb-8

Figure 16A:
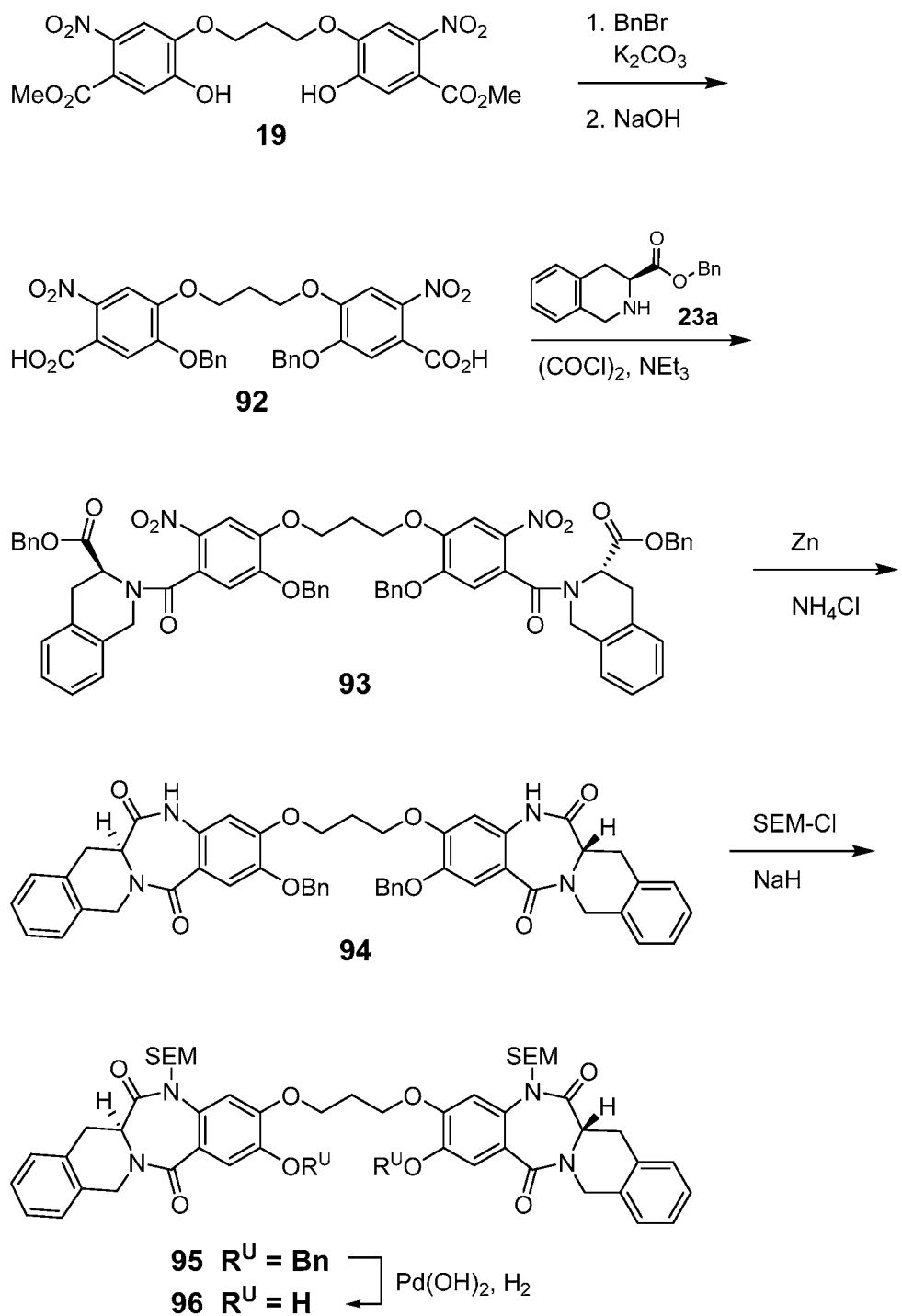
FIGS. 16A-16B show, in combination, the synthesis of another dimer of this invention.
Figure 16B:
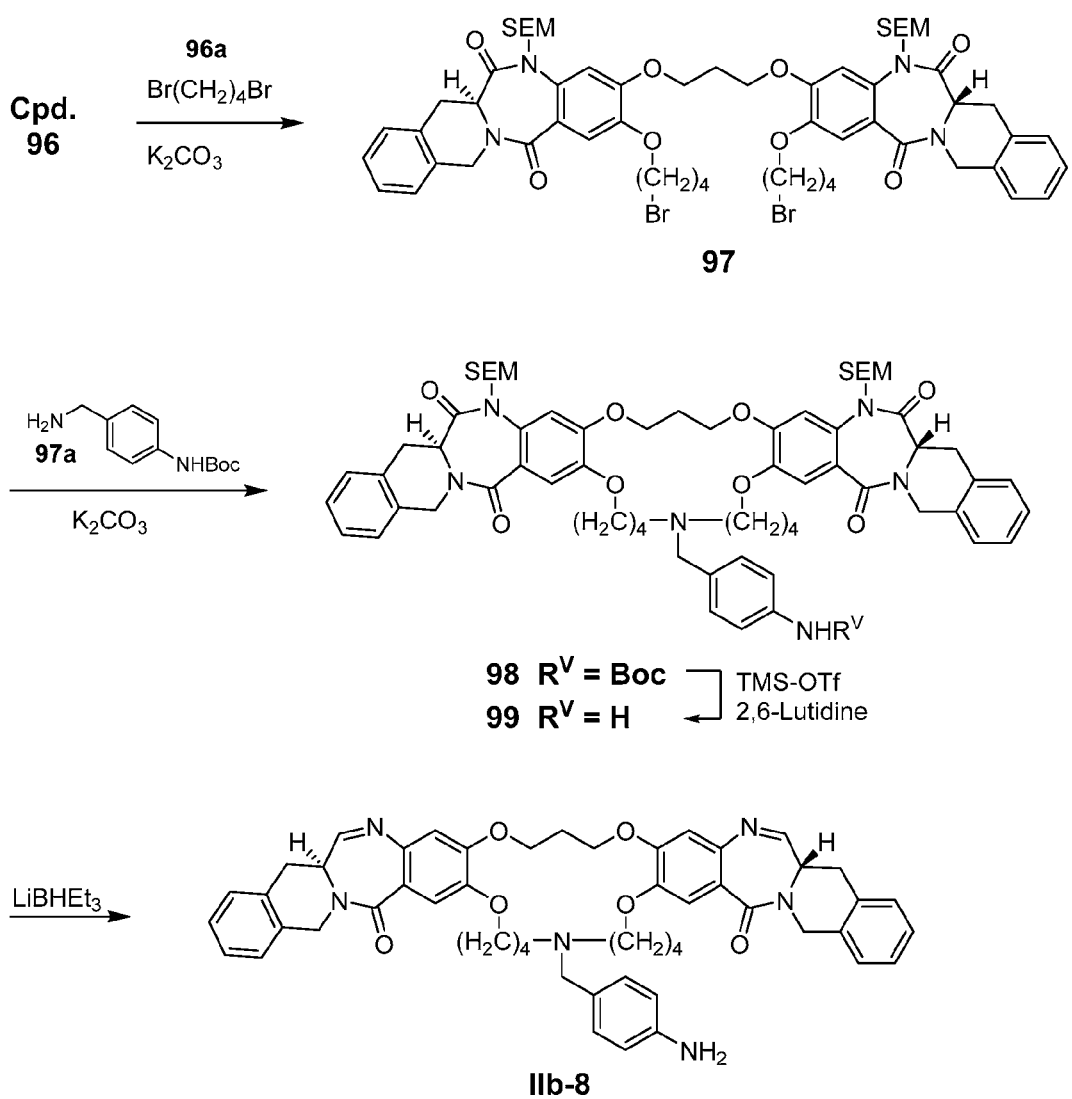

This example pertains to FIGS. 16A and 16B and the synthesis of dimer IIb-8.

To a solution of compound 19 (10 g, 21.44 mmol) in acetone (80 mL) was added benzyl bromide (5.23 ml, 44.0 mmol, Aldrich) followed by $K_2CO_3$ (11.85 g, 86 mmol, Aldrich). The resulting bright yellow reaction mixture was stirred at 80° C. overnight. The yellow reaction mixture was poured into 200 mL of cold water. The solid precipitate was collected by filtration, washed with water and ether, and dried under vacuum to give a light yellow solid (12.8 g, 92%).

To a suspension of the precipitate from the previous step (12.8 g, 19.80 mmol) in THF (75 ml) and MeOH (25 mL) was added NaOH (39.6 ml, 119 mmol, 3.0 N). The reaction mixture was stirred at RT overnight to give a light brown homogeneous solution The reaction mixture was concentrated in vacuo to remove most of the organic solvents. The residue was neutralized with 1.0 N HCl to pH 2-3. The solid formed was collected by filtration, washed with water and ether to give an off-white solid. The solid was dried under vacuum overnight to give compound 92 as a white solid (10.21 g, 83%). $^1$H NMR (400 MHz, CD3OD) δ 7.47 (s, 2H), 7.42-7.36 (m, 10H), 7.16 (s, 2H), 5.18 (s, 4H), 4.31 (t, J=5.9 Hz, 4H), 2.41 (t, J=5.9 Hz, 2H). MS (ESI$^+$) m/z 619.5 (M+H)$^+$.

Compound 92 was converted to compound 95, proceeding via compounds 93 and 94, following the procedures described in Example 14 and FIG. 4A.

To a pressure flask containing Pd(OH)$_2$ on carbon (0.060 g, 0.085 mmol, Aldrich) was added a solution of compound 95 (0.94 g, 0.853 mmol) in MeOH (10 mL) and EtOAc (10 mL). The resulting reaction mixture was stirred under $H_2$ at 20 psi pressure for 2 h and at 40 psi pressure for another 2 h. The reaction mixture was filtered through a pad of CELITE™, washing with EtOAc. The filtrate was concentrated in vacuo to give 650 mg of compound 96 as a faint orange solid (650 mg, 83%). MS (ESI$^+$) m/z 921.6 (M+H)$^+$.

To a solution of compound 96 (101 mg, 0.110 mmol) and 1,4-dibromobutane 96a (189 mg, 0.877 mmol, Aldrich) in DMF (1 mL) was added $K_2CO_3$ (45.5 mg, 0.329 mmol). The reaction mixture was stirred at RT overnight. The reaction was diluted with water. The solid formed was collected by filtration, and purified by flash chromatography to give compound 97, as a semi solid (110 mg, 84%). MS (ESI$^+$) m/z 1191.6 (M+H)$^+$.

To a solution of compound 97 (470 mg, 0.395 mmol) and tert-butyl (4-(aminomethyl)phenyl)carbamate 97a (88 mg, 0.395 mmol, Aldrich) in DMF (4 mL) was added $K_2CO_3$ (164 mg, 1.184 mmol). The reaction was heated at 85° C. for 3 h. The reaction was diluted with water and extracted with DCM (3×). The combined organic extracts were dried and concentrated, and purified by flash chromatography to give compound 98, as a semi solid (175 mg, 35%). MS (ESI$^+$) m/z 1251.5 (M+H)$^+$.

To a solution of compound 98 (78.5 mg, 0.063 mmol) and 2,6-lutidine (0.022 mL, 0.188 mmol, Aldrich) in DCM (1.0 mL) at RT was added trimethylsilyl trifluoromethane sulfonate (TMS-OTf, 0.034 mL, 0.188 mmol, Aidrich). The reaction mixture was stirred at RT for 1 h. The reaction mixture was diluted with DCM and washed with aq. sat.

NaHCO$_3$. The organic phase was dried, concentrated, and purified by flash chromatography to give compound 99, as a semi solid (23 mg, 32%). MS (ESI$^+$) m/z 1152.6 (M+H)$^+$.

To a −78° C. solution of compound 99 (46 mg, 0.040 mmol) in THF (1 mL) was added a solution of SUPER-HYDRIDE® (0.399 mL, 0.399 mmol, 1M in THF, Aldrich). The reaction was stirred at −78° C. for 1 h. The reaction was quenched with water and extracted with chloroform (2×), then 10% MeOH in chloroform (2×). The combined organic extracts were dried, concentrated and purified by preparative HPLC. Fractions containing the product were neutralized with NaHCO$_3$, and extracted with chloroform (2×) and 10% MeOH in chloroform (2×). The combined organic extracts were dried over MgSO$_4$, filtered, and concentrated in vacuo. The product was then placed under high vacuum over a weekend to give dimer IIb-8 a white solid (12 mg, 32%). $^1$H NMR (400 MHz, CDCl$_3$) δ 7.61-7.55 (m, 4H), 7.49 (d, J=7.9 Hz, 2H), 7.42-7.31 (m, 6H), 7.09 (d, J=7.9 Hz, 2H), 6.86-6.82 (m 2H), 6.55 (s, 2H), 5.03 (d, J=15.5 Hz, 2H), 4.57 (d, J=15.5 Hz, 2H), 4.37-4.29 (m, 8H), 4.01-3.88 (m, 4H), 3.37-3.07 (m, 4H), 2.52 (t, J=5.9 Hz, 2H), 1.93-1.85 (m 6H), 1.71-1.60 (m, 8H). MS (ESI$^+$) m/z 859.2 (M+H)$^+$.

Example 17—Additional Dimers and Dimer-Linkers

Following the synthetic principles described hereinabove, the following additional dimers and dimer linkers were prepared:

Dimer IIa-2: LCMS (M+H)=615.2 $^1$H NMR (400 MHz, CHLOROFORM-d) δ 7.68 (d, J=4.4 Hz, 2H), 7.54 (s, 2H), 6.88 (s, 2H), 4.39-4.25 (m, 4H), 4.23-4.15 (m, 2H), 4.14-4.06 (m, 2H), 3.83 (ddd, J=11.7, 7.2, 4.3 Hz, 2H), 3.76 (dt, J=7.6, 4.0 Hz, 2H), 3.65-3.55 (m, 2H), 2.40-2.29 (m, 6H), 2.13-2.01 (m, 4H), 1.84-1.7 (m, 4H), 1.64-1.52 (m., 4H), 1.48-1.42 (m, 4H).

Dimer IIa-5: LCMS (M+H)=657.4 $^1$H NMR (400 MHz, CHLOROFORM-d) δ 7.69 (d, J=4.4 Hz, 2H), 7.55 (s, 2H), 6.84 (s, 2H), 4.36-4.17 (m, 6H), 4.15-4.08 (m, 2H), 3.84 (ddd, J=11.7, 7.2, 4.3 Hz, 2H), 3.78-3.72 (m, 2H), 3.67-3.56 (m, 2H), 2.46-2.30 (m, 6H), 2.16-2.03 (m, 4H), 1.88-1.78 (m, 4H), 1.65-1.50 (m, 6H), 1.48-1.34 (m, 8H).

Dimer IIa-6: LCMS (M+H)=671.4 $^1$H NMR (400 MHz, CHLOROFORM-d) δ 7.68 (d, J=4.4 Hz, 2H), 7.53 (s, 2H), 6.84 (s, 2H), 4.34-4.15 (m, 6H), 4.12-4.05 (m, 2H), 3.84 (ddd, J=11.7, 7.2, 4.3 Hz, 2H), 3.78-3.73 (m, 2H), 3.66-3.56 (m, 2H), 2.52-2.30 (m, 6H), 2.17-2.02 (m, 4H), 1.92-1.77 (m, 4H), 1.65-1.50 (m, 6H), 1.43-1.27 (m, 10H).

Dimer IIa-7: LCMS (M+H)=685.3 $^1$H NMR (400 MHz, CHLOROFORM-d) δ 7.68 (d, J=4.4 Hz, 2H), 7.54 (s, 2H), 6.83 (s, 2H), 4.22-4.03 (m, 10H), 3.84 (ddd, J=11.7, 7.1, 4.5 Hz, 3H), 3.76 (dt, J=7.5, 4.0 Hz, 2H), 3.61 (dt, J=11.8, 7.8 Hz, 2H), 2.34 (td, J=6.7, 2.6 Hz, 4H), 2.08 (d, J=5.1 Hz, 4H), 1.99-1.92 (m, 5H), 1.88-1.76 (m, 8H), 1.59-1.50 (m, 14H), 1.47-1.38 (m, 7H).

Dimer IIa-8. LCMS (M+H)=699.5 $^1$H NMR (400 MHz, CHLOROFORM-d) δ 7.68 (d, J=4.4 Hz, 2H), 7.52 (s, 2H), 6.81 (s, 2H), 4.23-4.01 (m, 10H), 3.84 (ddd, J=11.7, 7.2, 4.3 Hz, 2H), 3.78-3.71 (m, 2H), 3.61 (dt, J=11.9, 7.6 Hz, 2H), 2.34 (td, J=6.7, 2.9 Hz, 4H), 2.09 (dd, J=6.9, 4.7 Hz, 4H), 2.00-1.92 (m, 5H), 1.88-1.72 (m, 8H), 1.58 (br. s, 13H), 1.39 (d, J=6.2 Hz, 12H).

Dimer IIa-10: LC-MS m/z 665 [M+H]$^+$; $^1$H NMR (400 MHz, CDCl$_3$) δ 7.68 (d, J=4.4 Hz, 2H), 7.50 (s, 2H), 6.84 (s, 2H), 5.47-5.43 (m, 2H), 5.23-5.14 (m, 4H), 4.34-4.20 (m, 8H), 4.18-4.11 (m, 2H), 4.10-4.02 (m, 2H), 3.93-3.86 (m, 2H), 3.18-3.08 (m, 2H), 2.99-2.90 (m, 2H), 2.40-2.29 (m, 2H), 2.09-2.01 (m, 4H), 1.87-1.76 (m, 4H), 1.64-1.56 (m, 4H).

Dimer IIa-11: LC-MS m/z 667 [M+H]$^+$.

Dimer IIa-12: LC-MS m/z 639 [M+H]$^+$; $^1$H NMR (400 MHz, CDCl$_3$) δ 7.68 (d, J=4.4 Hz, 2H), 7.51 (s, 2H), 6.86 (s, 2H), 5.22-5.15 (m, J=4.0 Hz, 4H), 4.36-4.23 (m, 8H), 4.21-4.14 (m, 2H), 4.12-4.05 (m, 2H), 3.93-3.87 (m, 2H), 3.17-3.07 (m, 2H), 2.99-2.90 (m, 2H), 2.34 (quin, J=6.2 Hz, 2H), 1.84-1.75 (m, 4H), 1.63-1.54 (m, 4H), 1.48-1.40 (m, 4H).

Dimer IIa-13: LC-MS m/z 643 [M+H]$^+$; $^1$H NMR (400 MHz, CDCl$_3$) δ 7.67 (d, J=4.4 Hz, 2H), 7.49 (s, 2H), 6.86 (s, 2H), 5.22-5.13 (m, 4H), 4.40-4.25 (m, 10H), 4.23-4.17 (m, 2H), 3.94-3.85 (m, 6H), 3.84-3.77 (m, 4H), 3.18-3.05 (m, 2H), 2.97-2.89 (m, 2H), 2.32 (quin, J=6.0 Hz, 2H).

Dimer IIa-14: LC-MS m/z 672.5 [M+H2O+H]$^+$.

Dimer IIb-1: LC-MS m/z 739 [M+H]$^+$; $^1$H NMR (400 MHz, CDCl$_3$) δ 7.55 (s, 2H), 7.49 (d, J=5.3 Hz, 2H), 7.41-7.30 (m, 8H), 6.87 (s, 2H), 5.02 (d, J=15.6 Hz, 2H), 4.57 (d, J=15.6 Hz, 2H), 4.38-4.24 (m, 4H), 4.24-4.16 (m, 2H), 4.10 (dt, J=9.7, 5.1 Hz, 2H), 4.01-3.94 (m, 2H), 3.34-3.24 (m, 2H), 3.22-3.11 (m, 2H), 2.35 (quin, J=6.1 Hz, 2H), 1.91-1.74 (m, 4H), 1.59 (d, J=5.9 Hz, 6H), 1.50-1.40 (m, 4H), 0.97-0.82 (m, 2H).

Dimer IIb-2: LC-MS m/z 767 [M+H]$^+$; $^1$H NMR (400 MHz, CDCl$_3$) δ 7.53 (s, 2H), 7.47 (d, J=5.3 Hz, 2H), 7.39-7.29 (m, 8H), 6.81 (s, 2H), 5.01 (d, J=15.6 Hz, 2H), 4.56 (d, J=15.6 Hz, 2H), 4.33-4.14 (m, 6H), 4.11-4.04 (m, 2H), 3.99-3.93 (m, 2H), 3.31-3.24 (m, 2H), 3.19-3.13 (m, 2H), 2.39 (quin, J=6.7 Hz, 2H), 1.83-1.75 (m, 4H), 1.62-1.52 (m, 4H), 1.41-1.32 (m, 8H).

Dimer IIb-3: LC-MS m/z 739 [M+H]$^+$; $^1$H NMR (400 MHz, CDCl$_3$) δ 8.27 (d, J=7.9 Hz, 2H), 7.88 (d, J=4.4 Hz, 2H), 7.56 (s, 2H), 7.32-7.20 (m, 4H), 7.14-7.08 (m, 2H), 6.86 (s, 2H), 4.50 (dt, J=10.9, 4.2 Hz, 2H), 4.38-4.05 (m, 8H), 3.78-3.67 (m, 2H), 3.55-3.46 (m, 2H), 2.47-2.36 (m, 2H), 1.83-1.76 (m, 4H), 1.59 (s, 4H), 1.42-1.31 (m, 8H).

Dimer IIb-4: LC-MS m/z 743.2 (M+H)$^+$; $^1$H NMR (400 MHz, CDCl$_3$-d) δ 7.53 (s, 2H), 7.47 (d, J=5.1 Hz, 2H), 7.40-7.29 (m, 8H), 6.86 (s, 2H), 5.01 (d, J=15.6 Hz, 2H), 4.54 (d, J=15.6 Hz, 2H), 4.37-4.27 (m, 6H), 4.24-4.18 (m, 2H), 3.97-3.88 (m, 6H), 3.82 (d, J=1.1 Hz, 4H), 3.31-3.23 (m, 2H), 3.19-3.11 (m, 2H), 2.37-2.29 (m, 2H).

Dimer IIb-7. LC-MS m/z 758.6 (M+H)$^+$; $^1$H NMR (400 MHz, DMSO-d$_6$) δ 7.48 (s, 2H), 7.43 (d, J=5.3 Hz, 2H), 7.38 (d, J=5.3 Hz, 2H), 7.36-7.26 (m, 4H), 7.04 (d, J=8.4 Hz, 1H), 6.87 (s, 2H), 6.52 (br. s., 2H), 4.91 (d, J=15.3 Hz, 2H), 4.53 (d, J=15.0 Hz, 2H), 4.30-4.20 (m, 6H), 4.20-4.16 (m, 2H), 3.91-3.88 (m, 6H), 3.65 (s, 4H), 3.46-3.45 (m, 2H), 3.10-3.06 (m., 2H), 2.25-2.17 (m, 2H).

Dimer IIc-1: LC-MS m/z 791 [M+H]$^+$; $^1$H NMR (400 MHz, CHLOROFORM-d) δ 7.91 (d, J=3.7 Hz, 2H), 7.56-7.51 (m, 4H), 7.49-7.32 (m, 10H), 6.86 (s, 2H), 4.51-4.42 (m, 2H), 4.37-3.84 (m, 8H), 3.68-3.58 (m, 2H), 3.48-3.38 (m, 2H), 2.49-2.36 (m, 2H), 1.87-1.74 (m, 4H), 1.69-1.20 (m, 12H).

Dimer IIc-2: LC-MS m/z 907 [M+H]$^+$; $^1$H NMR (400 MHz, CDCl$_3$) δ 7.89 (d, J=4.0 Hz, 2H), 7.53 (s, 2H), 7.41-7.39 (m, 2H), 7.37-7.33 (m, 4H), 6.94-6.89 (m, 4H), 6.82 (s, 2H), 4.47-4.38 (m, 2H), 4.21-3.96 (m, 8H), 3.84 (s, 6H), 3.59 (ddd, J=16.2, 11.4, 1.9 Hz, 2H), 3.39 (ddd, J=16.4, 5.2, 1.5 Hz, 2H), 2.03-1.92 (m, 4H), 1.86-1.70 (m, 6H), 1.62-1.51 (m, 4H), 1.45-1.30 (m, 12H).

Dimer IIc-3: LC-MS m/z 996 [M+H]$^+$; $^1$H NMR (400 MHz, CDCl$_3$) δ 7.89 (d, J=4.0 Hz, 2H), 7.52 (s, 2H), 7.42-7.38 (m, 2H), 7.35-7.32 (m, 4H), 6.97-6.91 (m, 4H), 6.82 (s, 2H), 4.46-4.38 (m, 2H), 4.20-4.03 (m, 12H), 3.80-3.75 (m, 4H), 3.63-3.54 (m, 2H), 3.48-3.47 (m, 6H), 3.42-3.34 (m, 2H), 2.04-1.92 (m, 4H), 1.86-1.71 (m, 6H), 1.60-1.51 (m, 4H), 1.45-1.29 (m, 12H).

Dimer IIc-4: LC-MS m/z 1017 [M+H]+; 1H NMR (400 MHz, CHLOROFORM-d) δ 7.88 (d, J=4.0 Hz, 2H), 7.52 (s, 2H), 7.39 (s, 2H), 7.33 (d, J=8.6 Hz, 4H), 6.91 (d, J=9.0 Hz, 4H), 6.82 (s, 2H), 4.46-4.37 (m, 2H), 4.21-4.01 (m, 8H), 3.91-3.85 (m, 8H), 3.63-3.53 (m, 2H), 3.42-3.35 (m, 2H), 3.23-3.16 (m, 8H), 1.97 (quin, J=6.9 Hz, 4H), 1.86-1.72 (m, 6H), 1.56 (s, 4H), 1.44-1.22 (m, 12H).

Dimer IIc-5: LC-MS m/z 1061 [M+H2O]+; 1H NMR (400 MHz, CHLOROFORM-d) δ 7.88 (d, J=4.0 Hz, 2H), 7.55-7.51 (m, 2H), 7.38 (s, 2H), 7.31 (d, J=8.8 Hz, 4H), 6.92 (d, J=8.8 Hz, 4H), 6.81 (s, 2H), 4.45-4.37 (m, 2H), 4.20-4.01 (m, 8H), 3.62-3.52 (m, 2H), 3.43-3.33 (m, 2H), 3.30-3.23 (m, 8H), 2.63-2.57 (m, 8H), 2.37 (s, 6H), 1.97 (quin, J=7.0 Hz, 4H), 1.87-1.71 (m, 6H), 1.66-1.48 (m, 4H), 1.43-1.22 (m, 12H).

Dimer IIc-6: LC-MS m/z 767 [M+H]+.

Dimer-linker IIIa-7: LC-MS m/z 777 [M+2H]+.

Dimer-linker IIIa-8: LC-MS m/z 1352.8 [M+H]+.

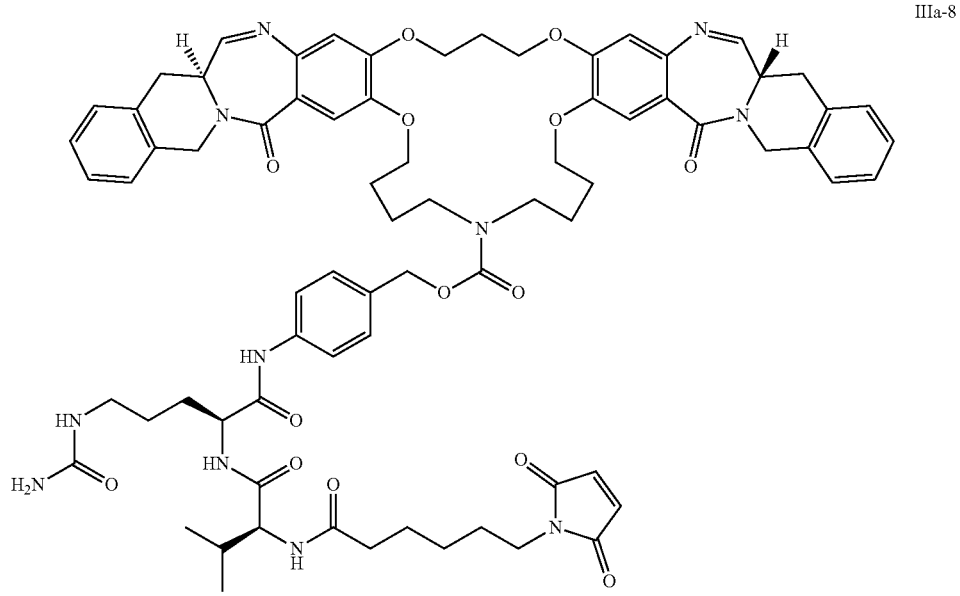 [SMILES: CC(C)[C@H](NC(=O)CCCCCN1C(=O)C=CC1=O)C(=O)N[C@@H](CCCNC(N)=O)C(=O)Nc1ccc(COC(=O)N2CCCCOc3cc4c(cc3OCCCOc3cc5c(cc3OCCCC2)C(=O)N2Cc3ccccc3C[C@H]2C=N5)N=C[C@@H]2Cc3ccccc3CN2C4=O)cc1]

IIIa-8

Dimer-linker IIIa-9: LC-MS m/z 1734.2 [M+H]+.

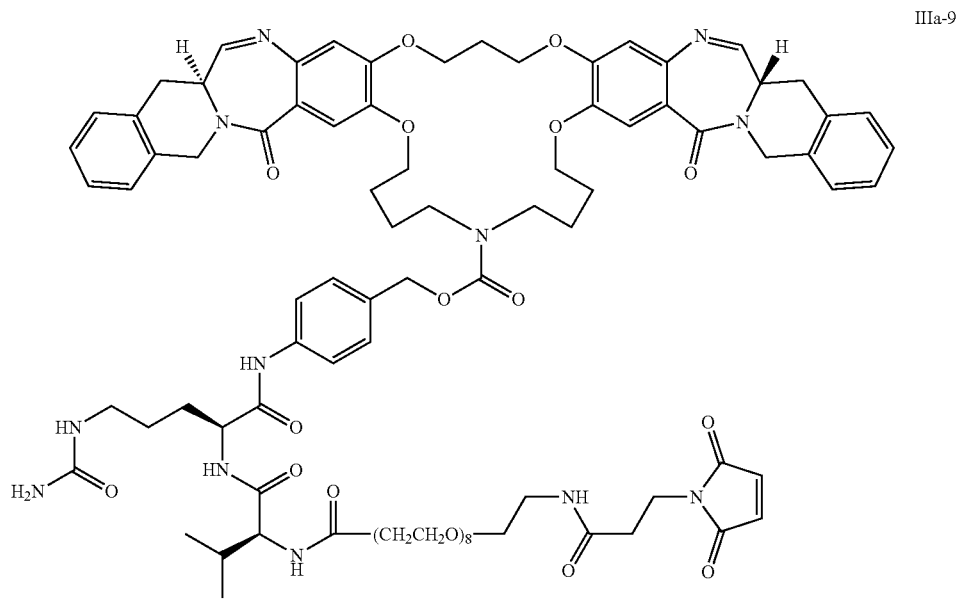

IIIa-9

Dimer-linker IIIa-10: LC-MS m/z 1633 [M+H]$^+$.

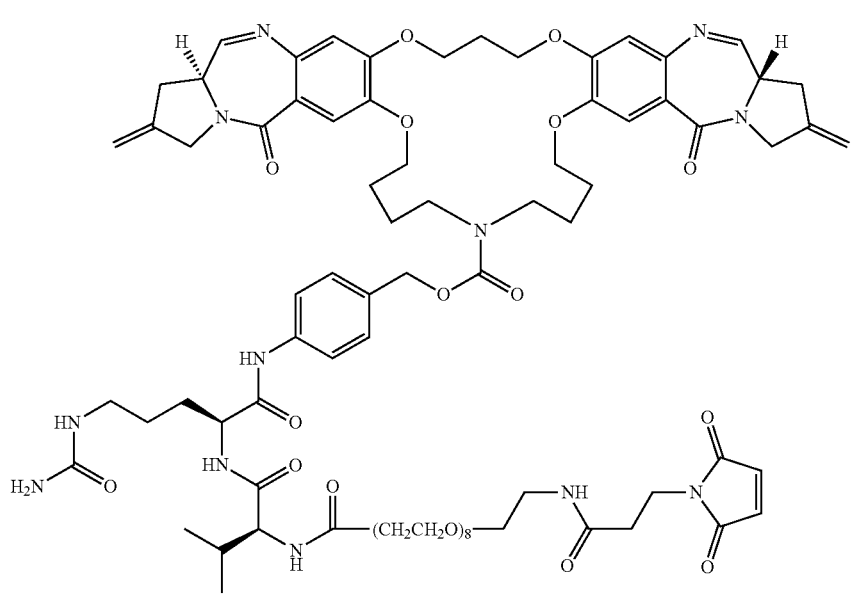

Dimer-linker IIIa-12: LC-MS m/z 1707 [M+H]$^+$.

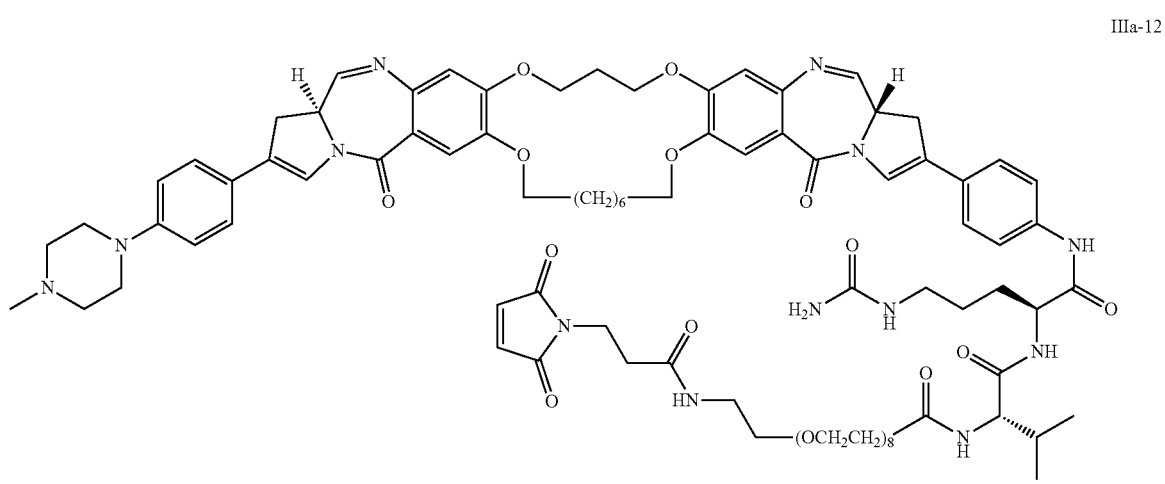

Example 18—Biological Activity (Dimers)

The cytotoxic activity of dimers of this invention against various different cancer cell lines is shown in Table 4. $H_{226}$ is a human lung cancer cell line. N87 is a human gastric cancer cell line. OVCAR3 is a human ovarian cancer cell line. HCT116 is a human colon cancer cell line. HCT116/VM46 is a human colon cancer cell line that is multi-drug and paclitaxel resistant.

TABLE 4

Cytotoxic Activity of Dimers

| Dimer | Cell Line (IC$_{50}$, nM) | | | | |
|---|---|---|---|---|---|
| | H226 | N87 | OVCAR3 | HCT116 | HCT116/VM46 |
| IIa-1 | 8.1 | 4.6 | 3.4 | — | 74 |
| IIa-2 | 1.6 | 2.7 | 1.2 | — | — |
| IIa-3 | 8.7 | 8.3 | 7.3 | — | — |
| IIa-4 | 12 | 22 | 20 | — | — |
| IIa-5 | 69 | 150 | 78 | — | — |
| IIa-6 | 110 | 310 | 140 | — | — |
| IIa-7 | 12 | 87 | 14 | — | — |
| IIa-8 | 10 | 15 | 9.9 | — | — |
| IIa-9 | 12 | 13 | 12 | — | — |
| IIa-10 | 2.0 | 2.3 | 0.47 | — | 11 |
| IIa-11 | 13 | 18 | 8.6 | — | 48 |
| IIa-12 | 0.32 | 0.89 | 0.52 | — | 4.8 |
| IIa-13 | 29 | 40 | 20 | 32 | 85 |
| IIa-14 | 21 | 23 | 50 | 38 | 170 |
| IIb-1 | 0.22 | 0.53 | 0.33 | — | 1.3 |
| IIb-2 | 3.0 | 2.5 | 1.3 | — | 17 |

TABLE 4-continued

Cytotoxic Activity of Dimers

| Dimer | Cell Line ($IC_{50}$, nM) | | | | |
|---|---|---|---|---|---|
| | H226 | N87 | OVCAR3 | HCT116 | HCT116/VM46 |
| IIb-3 | 5.9 | 11 | 3.5 | — | 13 |
| IIb-4 | 0.15 | 0.14 | 0.20 | 0.068 | 2.0 |
| IIb-5 | 0.45 | 0.35 | 0.60 | 0.077 | 7.3 |
| IIb-6 | 0.21 | 0.25 | 0.21 | 0.016 | 0.66 |
| IIb-7 | 0.56 | 0.40 | 0.56 | 0.19 | 3.5 |
| IIb-8 | 0.13 | 0.27 | 0.25 | 0.015 | 1.2 |
| IIc-1 | 12 | 12 | 7.6 | — | 30 |
| IIc-2 | 220 | 230 | >250 | 48 | >250 |
| IIc-3 | 32 | 29 | 104 | 13 | 58 |
| IIc-4 | — | — | — | — | — |
| IIc-5 | — | — | — | — | — |
| IIc-6 | 1.1 | 1.5 | 1.7 | 0.13 | 6.4 |
| IIc-7 | 0.99 | 0.62 | 1.8 | 0.17 | 1.1 |
| IIc-8 | 0.047 | 0.034 | 0.35 | 0.006 | 0.076 |
| IIc-9 | 0.33 | 0.68 | 1.0 | 0.063 | 0.16 |
| IIc-10 | 0.044 | 0.36 | 0.36 | 0.022 | 0.071 |
| IIc-11 | 0.36 | 0.56 | 0.31 | 0.063 | 0.36 |
| IId-1 | 0.66 | 1.4 | 1.2 | 0.14 | 1.2 |
| IId-2 | 0.56 | 1.1 | 0.71 | 0.11 | 2.8 |
| IId-3 | 0.035 | 0.072 | 0.26 | 0.045 | 0.033 |
| IId-4 | 8.1 | 12 | 20 | 2.0 | 4.8 |

Example 19—Biological Activity (ADCs)

Figure 17:
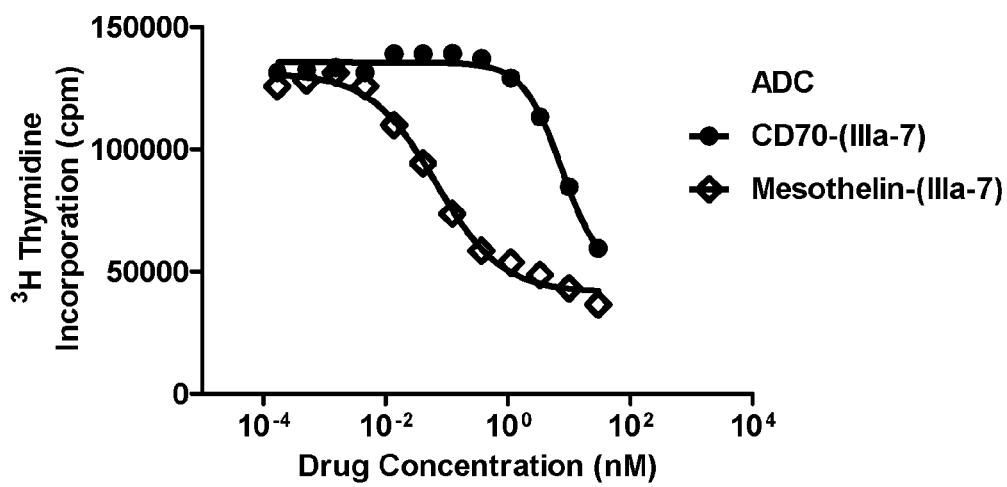
FIG. 17 shows the activity of two ADCs of this invention against cancer cells.

FIG. 17 shows the activity of two ADCs made with dimer-linker IIIa-7, one with an anti-CD70 antibody and one with an anti-mesothelin antibody. The ADCs were prepared following the procedure generally described above. Each had drug-antibody ratio of about 2. Activity was measured using a $^3$H thymidine incorporation assay, where a decrease in the incorporation of the radiolabeled thymidine indicates inhibition of cell proliferation (Cong et. al., U.S. Pat. No. 8,980,824 B2 (2015)). As can be seen from the figure, both ADCs were active, with $EC_{50}$ values in the range of nanomolar or less.

Example 20—Comparative Activity

Table 5 compares the cytotoxic activities of dimers of this invention against that of a non-macrocyclic PBD having a structure shown by formula A-4. It is noteworthy that the macrocyclic ring does not appear to introduce conformational constraints that interfere with the ability of both benzodiazepine rings to slide into the DNA minor groove, as evidence by the comparable, and in some cases, superior cytotoxic potency.

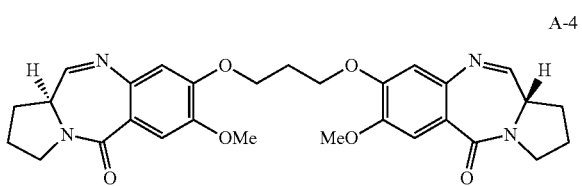 [SMILES: COc1cc2c(cc1OCCCOc1cc3c(cc1OC)C(=O)N1CCC[C@H]1C=N3)N=C[C@@H]1CCCN1C2=O]

A-4

TABLE 5

Comparative Activities

| Dimer | Cell line ($EC_{50}$, nM) | | |
|---|---|---|---|
| | H226 | N87 | OVCAR3 |
| A-4 | 70 | 63 | 56 |
| IIa-1 | 8.1 | 4.6 | 3.4 |
| IIa-2 | 1.6 | 2.7 | 1.2 |
| IIa-3 | 8.7 | 8.3 | 7.3 |
| IIa-4 | 12 | 22 | 20 |
| IIa-5 | 69 | 150 | 78 |
| IIa-6 | 110 | 310 | 140 |
| IIa-7 | 12 | 87 | 14 |
| IIa-8 | 10 | 15 | 9.9 |
| IIa-9 | 12 | 13 | 12 |

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

REFERENCES

Full citations for the following references, cited in abbreviated fashion by first author (or inventor) and date earlier in this specification, are provided below. Each of these references is incorporated herein by reference for all purposes.
Antonow et al., J. Med. Chem. 2010, 53, 2927.
Bose et al., J. Am. Chem. Soc. 1992, 114(12), 4939.
Bouchard et al., U.S. Pat. No. 8,404,678 B2 (2013).
Chari et al., WO 2013/177481 A1 (2013).
Commercon et al., U.S. Pat. No. 8,481,042 B2 (2013) [2013a].
Commercon et al., US 2013/0137659 A1 (2013) [2013b].
Fishkin et al., U.S. Pat. No. 8,765,740 B2 (2014).
Flygare et al., US 2013/0266595 A1 (2013).
Gauzy et al., U.S. Pat. No. 8,163,736 B2 (2012).
Gregson et al., Chem. Comm. 1999 (9), 797.
Gregson et al., Bioorg. Med. Chem. Lett. 2001, 11, 2859 [2001a].
Gregson et al., J. Med. Chem. 2001, 44, 737 [2001b].
Gregson et al., J. Med. Chem. 2004, 47, 1161.
Gregson et al., U.S. Pat. No. 7,612,062 B2 (2009).
Hartley, Exp. Opinion Investigational Drugs 2011, 20(6), 733.
Hartley et al., Investigational New Drugs 2012, 30, 950.
Howard, US 2014/0120118 A1 (2014) [2014a].
Howard, US 2014/0127239 A1 (2014) [2014b].
Howard, WO 2014/096365 A1 (2014) [2014c].
Howard, WO 2014/096368 A1 (2014) [2014d].
Howard, WO 2014/140174 A1 (2014) [2014e].

Howard et al., US 2007/0191349 A1 (2007).
Howard et al., U.S. Pat. No. 7,528,126 B2 (2009) [2009a].
Howard et al., U.S. Pat. No. 7,557,099 B2 (2009) [2009b].
Howard et al., U.S. Pat. No. 7,741,319 B2 (2010).
Howard et al., US 2011/0256157 A1 (2011).
Howard et al., U.S. Pat. No. 8,501,934 B2 (2013) [2013a].
Howard et al., U.S. Pat. No. 8,592,576 B2 (2013) [2013b].
Howard et al., US 2013/0028919 A1 (2013) [2013c].
Howard et al., WO 2013/041606 A1 (2013) [2013e].
Howard et al., U.S. Pat. No. 8,697,688 B2 (2014) [2014a].
Howard et al. US 2014/0234346 A1 (2014) [2014b].
Howard et al., US 2014/0274907 A1 (2014) [2014c].
Howard et al., WO 2014/140862 A2 (2014) [2014d].
Jeffrey et al., *Bioconj. Chem.* 2013, 24, 1256.
Jeffrey et al., US 2014/0286970 A1 (2014) [2014a].
Jeffrey et al., US 2014/0302066 A1 (2014) [2014b].
Kothakonda et al., *Bioorg. Med. Chem. Lett.* 2004, 14, 4371.
Li et al., U.S. Pat. No. 8,426,402 B2 (2013).
Li et al., WO 2014/031566 A1 (2014).
Liu et al., U.S. Pat. No. 7,244,724 B2 (2007).
Schrama et al., *Nature Rev. Drug Disc.* 2006, 5, 147.
Thurston et al., *J. Org. Chem.* 1996, 61(23), 8141.
Thurston et al., *J. Med. Chem.* 1999, 42, 1951.
Thurston et al., U.S. Pat. No. 7,049,311 B1 (2006).
Thurston et al., U.S. Pat. No. 7,407,951 B1 (2008).
Zhao et al., WO 2014/080251 A1 (2014)

What is claimed is:
1. A compound having a structure represented by formula I

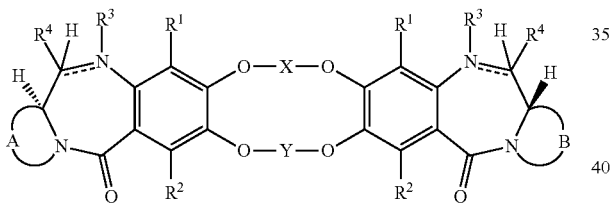

X is

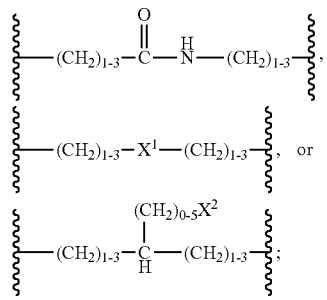

$X^1$ is $CH_2$, O, NH, $S(O)_{0-2}$, 3- to 7-membered cycloalkylene or heterocycloalkylene unsubstituted or substituted with $(CH_2)_{0-5}X^2$ or $O(CH_2)_{2-5}X^2$, or 5- to 6-membered arylene or heteroarylene unsubstituted or substituted with $(CH_2)_{0-5}X^2$ or $O(CH_2)_{2-5}X^2$;

each $X^2$ is independently Me, $CO_2H$, $NH_2$, $NH(C_1$-$C_5$ alkyl), $N(C_1$-$C_5$ alkyl)$_2$, SH, CHO, $N(CH_2CH_2)_2N(C_1$-$C_3$ alkyl), $N(CH_2CH_2)_2NH$, $NHNH_2$, or $C(=O)NHNH_2$;

Y is $(CH_2)_{4-6}CH=CH(CH_2)_{4-6}$, $(CH_2)_{4-6}X^1(CH_2)_{4-6}$, or $(CH_2)_2(OCH_2CH_2)_{2-3}$;

each $R^1$ and $R^2$ is independently H, F, Cl, Br, OH, $C_1$-$C_3$ alkyl, $O(C_1$-$C_3$ alkyl), cyano, $(CH_2)_{0-5}NH_2$, or $NO_2$;

each double line ==== in a diazepine ring system independently represents a single bond or a double bond;

each $R^3$ is H if the double line ==== to the N to which it is attached is a single bond and is absent if the double line is a double bond;

each $R^4$ is H, OH, $SO_3Na$, or $SO_3K$ if the double line ==== to the C to which it is attached is a single bond and is absent if the double line is a double bond;

A and B are independently according to formula Ia or Ib

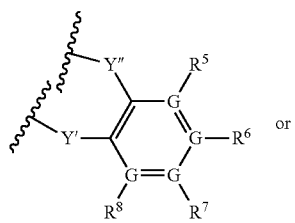

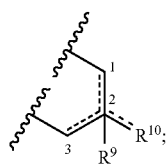

wherein, in formula Ia

Y' and Y" are independently absent, $CH_2$, C=O, or $CHR^{12}$; wherein each $R^{12}$ is independently F, Cl, Br, or $C_1$-$C_3$ alkyl, with the proviso that Y' and Y" are not both absent;

each G is independently C or N, with the proviso that no more than two Gs are N; and each $R^5$, $R^6$, $R^7$, and $R^8$ is independently H, $C_1$-$C_5$ alkyl, $C\equiv C(CH_2)_{1-5}X^2$, OH, $O(C_1$-$C_5$ alkyl), cyano, $NO_2$, F, Cl, Br, $O(CH_2CH_2O)_{1-8}(C_{1-3}$ alkyl), $(CH_2)_{0-5}X^2$, $O(CH_2)_{2-5}X^2$, 3- to 7-membered cycloalkyl or heterocycloalkyl unsubstituted or substituted with $(CH_2)_{0-5}X^2$ or $O(CH_2)_{2-5}X^2$, 5- to 6-membered aryl or heteroaryl unsubstituted or substituted with $(CH_2)_{0-5}X^2$ or $O(CH_2)_{2-5}X^2$,

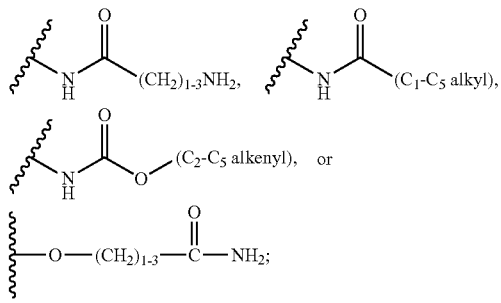

or where a $R^5$, $R^6$, $R^7$, or $R^8$ is attached to a G that is N, such $R^5$, $R^6$, $R^7$, or $R^8$ is absent;

and
wherein, in formula Ib,
the dotted lines indicate the optional presence of a C1-C2, C2-C3, or C2-$R^{10}$ double bond;
$R^{10}$ is H, =O, =$CH_2$, =CH($C_1$-$C_5$ alkyl), CH=CH $(CH_2)_{1-5}X^2$, C≡C$(CH_2)_1$—$X^2$, $C_1$-$C_5$ alkyl, OH, O($C_1$-$C_5$ alkyl), cyano, $NO_2$, F, Cl, Br, O($CH_2$ $CH_2O)_{1-8}$($C_{1-3}$ alkyl), $(CH_2)_{0-5}X^2$, 4- to 7-membered cycloalkyl, or heterocycloalkyl unsubstituted or substituted with $(CH_2)_{0-5}X^2$, O$(CH_2)_{2-5}X^2$, 3- to 7-membered cycloalkyl or heterocycloalkyl unsubstituted or substituted with $(CH_2)_{0-5}X^2$ or O$(CH_2)_{2-5}X^2$, 5- to 6-membered aryl or heteroaryl unsubstituted or substituted with $(CH_2)_{0-5}X^2$ or O$(CH_2)_{2-5}X^2$; and
$R^9$ is absent if a C1-C2, C2-C3, or C2-$R^{10}$ double bond is present and otherwise is H;
wherein a heterocycloalkyl group has 1 to 2 carbons replaced with a heteroatom independently selected from N, O, or S, where the N and S optionally may be oxidized and the N optionally may be quaternized; and
wherein a heteroaryl group has 1 to 4 heteroatoms independently selected from N, O, or S, where the N and S optionally may be oxidized and the N optionally may be quaternized;
or a pharmaceutically acceptable salt thereof.

2. A compound according to claim 1, having a structure represented by formula IIa:

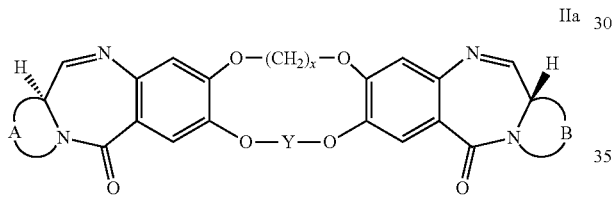

IIa wherein
x is 3 or 5;
Y is $(CH_2)_{7-12}$, $(CH_2)_2(OCH_2CH_2)_{1-3}$, $(CH_2)_{2-4}$NH$(CH_2)_{2-4}$ or $(CH_2)_{2-4}$NH$((CH_2)_{0-1}$phenyl$)(CH_2)_{2-4}$ where the phenyl group is optionally substituted with $NH_2$;
A is A1, A2, or A3

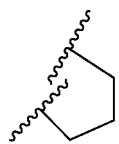

A1

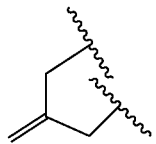

A2

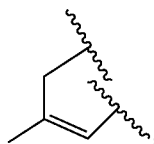

A3

B is B1, B2, or B3

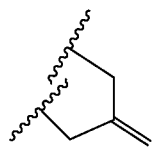

B1

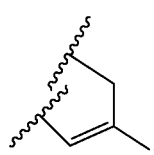

B2

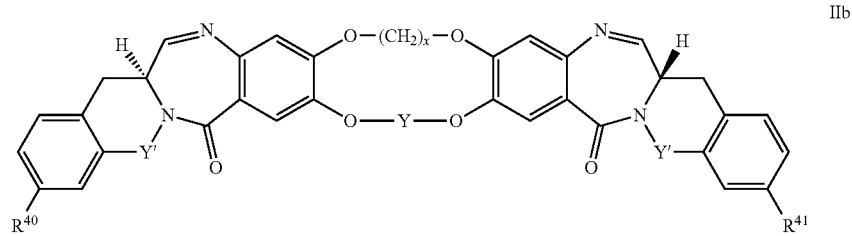

B3

3. A compound according to claim 1, having a structure represented by formula IIb:

IIb wherein x is 3 or 5;

each Y' is independently absent or $CH_2$;

Y is $(CH_2)_{7-12}$, $(CH_2)_2(OCH_2CH_2)_{1-3}$, $(CH_2)_{2-4}NH(CH_2)_{2-4}$ or $(CH_2)_{2-4}NH((CH_2)_{0-1}phenyl)(CH_2)_{2-4}$ where the phenyl group is optionally substituted with $NH_2$; and $R^{40}$ and $R^{41}$ are independently H, Cl, Br, OH, $O(C_{1-3}$ alkyl), $NH_2$, or $C_{1-3}$ alkyl.

4. A compound according to claim 1, having a structure represented by formula IIc

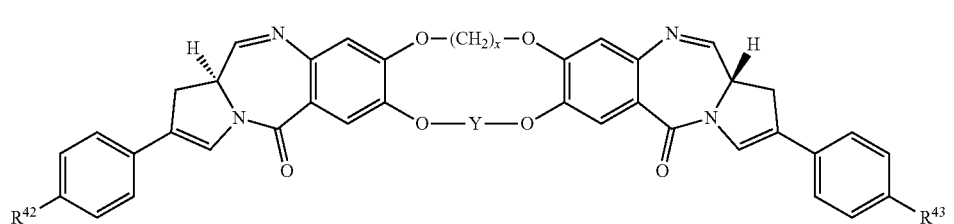

IIc wherein x is 3 or 5;

Y is $(CH_2)_{7-12}$, $(CH_2)_2(OCH_2CH_2)_{1-3}$, $(CH_2)_{2-4}NH(CH_2)_{2-4}$ or $(CH_2)_{2-4}NH((CH_2)_{0-1}phenyl)(CH_2)_{2-4}$ where the phenyl group is optionally substituted with $NH_2$; and $R^{42}$ and $R^{43}$ are independently H, OMe, $NH_2$, $OCH_2CH_2OMe$, $N(CH_2CH_2)O$, $N(CH_2CH_2)NMe$, or $N(CH_2CH_2)NH$.

5. A compound according to claim 1, having a structure represented by formula IIb-6, IIc-8, IIc-9, IIc-10, IIc-11, IId-1, IId-2, or IId-3

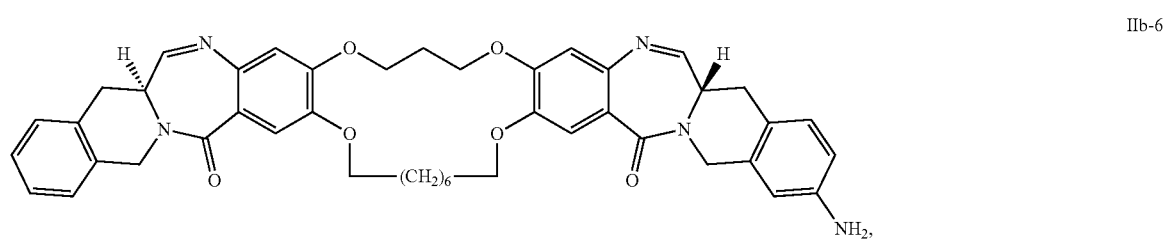

IIb-6

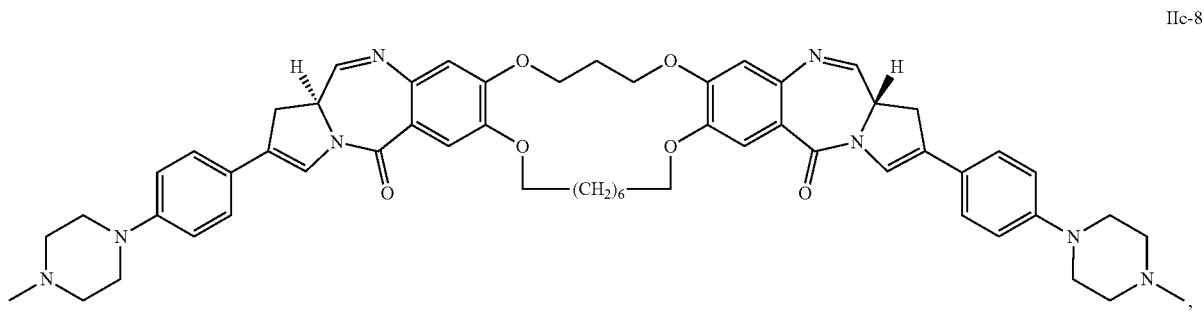

IIc-8

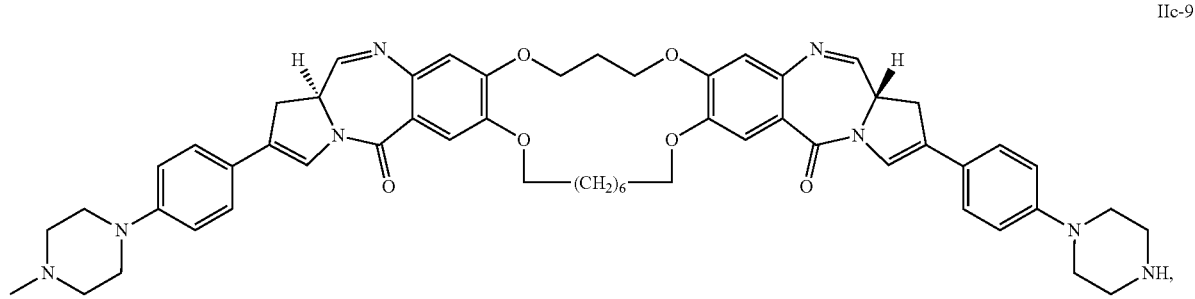

IIc-9

-continued
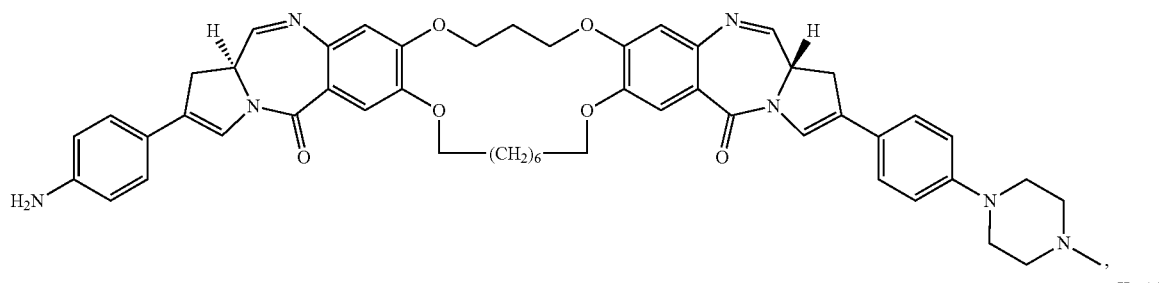
IIc-10
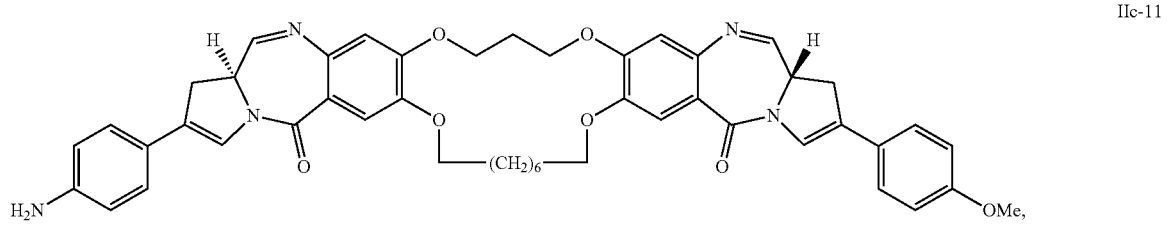
IIc-11
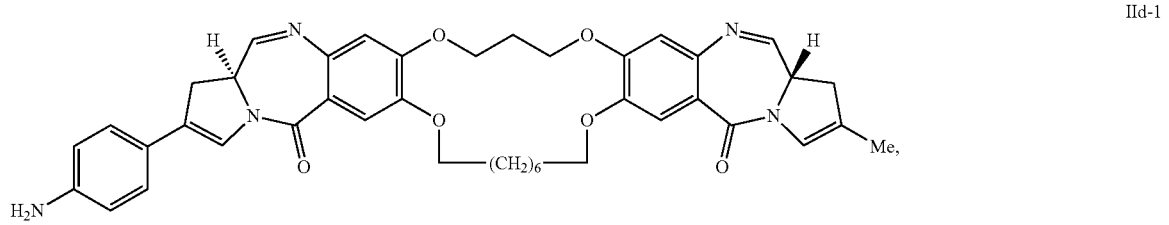
IId-1
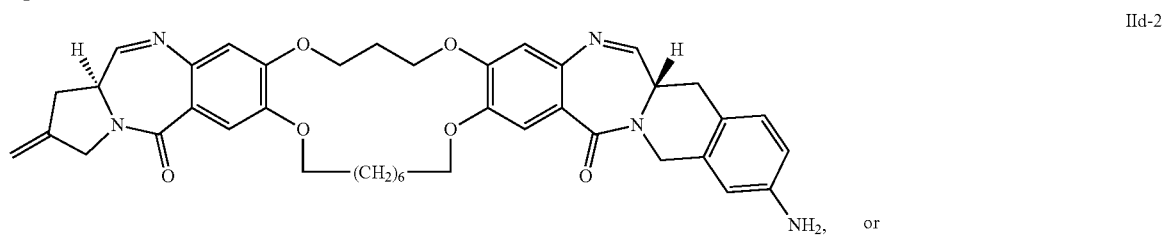
IId-2
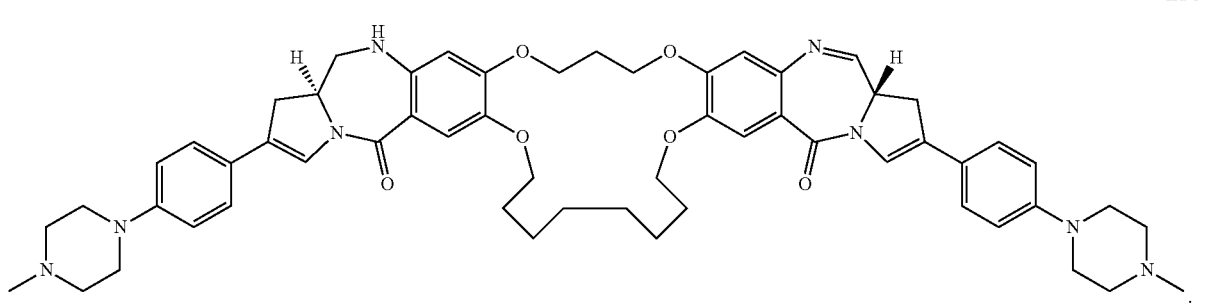
IId-3
6. A compound having a structure represented by formula III:
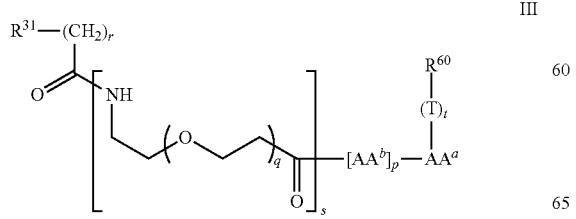

wherein
R⁶⁰ is according to formula IIIa, IIIa', or IIIa"

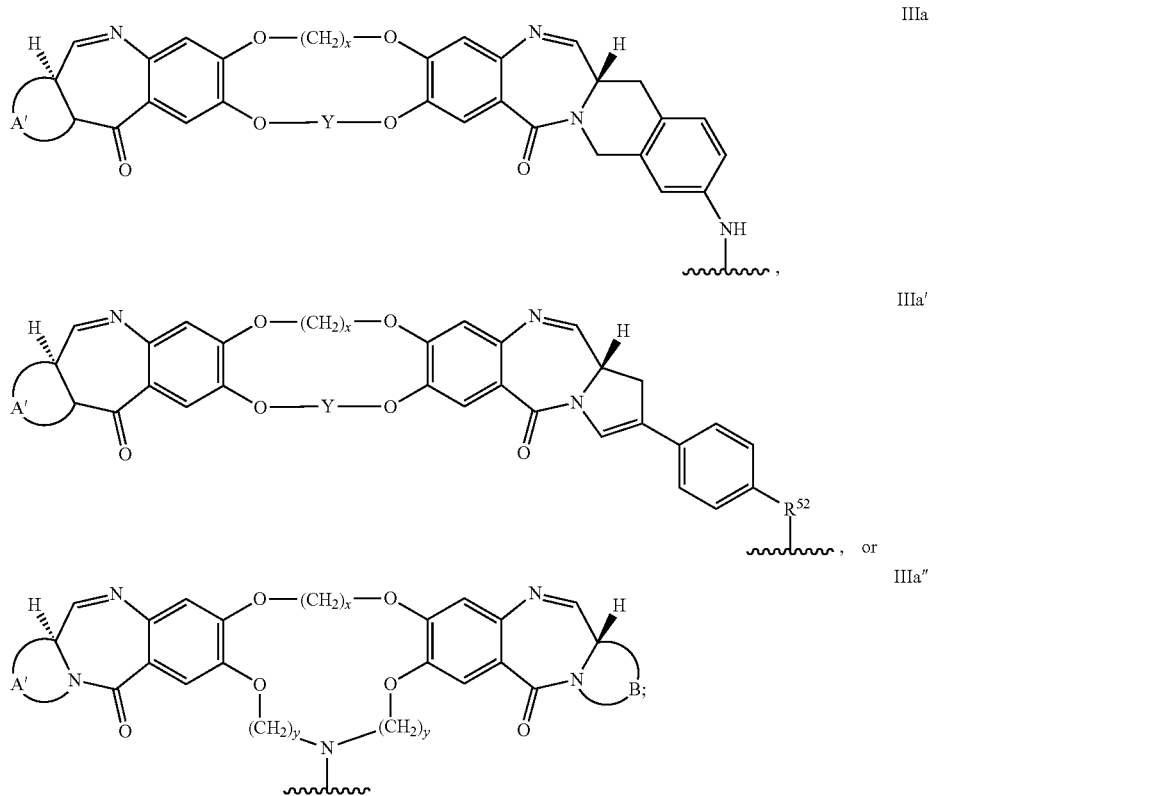

Y is $(CH_2)_{6-10}$;
x is 3 or 5;
each y is independently 2, 3, or 4;
A and B are independently according to formula Ia or Ib

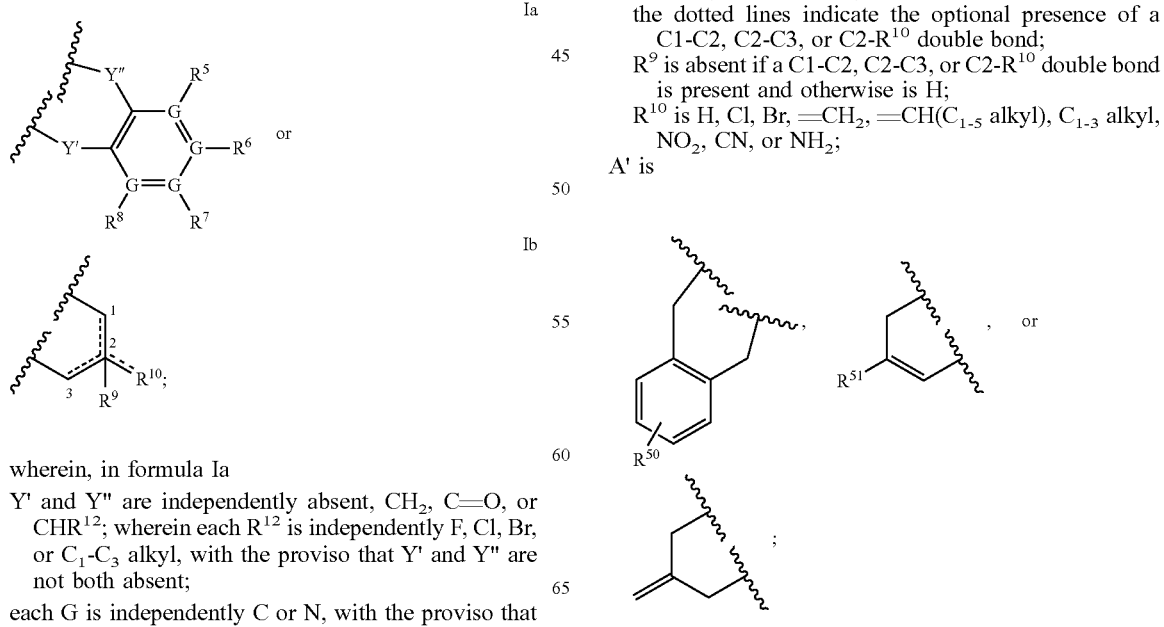

wherein, in formula Ia
Y' and Y" are independently absent, $CH_2$, C=O, or $CHR^{12}$; wherein each $R^{12}$ is independently F, Cl, Br, or $C_1$-$C_3$ alkyl, with the proviso that Y' and Y" are not both absent;
each G is independently C or N, with the proviso that no more than two Gs are N; and each $R^5$, $R^6$, $R^7$, and $R^8$ is independently H, Cl, Br, $C_{1-3}$ alkyl, $NO_2$, CN, $NH_2$, $O(C_{1-3}$ alkyl), or $(OCH_2CH_2)_{1-2}O(C_{1-3}$ alkyl);
or where a $R^5$, $R^6$, $R^7$, or $R^8$ is attached to a G that is N, such $R^5$, $R^6$, $R^7$, or $R^8$ is absent;
and
wherein, in formula Ib,
the dotted lines indicate the optional presence of a C1-C2, C2-C3, or C2-$R^{10}$ double bond;
$R^9$ is absent if a C1-C2, C2-C3, or C2-$R^{10}$ double bond is present and otherwise is H;
$R^{10}$ is H, Cl, Br, =$CH_2$, =CH($C_{1-5}$ alkyl), $C_{1-3}$ alkyl, $NO_2$, CN, or $NH_2$;
A' is $R^{50}$ is H, Cl, Br, $C_{1-3}$ alkyl, $NO_2$, CN, $NH_2$, $O(C_{1-3}$ alkyl), or $(OCH_2CH_2)_{1-2}O(C_{1-3}$ alkyl);
$R^{51}$ is H, Cl, Br, $C_{1-3}$ alkyl, $NO_2$, CN, or $NH_2$;
T is a self-immolating group;
t is 0 or 1;
$AA^a$ and each $AA^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
p is 1, 2, 3, or 4;
q is 1, 2, 3, 4, 5, 6, 7, 8, 9, or 10;
r is 1, 2, 3, 4, or 5;
s is 0 or 1; and
$R^{31}$ is

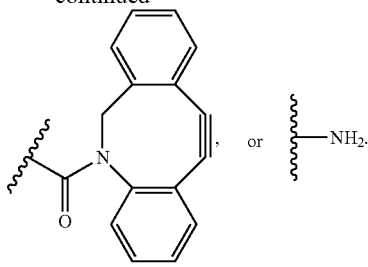

7. A compound according to claim 6, wherein $R^{60}$ is IIIa.
8. A compound according to claim 6, wherein $R^{60}$ is IIIa'.
9. A compound according to claim 6, wherein $R^{60}$ is IIIa".
10. A compound according to claim 6, having a structure represented by formula IIIa-1, IIIa-2, IIIa-3, IIIa-4, IIIa-5, IIIa-6, or IIIa-7

IIIa-1

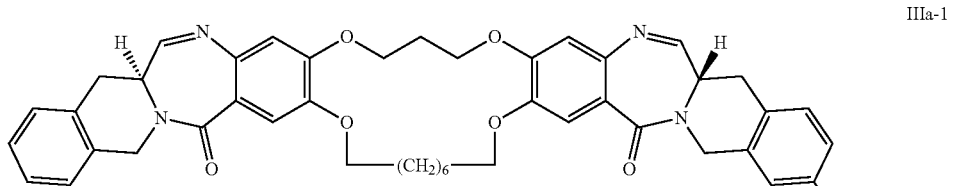
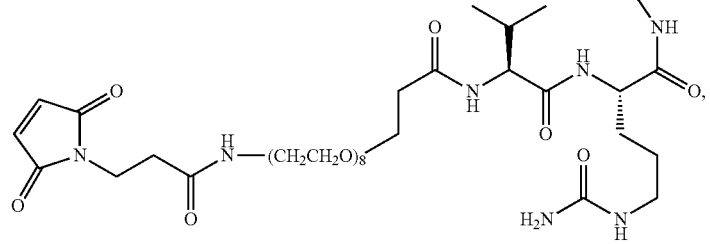

IIIa-2

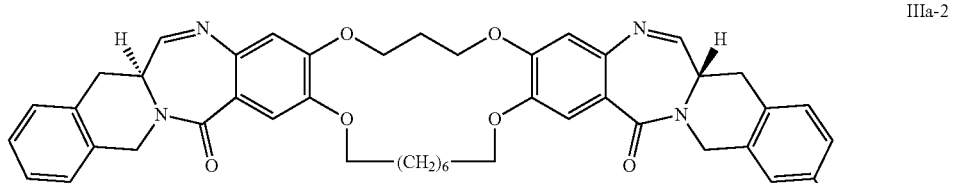
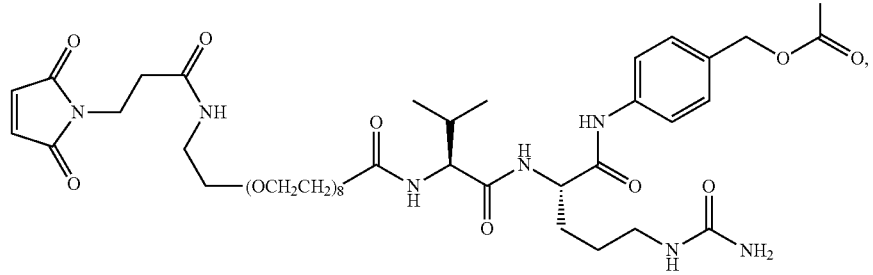

-continued
IIIa-3
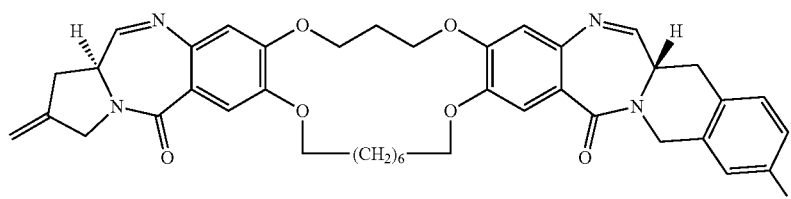
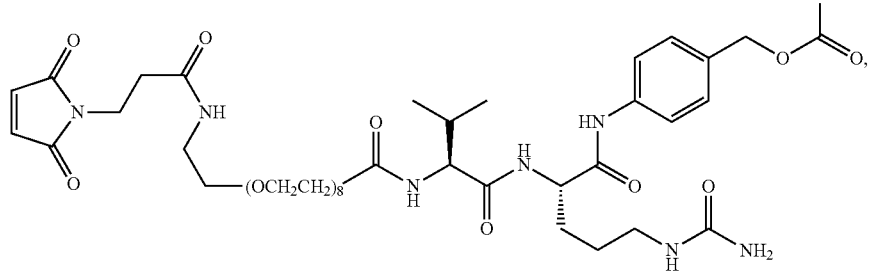
IIIa-4
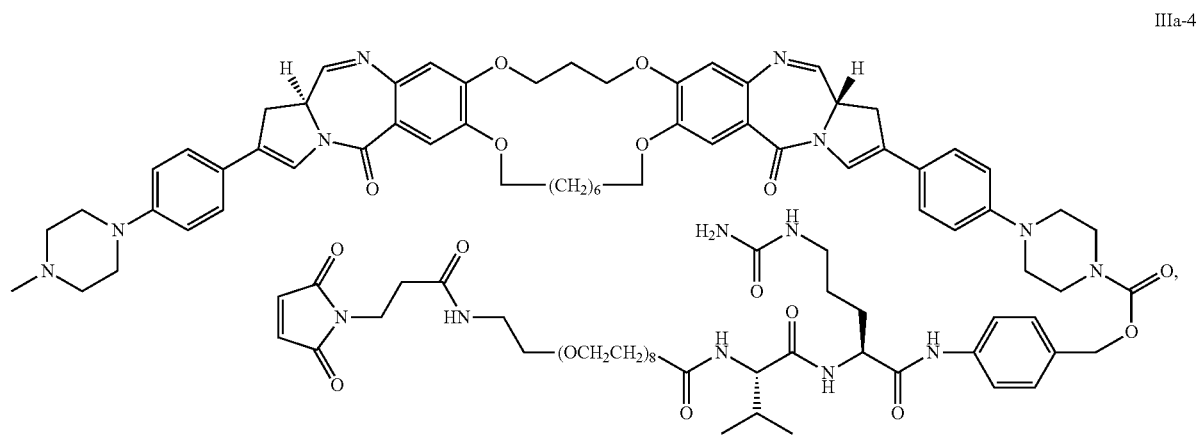
IIIa-5
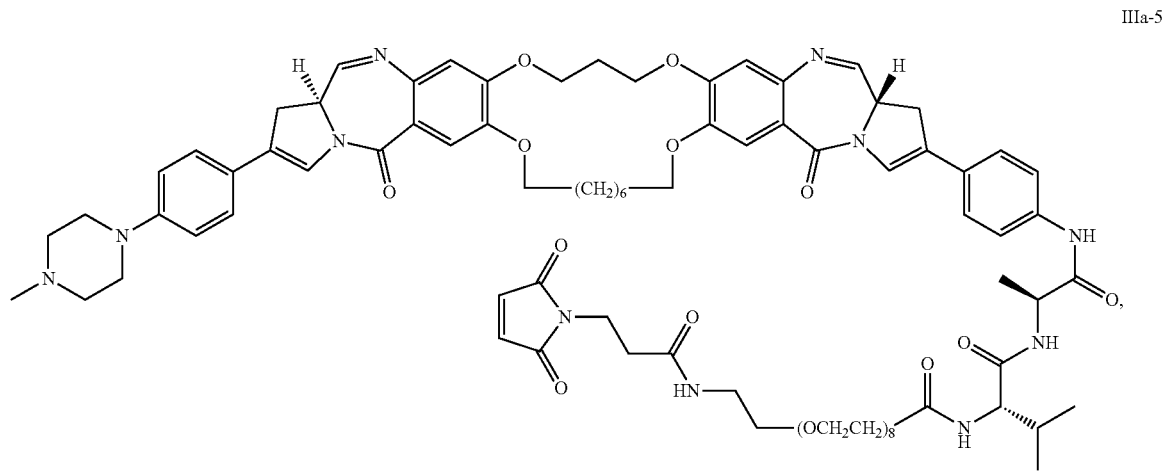

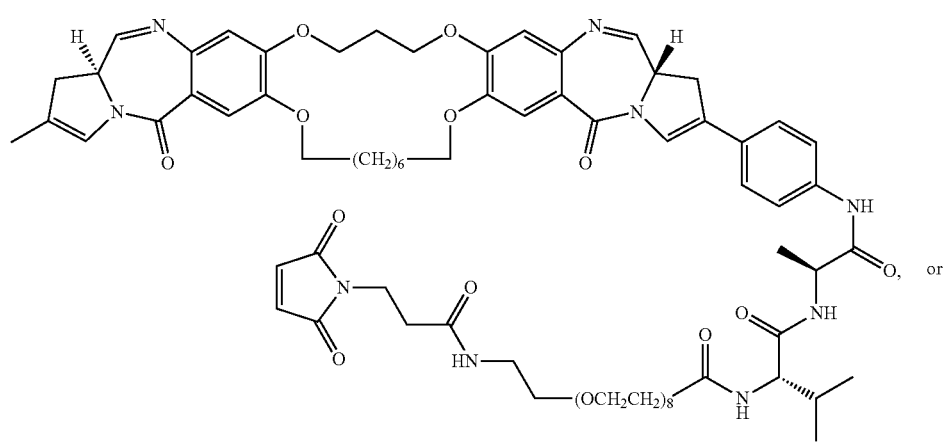
IIIa-6
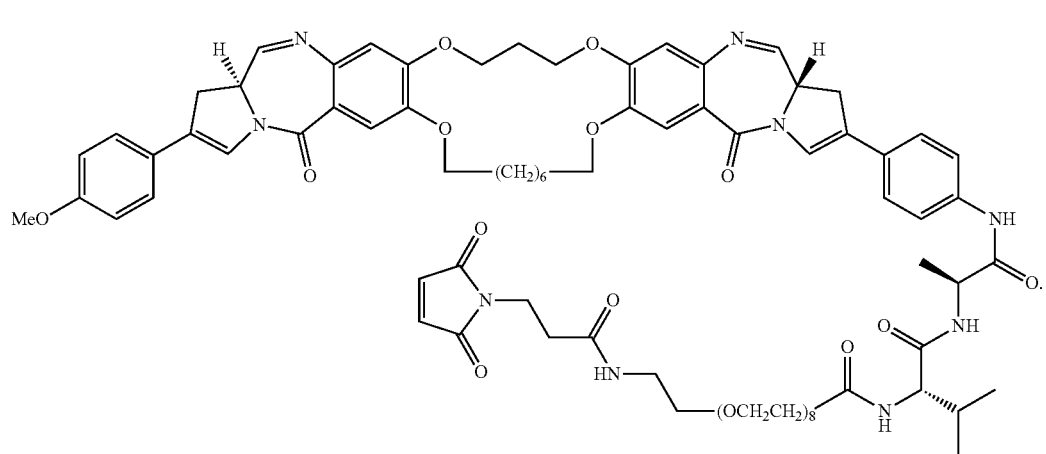
IIIa-7
11. A conjugate comprising a compound according to claim 1 conjugated to an antibody.
12. A conjugate according to claim 11, having a structure represented by formula IV:
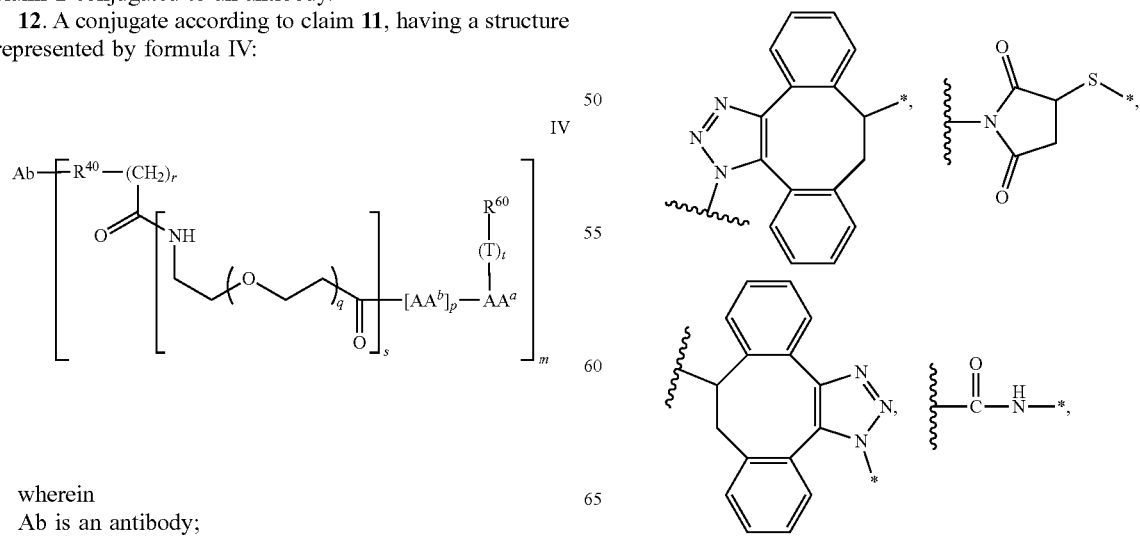
wherein
Ab is an antibody;
m is 1, 2, 3, or 4;

-continued

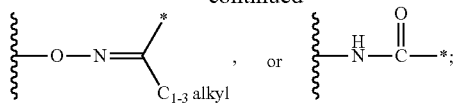, or 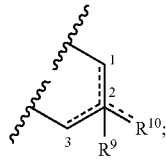;

where the open valence of $R^{40}$ that is bonded to Ab is denoted by an asterisk (*) and the open valence of $R^{40}$ that is bonded to $(CH_2)_r$ is denoted by a wavy line (~~~);

$R^{60}$ is according to formula IIIa, IIIa', or IIIa"

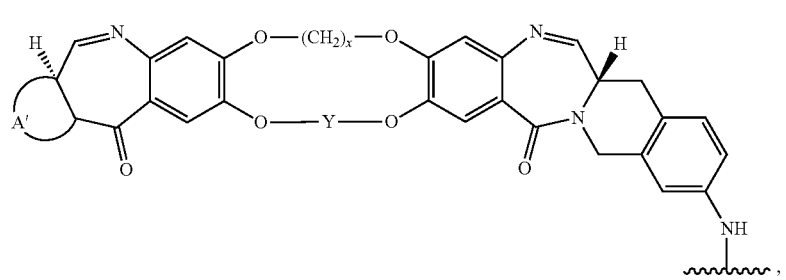

IIIa

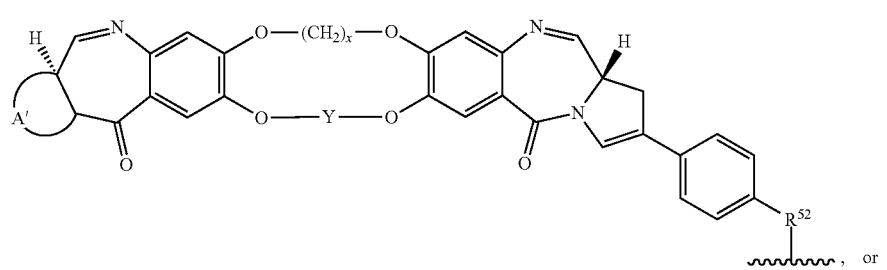

IIIa'

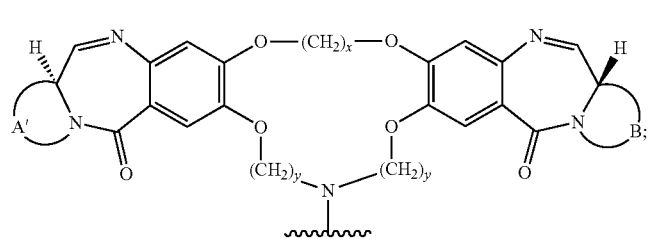

IIIa"

Y is $(CH_2)_{6-10}$;
x is 3 or 5;
each y is independently 2, 3, or 4;
A and B are independently according to formula Ia or Ib

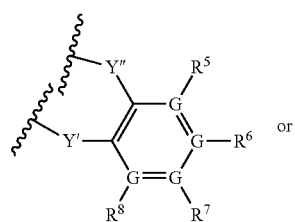

Ia

Ib wherein, in formula Ia
Y' and Y" are independently absent, $CH_2$, C=O, or $CHR^{12}$; wherein each $R^{12}$ is independently F, Cl, Br, or $C_1$-$C_3$ alkyl, with the proviso that Y' and Y" are not both absent;
each G is independently C or N, with the proviso that no more than two Gs are N; and
each $R^5$, $R^6$, $R^7$, and $R^8$ is independently H, Cl, Br, $C_{1-3}$ alkyl, $NO_2$, CN, $NH_2$, $O(C_{1-3}$ alkyl), or $(OCH_2CH_2)_{1-2}O(C_{1-3}$ alkyl);
or where a $R^5$, $R^6$, $R^7$, or $R^8$ is attached to a G that is N, such $R^5$, $R^6$, $R^7$, or $R^8$ is absent;
and
wherein, in formula Ib,
the dotted lines indicate the optional presence of a C1-C2, C2-C3, or C2-$R^{10}$ double bond;
$R^9$ is absent if a C1-C2, C2-C3, or C2-$R^{10}$ double bond is present and otherwise is H;

$R^{10}$ is H, Cl, Br, =CH$_2$, =CH(C$_{1-5}$ alkyl), C$_{1-3}$ alkyl, NO$_2$, CN, or NH$_2$;

A' is

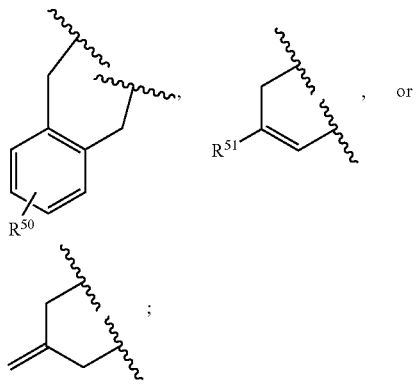

$R^{50}$ is H, Cl, Br, C$_{1-3}$ alkyl, NO$_2$, CN, NH$_2$, O(C$_{1-3}$ alkyl), or (OCH$_2$CH$_2$)$_{1-2}$O(C$_{1-3}$ alkyl);

$R^{51}$ is H, Cl, Br, C$_{1-3}$ alkyl, NO$_2$, CN, NH$_2$;

T is a self-immolating group;

t is 0 or 1;

AA$^a$ and each AA$^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;

p is 1, 2, 3, or 4;

q is 1, 2, 3, 4, 5, 6, 7, 8, 9, or 10;

r is 1, 2, 3, 4, or 5; and s is 0 or 1.

13. A conjugate according to claim 12, wherein $R^{60}$ is IIIa.

14. A conjugate according to claim 12, wherein $R^{60}$ is IIIa'.

15. A conjugate according to claim 12, wherein $R^{60}$ is IIIa".

16. A pharmaceutical formulation comprising a conjugate according to claim 12 and a pharmaceutically acceptable excipient.

17. A method of treating a cancer in a subject suffering from such cancer, comprising administering to the subject a therapeutically effective amount of a conjugate according to claim 12, wherein the cancer is lung, gastric, or ovarian cancer.

* * * * *

UNITED STATES PATENT AND TRADEMARK OFFICE
CERTIFICATE OF CORRECTION

PATENT NO.       : 9,688,694 B2
APPLICATION NO.  : 15/189388
DATED            : June 27, 2017
INVENTOR(S)      : Yong Zhang et al.

It is certified that error appears in the above-identified patent and that said Letters Patent is hereby corrected as shown below:

In the Claims

In Claim 1,
Column 81, Line 6:
Delete "$(CH_2)_{1\text{-}}X^2$," and insert -- $(CH_2)_{1\text{-}5}X^2$, --

In Claim 2,
Column 82, Lines 10-15:

After "  " insert -- and --

In Claim 6,
Columns 87-88, Lines 25-35 (Structure IIIa):

Delete " 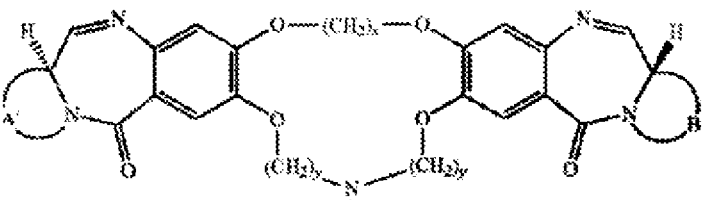 " and

Signed and Sealed this
Twelfth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,688,694 B2

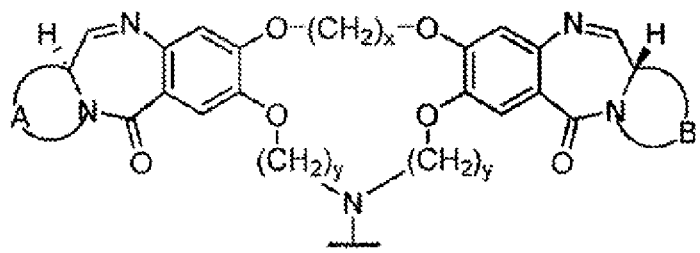

insert -- --

In Claim 12,
Columns 95-96, Lines 35-49 (Structure IIIa):

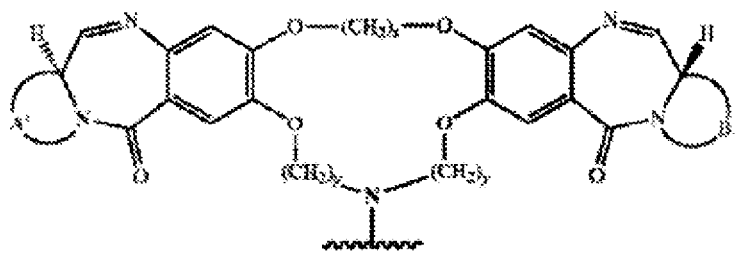

Delete " " and

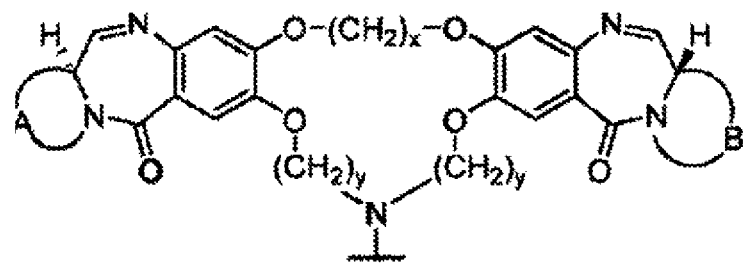

insert -- --